United States Patent
Balagurusamy et al.

(10) Patent No.: US 9,632,033 B2
(45) Date of Patent: *Apr. 25, 2017

(54) CELLULAR PHONE BASED OPTICAL DETECTION OF SPECIFIC NUCLEIC ACID SEQUENCES

(71) Applicant: International Business Machines Corporation, Armonk, NY (US)

(72) Inventors: Venkat K. Balagurusamy, Suffern, NY (US); Stephen J. Heisig, Tarrytown, NY (US); Gong Su, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/746,135

(22) Filed: Jun. 22, 2015

(65) Prior Publication Data
US 2016/0350937 A1 Dec. 1, 2016

Related U.S. Application Data

(63) Continuation of application No. 14/725,668, filed on May 29, 2015.

(51) Int. Cl.
*C12Q 1/68* (2006.01)
*C12M 1/34* (2006.01)
(Continued)

(52) U.S. Cl.
CPC ......... *G01N 21/75* (2013.01); *G01N 21/6428* (2013.01); *G01N 21/6458* (2013.01);
(Continued)

(58) Field of Classification Search
CPC ......... C12Q 1/68; C12M 1/34; G01N 33/543; G01N 21/6458; G01R 33/36; G06T 7/204
(Continued)

(56) References Cited

U.S. PATENT DOCUMENTS 5,756,292 A * 5/1998 Royer ................. C12Q 1/6816
250/372
2013/0157877 A1* 6/2013 Plenat ................. C12Q 1/6837
506/7

(Continued)

OTHER PUBLICATIONS

Nelson et al, Tethered Particle Motion as a Diagnostic of DNA Tether Length, 2006, J. Phys. Chem. B, 110, 17260-17267.*
Kamiya et al, Surface modification and characterization for dispersion stability of inorganic nanometer-scaled particles in liquid media, 2010, Sci. Technolo. Adv. Mater, 044304, pp. 1-7.*
(Continued)

*Primary Examiner* — Narayan Bhat
(74) *Attorney, Agent, or Firm* — Cantor Colburn LLP; Mercedes Hobson

(57) ABSTRACT

A technique relates to determining a presence of a known nucleic acid sequence of a known molecule in a sample. A sample surface is coated with a select segment of the known molecule. Beads are coated with a first molecule. A targeted nucleic acid sequence is attached to a second molecule that binds to the first molecule, such that the targeted nucleic acid sequence is attached to the beads via first and second molecules. The sample is placed on the sample surface. The sample includes the liquid medium, beads, and targeted nucleic acid sequence being tested. Brownian motion of beads is monitored to determine whether the Brownian motion of the beads is restricted or not restricted. When the Brownian motion of beads is restricted, the presence of the known nucleic acid sequence is in the sample, thus indicating that the targeted nucleic acid sequence is the known nucleic acid sequence.

8 Claims, 27 Drawing Sheets

(51) Int. Cl.

| | |
|---|---|
| *C40B 40/06* | (2006.01) |
| *G01N 21/75* | (2006.01) |
| *G02B 21/36* | (2006.01) |
| *G02B 21/00* | (2006.01) |
| *G01N 21/64* | (2006.01) |
| *G06K 9/00* | (2006.01) |
| *G06T 7/20* | (2017.01) |

(52) U.S. Cl.
CPC ....... *G02B 21/0008* (2013.01); *G02B 21/367* (2013.01); *G06K 9/0014* (2013.01); *G06T 7/204* (2013.01); *G01N 2201/062* (2013.01); *G01N 2201/0612* (2013.01); *G06T 2207/10016* (2013.01); *G06T 2207/30072* (2013.01)

(58) Field of Classification Search
USPC .................................. 435/6.1, 287.2; 506/16
See application file for complete search history.

(56) References Cited

U.S. PATENT DOCUMENTS

2015/0148661 A1* 5/2015 Weaver .............. G01R 33/1269
 600/420
2015/0307926 A1* 10/2015 Celedon ............... C12Q 1/6834
 435/5

OTHER PUBLICATIONS

Song et al, Tethered particle motion with single DNA molecules, 2015, Am. J. Phys. 83, 418-426.*
List of IBM Patents or Patent Applications Treated as Related; Date Filed: Jun. 22, 2015, p. 1-2.
Venkat K. Balagurusamy, "Cellular Phone Based Optical Detection of Specific Nucleic Acid Sequences", U.S. Appl. No. 14/725,668, Date Filed: May 29, 2015.

* cited by examiner

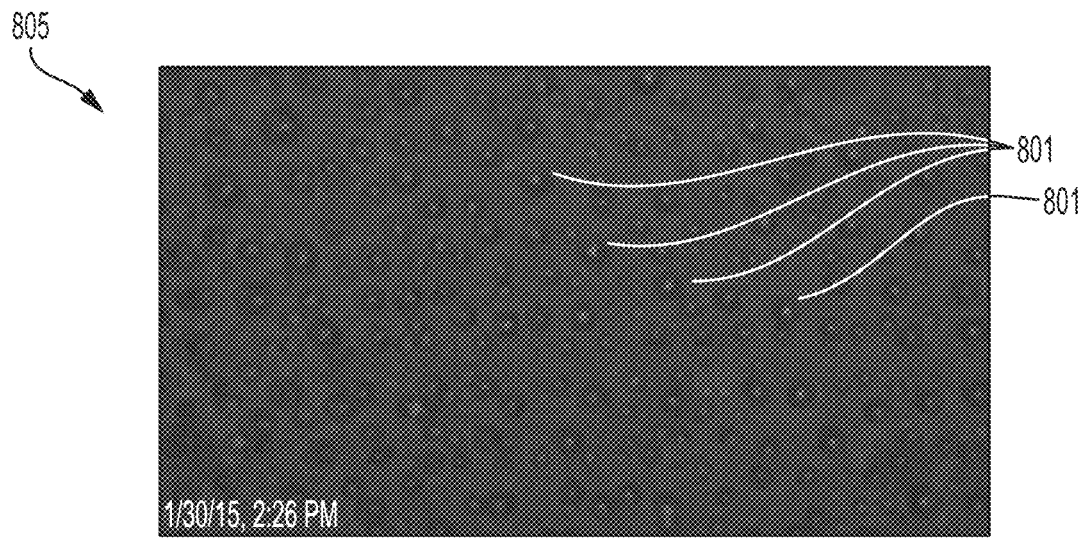
FIG. 8A1
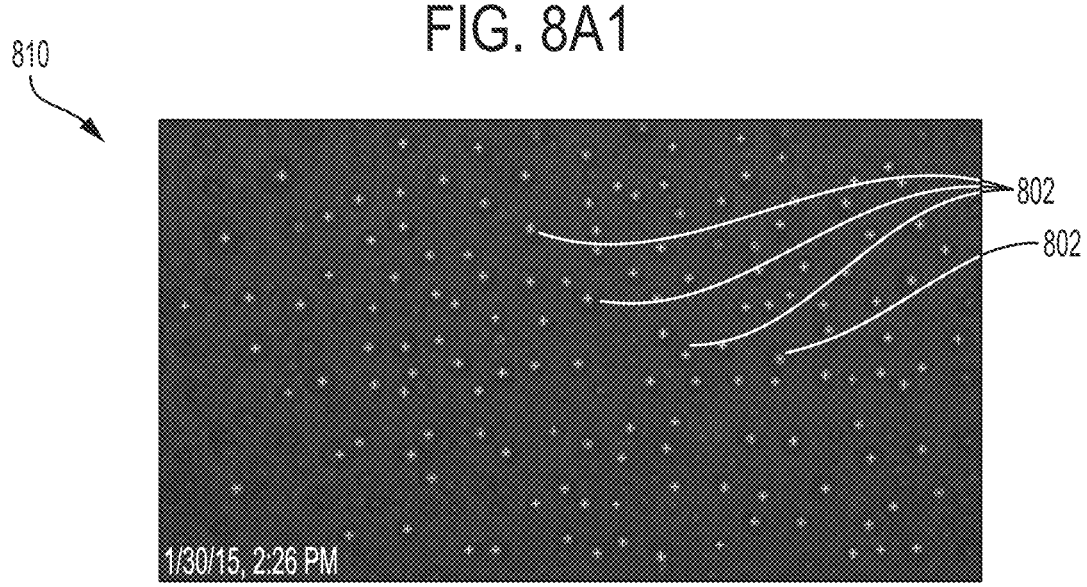
FIG. 8A2

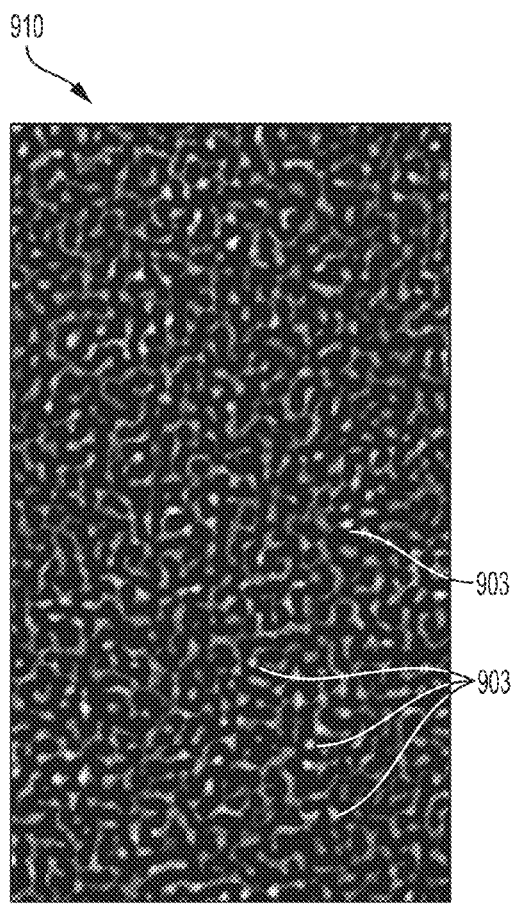 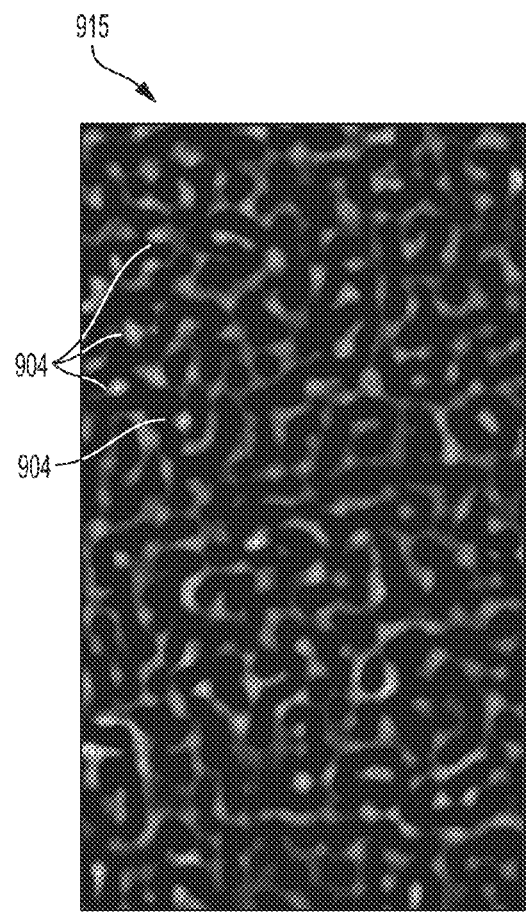
FIG. 9B-1    FIG. 9B-2

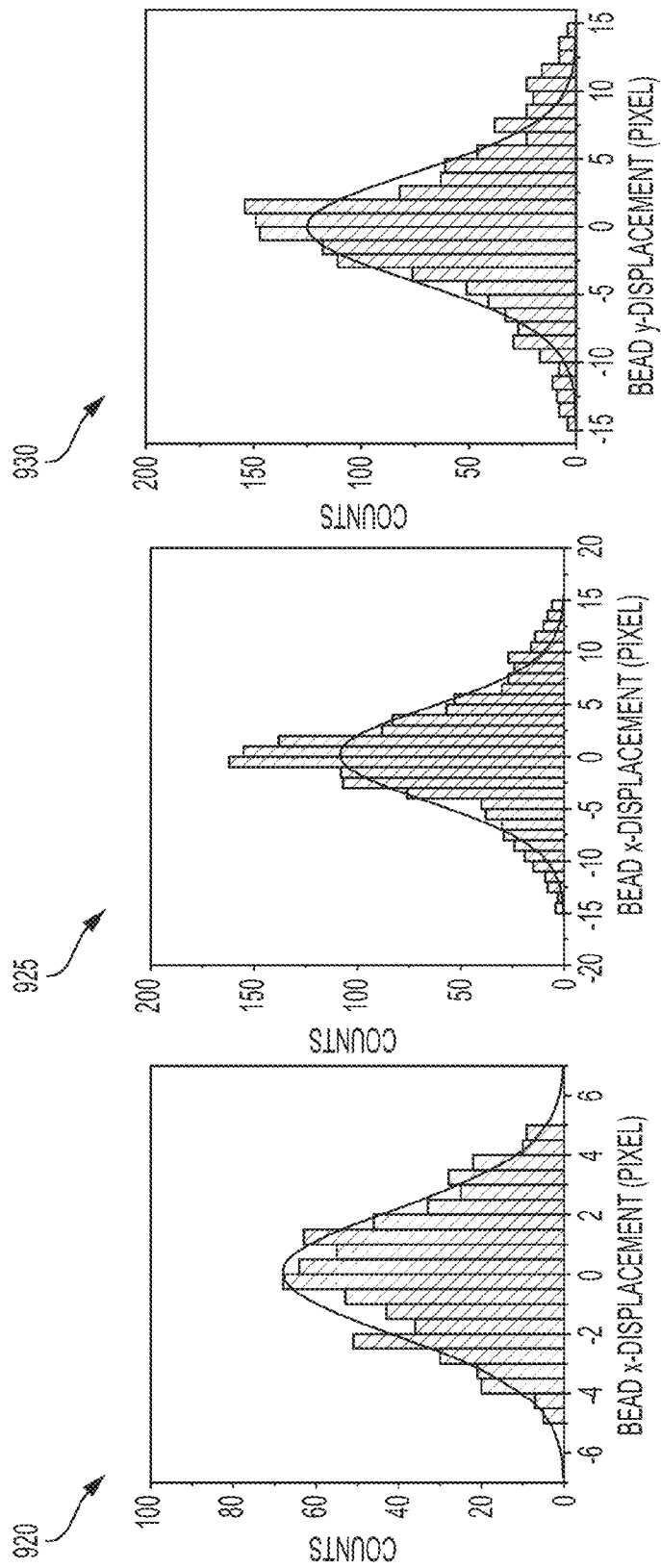

SEQUENCE LISTING

```
<160> NUMBER OF SEQ ID NOS: 9

<210> SEQ ID NO 1
<211> LENGTH: 150
<212> TYPE: DNA
```

```
<213> ORGANISM: Artificial Sequence
<220> FEATURE:
<223> OTHER INFORMATION: poly-thymine

<400> SEQUENCE: 1
tttttttttt tttttttttt tttttttttt tttttttttt tttttttttt tttttttttt    60
tttttttttt tttttttttt tttttttttt tttttttttt tttttttttt tttttttttt   120
tttttttttt tttttttttt tttttttttt                                    150

<210> SEQ ID NO 2
<211> LENGTH: 48502
<212> TYPE: DNA
<213> ORGANISM: Lambda bacteriophage

<400> SEQUENCE: 2
gggcggcgac ctcgcgggtt ttcgctattt atgaaaattt tccggtttaa ggcgtttccg    60
ttcttcttcg tcataactta atgttttat ttaaaatacc ctctgaaaag aaaggaaacg   120
acaggtgctg aaagcgaggc tttttggcct ctgtcgtttc ctttctctgt ttttgtccgt   180
ggaatgaaca atggaagtca acaaaaagca gctggctgac attttcggtg cgagtatccg   240
taccattcag aactggcagg aacagggaat gcccgttctg cgaggcggtg gcaagggtaa   300
tgaggtgctt tatgactctg ccgccgtcat aaaatggtat gccgaaaggg atgctgaaat   360
tgagaacgaa aagctgcgcc gggaggttga agaactgcgg caggccagcg aggcagatct   420
ccagccagga actattgagt acgaacgcca tcgacttacg cgtgcgcagg ccgacgcaca   480
ggaactgaag aatgccagag actccgctga agtggtggaa accgcattct gtactttcgt   540
gctgtcgcgg atcgcaggtg aaattgccag tattctcgac gggctccccc tgtcggtgca   600
gcggcgtttt ccggaactgg aaaaccgaca tgttgatttc ctgaaacggg atatcatcaa   660
agccatgaac aaagcagccg cgctggatga actgataccg gggttgctga gtgaatatat   720
cgaacagtca ggttaacagg ctgcggcatt ttgtccgcgc cgggcttcgc tcactgttca   780
ggccggagcc acagaccgcc gttgaatggg cggatgctaa ttactatctc ccgaaagaat   840
ccgcatacca ggaagggcgc tgggaaacac tgcccttca gcgggccatc atgaatgcga   900
tgggcagcga ctacatccgt gaggtgaatg tggtgaagtc tgcccgtgtc ggttattcca   960
aaatgctgct gggtgtttat gcctacttta tagagcataa gcagcgcaac acccttatct  1020
ggttgccgac ggatggtgat gccgagaact ttatgaaaac ccacgttgag ccgactattc  1080
gtgatattcc gtcgctgctg gcgctggccc cgtggtatgg caaaaagcac cgggataaca  1140
cgctcaccat gaagcgtttc actaatgggc gtggcttctg gtgcctgggc ggtaaagcgg  1200
caaaaaacta ccgtgaaaag tcggtggatg tggcgggtta tgatgaactt gctgcttttg  1260
atgatgatat tgaacaggaa ggctctccga cgttcctggg tgacaagcgt attgaaggct  1320
cggtctggcc aaagtccatc cgtggctcca cgccaaaagt gagaggcacc tgtcagattg  1380
agcgtgcagc cagtgaatcc ccgcatttta tgcgttttca tgttgcctgc ccgcattgcg  1440
gggaggagca gtatcttaaa tttggcgaca agagacgcc gtttggcctc aaatggacgc  1500
cggatgaccc ctccagcgtg ttttatctct gcgagcataa tgcctgcgtc atccgccagc  1560
aggagctgga ctttactgat gcccgttata tctgcgaaaa gaccgggatc tggacccgtg  1620
atggcattct ctggttttcg tcatccggtg aagagattga gccacctgac agtgtgacct  1680
ttcacatctg gacagcgtac agcccgttca ccacctgggt gcagattgtc aaagactgga  1740
tgaaaacgaa aggggatacg ggaaaacgta aaaccttcgt aaacaccacg ctcggtgaga  1800
```

```
cgtgggaggc gaaaattggc gaacgtccgg atgctgaagt gatggcagag cggaaagagc    1860
attattcagc gcccgttcct gaccgtgtgg cttacctgac cgccggtatc gactcccagc    1920
tggaccgcta cgaaatgcgc gtatgggat ggggggccggg tgaggaaagc tggctgattg    1980
accggcagat tattatgggc cgccacgacg atgaacagac gctgctgcgt gtggatgagg    2040
ccatcaataa aacctatacc cgccggaatg gtgcagaaat gtcgatatcc cgtatctgct    2100
gggatactgg cgggattgac ccgaccattg tgtatgaacg ctcgaaaaaa catgggctgt    2160
tccgggtgat ccccattaaa ggggcatccg tctacggaaa gccggtggcc agcatgccac    2220
gtaagcgaaa caaaaacggg gtttaccttga ccgaaatcgg tacggatacc gcgaaagagc    2280
agatttataa ccgcttcaca ctgacgccgg aaggggatga accgcttccc ggtgccgttc    2340
acttcccgaa taacccggat attttttgatc tgaccgaagc gcagcagctg actgctgaag    2400
agcaggtcga aaaatgggtg gatggcagga aaaaaatact gtgggacagc aaaaagcgac    2460
gcaatgaggc actcgactgc ttcgtttatg cgctggcggc gctgcgcatc agtatttccc    2520
gctggcagct ggatctcagt gcgctgctgg cgagcctgca ggaagaggat ggtgcagcaa    2580
ccaacaagaa aacactggca gattacgccc gtgccttatc cggagaggat gaatgacgcg    2640
acaggaagaa cttgccgctg cccgtgcggc actgcatgac ctgatgacag gtaaacgggt    2700
ggcaacagta cagaaagacg gacgaagggt ggagtttacg gccacttccg tgtctgacct    2760
gaaaaaatat attgcagagc tggaagtgca gaccggcatg acacagcgac gcaggggacc    2820
tgcaggattt tatgtatgaa aacgcccacc attcccaccc ttctggggcc ggacggcatg    2880
acatcgctgc gcgaatatgc cggttatcac ggcggtggca gcggatttgg agggcagttg    2940
cggtcgtgga acccaccgag tgaaagtgtg gatgcagccc tgttgcccaa ctttacccgt    3000
ggcaatgccc gcgcagacga tctggtacgc aataacggct atgccgccaa cgccatccag    3060
ctgcatcagg atcatatcgt cgggtctttt ttccggctca gtcatcgccc aagctggcgc    3120
tatctgggca tcggggagga agaagcccgt gccttttccc gcgaggttga agcggcatgg    3180
aaagagtttg ccgaggatga ctgctgctgc attgacgttg agcgaaaacg cacgtttacc    3240
atgatgattc gggaaggtgt ggccatgcac gcctttaacg gtgaactgtt cgttcaggcc    3300
acctgggata ccagttcgtc gcggcttttc cggacacagt tccggatggt cagcccgaag    3360
cgcatcagca acccgaacaa taccggcgac agccggaact gccgtgccgg tgtgcagatt    3420
aatgacagcg gtgcggcgct gggatattac gtcagcgagg acgggtatcc tggctggatg    3480
ccgcagaaat ggacatggat accccgtgag ttacccggcg ggcgcgcctc gttcattcac    3540
gtttttgaac ccgtggagga cgggcagact cgcggtgcaa atgtgtttta cagcgtgatg    3600
gagcagatga agatgctcga cacgctgcag aacacgcagc tgcagagcgc cattgtgaag    3660
gcgatgtatg ccgccaccat tgagagtgag ctggatacgc agtcagcgat ggatttatt     3720 ctgggcgcga acagtcagga gcagcgggaa aggctgaccg gctggattgg tgaaattgcc    3780
gcgtattacg ccgcagcgcc ggtccggctg ggaggcgcaa aagtaccgca cctgatgccg    3840
ggtgactcac tgaacctgca gacggctcag gatacggata acggctactc cgtgtttgag    3900
cagtcactgc tgcggtatat cgctgccggg ctgggtgtct cgtatgagca gctttcccgg    3960
aattacgccc agatgagcta ctccacggca cgggccagtg cgaacgagtc gtgggcgtac    4020 tttatgggc ggcgaaaatt cgtcgcatcc cgtcaggcga gccagatgtt tctgtgctgg    4080
ctggaagagg ccatcgttcg ccgcgtggtg acgttacctt caaaagcgcg cttcagtttt    4140
```

```
caggaagccc gcagtgcctg ggggaactgc gactggatag gctccggtcg tatggccatc    4200
gatggtctga aagaagttca ggaagcggtg atgctgatag aagccggact gagtacctac    4260
gagaaagagt gcgcaaaacg cggtgacgac tatcaggaaa tttttgccca gcaggtccgt    4320
gaaacgatgg agcgccgtgc agccggtctt aaaccgcccg cctgggcggc tgcagcattt    4380
gaatccgggc tgcgacaatc aacagaggag gagaagagtg acagcagagc tgcgtaatct    4440
cccgcatatt gccagcatgg cctttaatga gccgctgatg cttgaacccg cctatgcgcg    4500
ggttttcttt tgtgcgcttg caggccagct tgggatcagc agcctgacgg atgcggtgtc    4560
cggcgacagc ctgactgccc aggaggcact cgcgacgctg gcattatccg gtgatgatga    4620
cggaccacga caggcccgca gttatcaggt catgaacggc atcgccgtgc tgccggtgtc    4680
cggcacgctg gtcagccgga cgcgggcgct gcagccgtac tcggggatga ccggttacaa    4740
cggcattatc gcccgtctgc aacaggctgc cagcgatccg atggtggacg gcattctgct    4800
cgatatggac acgcccggcg ggatggtggc ggggcatttt gactgcgctg acatcatcgc    4860
ccgtgtgcgt gacataaaac cggtatgggc gcttgccaac gacatgaact gcagtgcagg    4920
tcagttgctt gccagtgccg cctcccggcg tctggtcacg cagaccgccc ggacaggctc    4980
catcggcgtc atgatggctc acagtaatta cggtgctgcg ctggagaaac agggtgtgga    5040
aatcacgctg atttacagcg gcagccataa ggtggatggc aaccctaca gccatcttcc    5100 ggatgacgtc cgggagacac tgcagtcccg gatggacgca acccgccaga tgtttgcgca    5160
gaaggtgtcg gcataccg gcctgtccgt gcaggttgtg ctggataccg aggctgcagt    5220
gtacagcggt caggaggcca ttgatgccgg actggctgat gaacttgtta acagcaccga    5280
tgcgatcacc gtcatgcgtg atgcactgga tgcacgtaaa tcccgtctct caggagggcg    5340
aatgaccaaa gagactcaat caacaactgt ttcagccact gcttcgcagg ctgacgttac    5400
tgacgtggtg ccagcgacgg agggcgagaa cgccagcgcg gcgcagccgg acgtgaacgc    5460
gcagatcacc gcagcggttg cggcagaaaa cagccgcatt atggggatcc tcaactgtga    5520
ggaggctcac ggacgcgaag aacaggcacg cgtgctggca gaaaccccg gtatgaccgt    5580 gaaaacggcc cgccgcattc tggccgcagc accacagagt gcacaggcgc gcagtgacac    5640
tgcgctggat cgtctgatgc aggggcacc ggcaccgctg gctgcaggta acccggcatc    5700
tgatgccgtt aacgatttgc tgaacacacc agtgtaaggg atgtttatga cgagcaaaga    5760
aacctttacc cattaccagc cgcagggcaa cagtgacccg gctcataccg caaccgcgcc    5820
cggcggattg agtgcgaaag cgcctgcaat gaccccgctg atgctggaca cctccagccg    5880
taagctggtt gcgtgggatg caccaccga cggtgctgcc gttggcattc ttgcggttgc    5940
tgctgaccag accagcacca cgctgacgtt ctacaagtcc ggcacgttcc gttatgagga    6000
tgtgctctgg ccggaggctg ccagcgacga gacgaaaaaa cggaccgcgt tgccggaac    6060 ggcaatcagc atcgtttaac tttacccttc atcactaaag gccgcctgtg cggcttttt    6120 tacgggattt tttatgtcg atgtacacaa ccgcccaact gctggcggca aatgagcaga    6180
aatttaagtt tgatccgctg tttctgcgtc tcttttttccg tgagagctat cccttcacca    6240
cggagaaagt ctatctctca caaattccgg gactggtaaa catggcgctg tacgtttcgc    6300
cgattgtttc cggtgaggtt atccgttccc gtggcggctc cacctctgaa tttacgccgg    6360
gatatgtcaa gccgaagcat gaagtgaatc cgcagatgac cctgcgtcgc ctgccggatg    6420
aagatccgca gaatctggcg gacccggctt accgccgccg tcgcatcatc atgcagaaca    6480
tgcgtgacga agagctggcc attgctcagg tcgaagagat gcaggcagtt tctgccgtgc    6540
```

```
ttaagggcaa atacaccatg accggtgaag ccttcgatcc ggttgaggtg gatatgggcc    6600
gcagtgagga gaataacatc acgcagtccg gcggcacgga gtggagcaag cgtgacaagt    6660
ccacgtatga cccgaccgac gatatcgaag cctacgcgct gaacgccagc ggtgtggtga    6720
atatcatcgt gttcgatccg aaaggctggg cgctgttccg ttccttcaaa gccgtcaagg    6780
agaagctgga tacccgtcgt ggctctaatt ccgagctgga gacagcggtg aaagacctgg    6840
gcaaagcggt gtcctataag gggatgtatg gcgatgtggc catcgtcgtg tattccggac    6900
agtacgtgga aaacggcgtc aaaaagaact cctgccggga caacacgatg gtgctgggga    6960
acactcaggc acgcggtctg cgcacctatg gctgcattca ggatgcggac gcacagcgcg    7020
aaggcattaa cgcctctgcc cgttacccga aaaactgggt gaccaccggc gatccggcgc    7080
gtgagttcac catgattcag tcagcaccgc tgatgctgct ggctgaccct gatgagttcg    7140
tgtccgtaca actggcgtaa tcatggccct tcggggccat tgtttctctg tggaggagtc    7200
catgacgaaa gatgaactga ttgcccgtct ccgctcgctg ggtgaacaac tgaaccgtga    7260
tgtcagcctg acggggacga agaagaact ggcgctccgt gtggcagagc tgaaagagga    7320
gcttgatgac acgatgaaa ctgccggtca ggacacccct ctcagccggg aaaatgtgct    7380
gaccggacat gaaaatgagg tgggatcagc gcagccggat accgtgattc tggatacgtc    7440
tgaactggtc acggtcgtgg cactggtgaa gctgcatact gatgcacttc acgccacgcg    7500
ggatgaacct gtggcatttg tgctgccggg aacggcgttt cgtgtctctg ccggtgtggc    7560
agccgaaatg acagagcgcg gcctggccag aatgcaataa cgggaggcgc tgtggctgat    7620
ttcgataacc tgttcgatgc tgccattgcc cgcgccgatg aaacgatacg cgggtacatg    7680
ggaacgtcag ccaccattac atccggtgag cagtcaggtg cggtgatacg tggtgttttt    7740
gatgaccctg aaaatatcag ctatgccgga cagggcgtgc gcgttgaagg ctccagcccg    7800
tccctgtttg tccggactga tgaggtgcgc cagctgcggc gtggagacac gctgaccatc    7860
ggtgaggaaa atttctgggt agatcgggtt tcgccggatg atggcggaag ttgtcatctc    7920
tggcttggac ggggcgtacc gcctgccgtt aaccgtcgcc gctgaaaggg ggatgtatgg    7980
ccataaaagg tcttgagcag gccgttgaaa acctcagccg tatcagcaaa acggcggtgc    8040
ctggtgccgc cgcaatggcc attaaccgcg ttgcttcatc cgcgatatcg cagtcggcgt    8100
cacaggttgc ccgtgagaca aaggtacgcc ggaaactggt aaaggaaagg gccaggctga    8160
aaagggccac ggtcaaaaat ccgcaggcca gaatcaaagt taaccggggg gatttgcccg    8220
taatcaagct gggtaatgcg cggggttgtcc tttcgcgccg caggcgtcgt aaaaaggggc    8280
agcgttcatc cctgaaaggt ggcggcagcg tgcttgtggt gggtaaccgt cgtattcccg    8340
gcgcgtttat tcagcaactg aaaaatggcc ggtggcatgt catgcagcgt gtggctggga    8400
aaaccgtta ccccattgat gtggtgaaaa tcccgatggc ggtgccgctg accacggcgt    8460
ttaaacaaaa tattgagcgg atacggcgtg aacgtcttcc gaaagagctg gctatgcgc    8520
tgcagcatca actgaggatg gtaataaagc gatgaaacat actgaactcc gtgcagccgt    8580
actggatgca ctggagaagc atgacaccgg ggcgacgttt tttgatggtc gccccgctgt    8640
ttttgatgag gcggattttc cggcagttgc cgtttatctc accggcgctg aatacacggg    8700
cgaagagctg gacagcgata cctggcaggc ggagctgcat atcgaagttt tcctgcctgc    8760
tcaggtgccg gattcagagc tggatgcgtg gatggagtcc cggatttatc cggtgatgag    8820
cgatatcccg gcactgtcag atttgatcac cagtatggtg gccagcggct atgactaccg    8880
```

```
gcgcgacgat gatgcgggct tgtggagttc agccgatctg acttatgtca ttacctatga   8940
aatgtgagga cgctatgcct gtaccaaatc ctacaatgcc ggtgaaaggt gccgggacca   9000
ccctgtgggt ttataagggg agcggtgacc cttacgcgaa tccgctttca gacgttgact   9060
ggtcgcgtct ggcaaaagtt aaagacctga cgcccggcga actgaccgct gagtcctatg   9120
acgacagcta tctcgatgat gaagatgcag actggactgc gaccgggcag ggcagaaat   9180 ctgccggaga taccagcttc acgctggcgt ggatgcccgg agagcagggg cagcaggcgc   9240
tgctggcgtg gtttaatgaa ggcgataccc gtgcctataa aatccgcttc ccgaacggca   9300
cggtcgatgt gttccgtggc tgggtcagca gtatcggtaa ggcggtgacg gcgaaggaag   9360
tgatcacccg cacggtgaaa gtcaccaatg tgggacgtcc gtcgatggca gaagatcgca   9420
gcacggtaac agcggcaacc ggcatgaccg tgacgcctgc cagcacctcg gtggtgaaag   9480
ggcagagcac cacgctgacc gtggccttcc agccggaggg cgtaaccgac aagagctttc   9540
gtgcggtgtc tgcggataaa acaaaagcca ccgtgtcggt cagtggtatg accatcaccg   9600
tgaacggcgt tgctgcaggc aaggtcaaca ttccggttgt atccggtaat ggtgagtttg   9660
ctgcggttgc agaaattacc gtcaccgcca gttaatccgg agagtcagcg atgttcctga   9720
aaaccgaatc atttgaacat aacggtgtga ccgtcacgcg ttctgaactg tcagccctgc   9780
agcgcattga gcatctcgcc ctgatgaaac ggcaggcaga acaggcggag tcagacagca   9840
accggaagtt tactgtggaa gacgccatca gaaccggcgc gtttctggtg gcgatgtccc   9900
tgtggcataa ccatccgcag aagacgcaga tgccgtccat gaatgaagcc gttaaacaga   9960
ttgagcagga agtgcttacc acctggccca cggaggcaat ttctcatgct gaaaacgtgg  10020
tgtaccggct gtctggtatg tatgagtttg tggtgaataa tgcccctgaa cagacagagg  10080
acgccgggcc cgcagagcct gtttctgcgg gaaagtgttc gacggtgagc tgagttttgc  10140
cctgaaactg gcgcgtgaga tggggcgacc cgactggcgt gccatgcttg ccgggatgtc  10200
atccacggag tatgccgact ggcaccgcctt ttacagtacc cattattttc atgatgttct  10260
gctggatatg cactttttccg ggctgacgta caccgtgctc agcctgtttt tcagcgatcc  10320
ggatatgcat ccgctggatt tcagtctgct gaaccggcgc gaggctgacg aagagcctga  10380
agatgatgtg ctgatgcaga aagcggcagg gcttgccgga ggtgtccgct ttggcccgga  10440
cgggaatgaa gttatccccg cttccccgga tgtggcggac atgacggagg atgacgtaat  10500
gctgatgaca gtatcagaag ggatcgcagg aggagtccgg tatggctgaa ccggtaggcg  10560
atctggtcgt tgatttgagt ctggatgcgg ccagatttga cgagcagatg gccagagtca  10620
ggcgtcattt ttctggtacg gaaagtgatg cgaaaaaaac agcggcagtc gttgaacagt  10680
cgctgagccg acaggcgctg gctgcacaga aagcggggat ttccgtcggg cagtataaag  10740
ccgccatgcg tatgctgcct gcacagttca ccgacgtggc cacgcagctt gcaggcgggc  10800
aaagtccgtg gctgatcctg ctgcaacagg ggggcaggt gaaggactcc ttcggcggga  10860
tgatccccat gttcaggggg cttgccggtg cgatcaccct gccgatggtg ggggccacct  10920
cgctggcggt ggcgaccggt gcgctggcgt atgcctggta tcagggcaac tcaaccctgt  10980
ccgatttcaa caaaacgctg gtccttttccg gcaatcaggc gggactgacg gcagatcgta  11040
tgctggtcct gtccagagcc gggcaggcgg cagggctgac gtttaaccag accagcgagt  11100
cactcagcgc actggttaag gcgggggtaa gcggtgaggc tcagattgcg tccatcagcc  11160
agagtgtggc gcgtttctcc tctgcatccg gcgtggaggt ggacaaggtc gctgaagcct  11220
tcgggaagct gaccacagac ccgacgtcgg ggctgacggc gatggctcgc cagttccata  11280
```

```
acgtgtcggc ggagcagatt gcgtatgttg ctcagttgca gcgttccggc gatgaagccg    11340
gggcattgca ggcggcgaac gaggccgcaa cgaaagggtt tgatgaccag acccgccgcc    11400
tgaaagagaa catgggcacg ctggagacct gggcagacag gactgcgcgg gcattcaaat    11460
ccatgtggga tgcggtgctg atattggtc gtcctgatac cgcgcaggag atgctgatta    11520
aggcagaggc tgcgtataag aaagcagacg acatctggaa tctgcgcaag gatgattatt    11580
ttgttaacga tgaagcgcgg gcgcgttact gggatgatcg tgaaaaggcc cgtcttgcgc    11640
ttgaagccgc ccgaaagaag gctgagcagc agactcaaca ggacaaaaat gcgcagcagc    11700
agagcgatac cgaagcgtca cggctgaaat ataccgaaga ggcgcagaag gcttacgaac    11760
ggctgcagac gccgctggag aaatataccg cccgtcagga agaactgaac aaggcactga    11820
aagacgggaa aatcctgcag gcggattaca acacgctgat ggcggcggcg aaaaaggatt    11880
atgaagcgac gctgaaaaag ccgaaacagt ccagcgtgaa ggtgtctgcg ggcgatcgtc    11940
aggaagacag tgctcatgct gccctgctga cgcttcaggc agaactccgg acgctggaga    12000
agcatgccgg agcaaatgag aaaatcagcc agcagcgccg ggatttgtgg aaggcggaga    12060
gtcagttcgc ggtactggag gaggcggcgc aacgtcgcca gctgtctgca caggagaaat    12120
ccctgctggc gcataaagat gagacgctgg agtacaaacg ccagctggct gcacttggcg    12180
acaaggttac gtatcaggag cgcctgaacg cgctggcgca gcaggcggat aaattcgcac    12240
agcagcaacg ggcaaaacgg gccgccattg atgcgaaaag ccgggggctg actgaccggc    12300
aggcagaacg ggaagccacg gaacagcgcc tgaaggaaca gtatggcgat aatccgctgg    12360
cgctgaataa cgtcatgtca gagcagaaaa agacctgggc ggctgaagac cagcttcgcg    12420
ggaactggat ggcaggcctg aagtccggct ggagtgagtg ggaagagagc gccacggaca    12480
gtatgtcgca ggtaaaaagt gcagccacgc agacctttga tggtattgca cagaatatgg    12540
cggcgatgct gaccggcagt gagcagaact ggcgcagctt cacccgttcc gtgctgtcca    12600
tgatgacaga aattctgctt aagcaggcaa tggtggggat tgtcgggagt atcggcagcg    12660
ccattggcgg ggctgttggt ggcggcgcat ccgcgtcagg cggtacagcc attcaggccg    12720
ctgcggcgaa attccatttt gcaaccggag gatttacggg aaccggcggc aaatatgagc    12780
cagcggggat tgttcaccgt ggtgagtttg tcttcacgaa ggaggcaacc agccggattg    12840
gcgtggggaa tctttaccgg ctgatgcgcg gctatgccac cggcggttat gtcggtacac    12900
cgggcagcat ggcagacagc cggtcgcagg cgtccgggac gtttgagcag aataaccatg    12960
tggtgattaa caacgacggc acgaacgggc agataggtcc ggctgctctg aaggcggtgt    13020
atgacatggc ccgcaagggt gcccgtgatg aaattcagac acagatgcgt gatggtggcc    13080
tgttctccgg aggtggacga tgaagacctt ccgctgaaa gtgaacccg gtatggatgt    13140 ggcttcggtc ccttctgtaa gaaaggtgcg ctttggtgat ggctattctc agcgagcgcc    13200
tgccgggctg aatgccaacc tgaaaacgta cagcgtgacg cttctgtcc cccgtgagga    13260 ggccacggta ctggagtcgt ttctggaaga gcacgggggc tggaaatcct ttctgtggac    13320
gccgccttat gagtggcggc agataaaggt gacctgcgca aaatggtcgt cgcgggtcag    13380
tatgctgcgt gttgagttca gcgcagagtt tgaacaggtg gtgaactgat gcaggatatc    13440
cggcaggaaa cactgaatga atgcacccgt gcggagcagt cggccagcgt ggtgctctgg    13500
gaaatcgacc tgacagaggt cggtggagaa cgttattttt tctgtaatga gcagaacgaa    13560
aaaggtgagc cggtcacctg gcaggggcga cagtatcagc cgtatcccat tcaggggagc    13620
```

```
ggttttgaac tgaatggcaa aggcaccagt acgcgcccca cgctgacggt ttctaacctg   13680
tacggtatgg tcaccgggat ggcggaagat atgcagagtc tggtcggcgg aacggtggtc   13740
cggcgtaagg tttacgcccg ttttctggat gcggtgaact tcgtcaacgg aaacagttac   13800
gccgatccgg agcaggaggt gatcagccgc tggcgcattg agcagtgcag cgaactgagc   13860
gcggtgagtg cctcctttgt actgtccacg ccgacggaaa cggatggcgc tgttttccg   13920 ggacgtatca tgctggccaa cacctgcacc tggacctatc gcggtgacga gtgcggttat   13980
agcggtccgg ctgtcgcgga tgaatatgac cagccaacgt ccgatatcac gaaggataaa   14040
tgcagcaaat gcctgagcgg ttgtaagttc cgcaataacg tcggcaactt tggcggcttc   14100
ctttccatta acaaactttc gcagtaaatc ccatgacaca gacagaatca gcgattctgg   14160
cgcacgcccg gcgatgtgcg ccagcggagt cgtgcggctt cgtggtaagc acgccggagg   14220
gggaaagata tttcccctgc gtgaatatct ccggtgagcc ggaggctatt tccgtatgtc   14280
gccggaagac tggctgcagg cagaaatgca gggtgagatt gtggcgctgg tccacagcca   14340
ccccggtggt ctgccctggc tgagtgaggc cgaccggcgg ctgcaggtgc agagtgattt   14400
gccgtggtgg ctggtctgcc ggggacgat tcataagttc cgctgtgtgc cgcatctcac   14460
cgggcggcgc tttgagcacg gtgtgacgga ctgttacaca ctgttccggg atgcttatca   14520
tctggcgggg attgagatgc cggactttca tcgtgaggat gactggtggc gtaacggcca   14580
gaatctctat ctggataatc tggaggcgac ggggctgtat caggtgccgt tgtcagcggc   14640
acagccgggc gatgtgctgc tgtgctgttt tggttcatca gtgccgaatc acgccgcaat   14700
ttactgcggc gacggcgagc tgctgcacca tattcctgaa caactgagca acgagagag   14760 gtacaccgac aaatggcagc gacgcacaca ctccctctgg cgtcaccggg catggcgcgc   14820
atctgccttt acgggatttt acaacgattt ggtcgccgca tcgaccttcg tgtgaaaacg   14880
ggggctgaag ccatccgggc actggccaca cagctcccgg cgtttcgtca gaaactgagc   14940
gacggctggt atcaggtacg gattgccggg cgggacgtca gcacgtccgg gttaacggcg   15000
cagttacatg agactctgcc tgatggcgct gtaattcata ttgttcccag agtcgccggg   15060
gccaagtcag gtgcgtatt ccagattgtc ctggggggctg ccgccattgc cggatcattc   15120
tttaccgccg gagccaccct tgcagcatgg ggggcagcca ttggggccgg tggtatgacc   15180
ggcatcctgt tttctctcgg tgccagtatg gtgctcggtg gtgtgcgca gatgctggca   15240 ccgaaagcca gaactccccg tatacagaca acggataacg gtaagcagaa cacctatttc   15300
tcctcactgg ataacatggt tgcccagggc aatgttctgc ctgttctgta cggggaaatg   15360
cgcgtggggt cacgcgtggt ttctcaggag atcagcacgg cagacgaagg ggacggtggt   15420
caggttgtgg tgattggtcg ctgatgcaaa atgttttatg tgaaaccgcc tgcgggcggt   15480
tttgtcattt atggagcgtg aggaatgggt aaaggaagca gtaagggca taccccgcgc   15540 gaagcgaagg acaacctgaa gtccacgcag ttgctgagtg tgatcgatgc catcagcgaa   15600
gggccgattg aaggtccggt ggatggctta aaaagcgtgc tgctgaacag tacgccggtg   15660
ctggacactg aggggaatac caacatatcc ggtgtcacgg tggtgttccg ggctggtgag   15720
caggagcaga ctccgccgga gggatttgaa tcctccggct ccgagacggt gctgggtacg   15780
gaagtgaaat atgacacgcc gatcacccgc accattacgt ctgcaaacat cgaccgtctg   15840
cgctttacct tcggtgtaca ggcactggtg gaaaccacct caaagggtga caggaatccg   15900
tcggaagtcc gcctgctggt tcagatacaa cgtaacggtg gctgggtgac ggaaaaagac   15960
atcaccatta agggcaaaac cacctcgcag tatctggcct cggtggtgat gggtaacctg   16020
```

```
ccgccgcgcc cgtttaatat ccggatgcgc aggatgacgc cggacagcac cacagaccag   16080
ctgcagaaca aaacgctctg gtcgtcatac actgaaatca tcgatgtgaa acagtgctac   16140
ccgaacacgg cactggtcgg cgtgcaggtg gactcggagc agttcggcag ccagcaggtg   16200
agccgtaatt atcatctgcg cgggcgtatt ctgcaggtgc cgtcgaacta taacccgcag   16260
acgcggcaat acagcggtat ctgggacgga acgtttaaac cggcatacag caacaacatg   16320
gcctggtgtc tgtgggatat gctgacccat ccgcgctacg gcatgggaa acgtcttggt    16380 gcggcggatg tggataaatg ggcgctgtat gtcatcggcc agtactgcga ccagtcagtg   16440
ccggacggct ttggcggcac ggagccgcgc atcacctgta atgcgtacct gaccacacag   16500
cgtaaggcgt gggatgtgct cagcgatttc tgctcggcga tgcgctgtat gccggtatgg   16560
aacgggcaga cgctgacgtt cgtgcaggac cgaccgtcgg ataagacgtg gacctataac   16620
cgcagtaatg tggtgatgcc ggatgatggc gcgccgttcc gctacagctt cagcgccctg   16680
aaggaccgcc ataatgccgt tgaggtgaac tggattgacc cgaacaacgg ctgggagacg   16740
gcgacagagc ttgttgaaga tacgcaggcc attgcccgtt acggtcgtaa tgttacgaag   16800
atggatgcct ttggctgtac cagccggggg caggcacacc gcgccgggct gtggctgatt   16860
aaaacagaac tgctggaaac gcagaccgtg gatttcagcg tcggcgcaga agggcttcgc   16920
catgtaccgg gcgatgttat tgaaatctgc gatgatgact atgccggtat cagcaccggt   16980
ggtcgtgtgc tggcggtgaa cagccagacc cggacgctga cgctcgaccg tgaaatcacg   17040
ctgccatcct ccggtaccgc gctgataagc ctggttgacg gaagtggcaa tccggtcagc   17100
gtggaggttc agtccgtcac cgacggcgtg aaggtaaaag tgagccgtgt tcctgacggt   17160
gttgctgaat acagcgtatg ggagctgaag ctgccgacgc tgcgccagcg actgttccgc   17220
tgcgtgagta tccgtgagaa cgacgacggc acgtatgcca tcaccgccgt gcagcatgtg   17280
ccggaaaaag aggccatcgt ggataacggg gcgcactttg acggcgaaca gagtggcacg   17340
gtgaatggtg tcacgccgcc agcggtgcag cacctgaccg cagaagtcac tgcagacagc   17400
ggggaatatc aggtgctggc gcgatgggac acaccgaagg tggtgaaggg cgtgagtttc   17460
ctgctccgtc tgaccgtaac agcggacgac ggcagtgagc ggctggtcag cacggcccgg   17520
acgacggaaa ccacataccg cttcacgcaa ctggcgctgg gaactacag gctgacagtc    17580 cgggcggtaa atgcgtgggg gcagcagggc gatccgcgt cggtatcgtt ccggattgcc     17640
gcaccggcag caccgtcgag gattgagctg acgccgggct attttcagat aaccgccacg   17700
ccgcatcttg ccgtttatga cccgacggta cagtttgagt tctggttctc ggaaaagcag   17760
attgcggata tcagacaggt tgaaaccagc acgcgttatc ttggtacggc gctgtactgg   17820
atagccgcca gtatcaatat caaaccgggc catgattatt acttttatat ccgcagtgtg   17880
aacaccgttg gcaaatcggc attcgtggag gccgtcggtc gggcgagcga tgatgcggaa   17940
ggttacctgg attttttcaa aggcaagata accgaatccc atctcggcaa ggagctgctg   18000
gaaaaagtcg agctgacgga ggataacgcc agcagactgg aggagttttc gaaagagtgg   18060
aaggatgcca gtgataagtg gaatgccatg tgggctgtca aaattgagca gaccaaagac   18120
ggcaaacatt atgtcgcggg tattggcctc agcatggagg acacggagga aggcaaactg   18180
agccagtttc tggttgccgc caatcgtatc gcatttattg acccggcaaa cgggaatgaa   18240
acgccgatgt ttgtggcgca gggcaaccag atattcatga acgacgtgtt cctgaagcgc   18300
ctgacggccc ccaccattac cagcggcggc aatcctccgg ccttttccct gacaccggac   18360
```

-continued

```
ggaaagctga ccgctaaaaa tgcggatatc agtggcagtg tgaatgcgaa ctccgggacg    18420
ctcagtaatg tgacgatagc tgaaaactgt acgataaacg gtacgctgag ggcggaaaaa    18480
atcgtcgggg acattgtaaa ggcggcgagc gcggcttttc cgcgccagcg tgaaagcagt    18540
gtggactggc cgtcaggtac ccgtactgtc accgtgaccg atgaccatcc ttttgatcgc    18600
cagatagtgg tgcttccgct gacgtttcgc ggaagtaagc gtactgtcag cggcaggaca    18660
acgtattcga tgtgttatct gaaagtactg atgaacggtg cggtgattta tgatggcgcg    18720
gcgaacgagg cggtacaggt gttctcccgt attgttgaca tgccagcggg tcgggaaac    18780 gtgatcctga cgttcacgct tacgtccaca cggcattcgg cagatattcc gccgtatacg    18840
tttgccagcg atgtgcaggt tatggtgatt aagaaacagg cgctgggcat cagcgtggtc    18900
tgagtgtgtt acagaggttc gtccgggaac gggcgtttta ttataaaaca gtgagaggtg    18960
aacgatgcgt aatgtgtgta ttgccgttgc tgtctttgcc gcacttgcgg tgacagtcac    19020
tccggcccgt gcggaaggtg gacatggtac gtttacggtg ggctattttc aagtgaaacc    19080
gggtacattg ccgtcgttgt cgggcgggga taccggtgtg agtcatctga aagggattaa    19140
cgtgaagtac cgttatgagc tgacggacag tgtgggggtg atggcttccc tggggttcgc    19200
cgcgtcgaaa aagagcagca cagtgatgac cggggaggat acgtttcact atgagagcct    19260
gcgtggacgt tatgtgagcg tgatggccgg accggttta caaatcagta agcaggtcag    19320
tgcgtacgcc atgccggag tggctcacag tcggtggtcc ggcagtacaa tggattaccg    19380
taagacggaa atcactcccg ggtatatgaa agagacgacc actgccaggg acgaaagtgc    19440
aatgcggcat acctcagtgg cgtggagtgc aggtatacag attaatccgg cagcgtccgt    19500
cgttgttgat attgcttatg aaggctccgg cagtggcgac tggcgtactg acggattcat    19560
cgttggggtc ggttataaat tctgattagc caggtaacac agtgttatga cagcccgccg    19620
gaaccggtgg gctttttgt ggggtgaata tggcagtaaa gatttcagga gtcctgaaag    19680
acggcacagg aaaaccggta cagaactgca ccattcagct gaaagccaga cgtaacagca    19740
ccacggtggt ggtgaacacg gtgggctcag agaatccgga tgaagccggg cgttacagca    19800
tggatgtgga gtacggtcag tacagtgtca tcctgcaggt tgacggtttt ccaccatcgc    19860
acgccgggac catcaccgtg tatgaagatt cacaaccggg gacgctgaat gattttctct    19920
gtgccatgac ggaggatgat gcccggccgg aggtgctgcg tcgtcttgaa ctgatggtgg    19980
aagaggtggc gcgtaacgcg tccgtggtgg cacagagtac ggcagacgcg aagaaatcag    20040
ccggcgatgc cagtgcatca gctgctcagg tcgcggccct tgtgactgat gcaactgact    20100
cagcacgcgc cgccagcacg tccgccggac aggctgcatc gtcagctcag gaagcgtcct    20160
ccggcgcaga gcggcatca gcaaaggcca ctgaagcgga aaaagtgcc gcagccgcag    20220 agtcctcaaa aaacgcggcg gccaccagtg ccggtgcggc gaaaacgtca gaaacgaatg    20280
ctgcagcgtc acaacaatca gccgccacgt ctgcctccac cgcggccacg aaagcgtcag    20340
aggccgccac ttcagcacga gatgcggtgg cctcaaaaga ggcagcaaaa tcatcagaaa    20400
cgaacgcatc atcaagtgcc ggtcgtgcag cttcctcggc aacggcggca gaaaattctg    20460 ccagggcgg aaaaacgtcc gagacgaatg ccaggtcatc tgaaacagca gcggaacgga    20520
gcgcctctgc cgcggcagac gcaaaaacag cggcggcggg gagtgcgtca acggcatcca    20580
cgaaggcgac agaggctgcg ggaagtgcg tatcagcatc gcagagcaaa agtgcggcag    20640
aagcggcggc aatacgtgca aaaaattcgg caaaacgtgc agaagatata gcttcagctg    20700
tcgcgcttga ggatgcggac acaacgagaa aggggatagt gcagctcagc agtgcaacca    20760
```

```
acagcacgtc tgaaacgctt gctgcaacgc caaaggcggt taaggtggta atggatgaaa   20820
cgaacagaaa agcccactgg acagtccggc actgaccgga acgccaacag caccaaccgc   20880
gctcagggga acaaacaata cccagattgc gaacaccgct tttgtactgg ccgcgattgc   20940
agatgttatc gacgcgtcac ctgacgcact gaatacgctg aatgaactgg ccgcagcgct   21000
cgggaatgat ccagattttg ctaccaccat gactaacgcg cttgcgggta acaaccgaa   21060 gaatgcgaca ctgacggcgc tggcagggct ttccacggcg aaaataaat taccgtattt   21120 tgcggaaaat gatgccgcca gcctgactga actgactcag gttggcaggg atattctggc   21180
aaaaaattcc gttgcagatg ttcttgaata ccttggggcc ggtgagaatt cggccttttcc  21240 ggcaggtgcg ccgatcccgt ggccatcaga tatcgttccg tctggctacg tcctgatgca   21300
ggggcaggcg tttgacaaat cagcctaccc aaaacttgct gtcgcgtatc catcgggtgt   21360
gcttcctgat atgcgaggct ggacaatcaa ggggaaaccc gccagcggtc gtgctgtatt   21420
gtctcaggaa caggatggaa ttaagtcgca cacccacagt gccagtgcat ccggtacgga   21480
tttggggacg aaaaccacat cgtcgtttga ttacgggacg aaaacaacag gcagtttcga   21540
ttacggcacc aaatcgacga ataacacggg ggctcatgct cacagtctga gcggttcaac   21600
aggggccgcg ggtgctcatg cccacacaag tggtttaagg atgaacagtt ctggctggag   21660
tcagtatgga acagcaacca ttacaggaag tttatccaca gttaaaggaa ccagcacaca   21720
gggtattgct tatttatcga aaacggacag tcagggcagc cacagtcact cattgtccgg   21780
tacagccgtg agtgccggtg cacatgcgca tacagttggt attggtgcgc accagcatcc   21840
ggttgttatc ggtgctcatg cccattcttt cagtattggt tcacacggac acaccatcac   21900
cgttaacgct gcgggtaacg cggaaaaacac cgtcaaaaac attgcattta actatattgt   21960
gaggcttgca taatggcatt cagaatgagt gaacaaccac ggaccataaa aatttataat   22020
ctgctggccg gaactaatga atttattggt gaaggtgacg catatattcc gcctcatacc   22080
ggtctgcctg caaacagtac cgatattgca ccgccagata ttccggctgg ctttgtggct   22140 gtttttcaaca gtgatgaggc atcgtggcat ctcgttgaag accatcgggg taaaaccgtc   22200
tatgacgtgg cttccggcga cgcgttattt atttctgaac tcggtccgtt accggaaaat   22260
tttacctggt tatcgccggg aggggaatat cagaagtgga acggcacagc ctgggtgaag   22320
gatacggaag cagaaaaact gttccggatc cgggaggcgg aagaaacaaa aaaaagcctg   22380
atgcaggtag ccagtgagca tattgcgccg cttcaggatg ctgcagatct ggaaattgca   22440
acgaaggaag aaacctcgtt gctggaagcc tggaagaagt atcgggtgtt gctgaaccgt   22500
gttgatacat caactgcacc tgatattgag tggcctgctg tccctgttat ggagtaatcg   22560
ttttgtgata tgccgcagaa acgttgtatg aaataacgtt ctgcggttag ttagtatatt   22620
gtaaagctga gtattggttt atttggcgat tattatcttc aggagaataa tggaagttct   22680
atgactcaat tgttcatagt gtttacatca ccgccaattg cttttaagac tgaacgcatg   22740
aaatatggtt tttcgtcatg ttttgagtct gctgttgata tttctaaagt cggttttttt   22800 tcttcgttttt ctctaactat tttccatgaa atacattttt gattattatt tgaatcaatt   22860
ccaattacct gaagtctttc atctataatt ggcattgtat gtattggttt attggagtag   22920
atgcttgctt ttctgagcca tagctctgat atccaaatga agccataggc atttgttatt   22980
ttggctctgt cagctgcata acgccaaaaa atatatttat ctgcttgatc ttcaaatgtt   23040
gtattgatta aatcaattgg atggaattgt ttatcataaa aaattaatgt ttgaatgtga   23100
```

```
taaccgtcct ttaaaaaagt cgtttctgca agcttggctg tatagtcaac taactcttct    23160
gtcgaagtga tattttttagg cttatctacc agttttagac gctctttaat atcttcagga    23220
attattttat tgtcatattg tatcatgcta aatgacaatt tgcttatgga gtaatctttt    23280
aattttaaat aagttattct cctggcttca tcaaataaag agtcgaatga tgttggcgaa    23340
atcacatcgt cacccattgg attgtttatt tgtatgccaa gagagttaca gcagttatac    23400
attctgccat agattatagc taaggcatgt aataattcgt aatcttttag cgtattagcg    23460
acccatcgtc tttctgattt aataatagat gattcagtta aatatgaagg taatttcttt    23520
tgtgcaagtc tgactaactt ttttatacca atgtttaaca tactttcatt tgtaataaac    23580
tcaatgtcat tttcttcaat gtaagatgaa ataagagtag cctttgcctc gctatacatt    23640
tctaaatcgc cttgttttc tatcgtattg cgagaatttt tagcccaagc cattaatgga    23700 tcattttttcc atttttcaat aacattattg ttataccaaa tgtcatatcc tataatctgg    23760
tttttgtttt tttgaataat aaatgttact gttcttgcgg tttggaggaa ttgattcaaa    23820
ttcaagcgaa ataattcagg gtcaaaatat gtatcaatgc agcatttgag caagtgcgat    23880 aaatcttttaa gtcttctttc ccatggtttt ttagtcataa aactctccat tttgataggt    23940
tgcatgctag atgctgatat attttagagg tgataaaatt aactgcttaa ctgtcaatgt    24000
aatacaagtt gtttgatctt tgcaatgatt cttatcagaa accatatagt aaattagtta    24060
cacaggaaat ttttaatatt attattatca ttcattatgt attaaaatta gagttgtggc    24120
ttggctctgc taacacgttg ctcataggag atatggtaga gccgcagaca cgtcgtatgc    24180
aggaacgtgc tgcggctggc tggtgaactt ccgatagtgc gggtgttgaa tgatttccag    24240
ttgctaccga ttttacatat tttttgcatg agagaatttg taccacctcc caccgaccat    24300
ctatgactgt acgccactgt ccctaggact gctatgtgcc ggagcggaca ttacaaacgt    24360
ccttctcggt gcatgccact gttgccaatg acctgcctag gaattggtta gcaagttact    24420
accggatttt gtaaaaacag ccctcctcat ataaaaagta ttcgttcact tccgataagc    24480
gtcgtaattt tctatctttc atcatattct agatccctct gaaaaaatct tccgagtttg    24540
ctaggcactg atacataact ctttttccaat aattggggaa gtcattcaaa tctataatag    24600
gtttcagatt tgcttcaata aattctgact gtagctgctg aaacgttgcg gttgaactat    24660
atttccttat aacttttacg aaagagtttc tttgagtaat cacttcactc aagtgcttcc    24720
ctgcctccaa acgatacctg ttagcaatat ttaatagctt gaaatgatga agagctctgt    24780
gtttgtcttc ctgcctccag ttcgccgggc attcaacata aaaactgata gcacccggag    24840
ttccggaaac gaaatttgca tatacccatt gctcacgaaa aaaaatgtcc ttgtcgatat    24900
agggatgaat cgcttggtgt acctcatcta ctgcgaaaac ttgaccttc tctcccatat    24960 tgcagtcgcg gcacgatgga actaaattaa taggcatcac cgaaaattca ggataatgtg    25020
caataggaag aaaatgatct atattttttg tctgtcctat atcaccacaa aatggacatt    25080
tttcacctga tgaaacaagc atgtcatcgt aatatgttct agcgggtttg tttttatctc    25140
ggagattatt ttcataaagc ttttctaatt taacctttgt caggttacca actactaagg    25200
ttgtaggctc aagagggtgt gtcctgtcgt aggtaaataa ctgacctgtc gagcttaata    25260
ttctatattg ttgttctttc tgcaaaaaag tggggaagtg agtaatgaaa ttatttctaa    25320
catttatctg catcatacct tccgagcatt tattaagcat ttcgctataa gttctcgctg    25380
gaagaggtag tttttttcatt gtactttacc ttcatctctg ttcattatca tcgcttttaa    25440
aacggttcga ccttctaatc ctatctgacc attataattt tttagaatgg tttcataaga    25500
```

```
aagctctgaa tcaacggact gcgataataa gtggtggtat ccagaatttg tcacttcaag   25560
taaaaacacc tcacgagtta aaacacctaa gttctcaccg aatgtctcaa tatccggacg   25620
gataatattt attgcttctc ttgaccgtag gactttccac atgcaggatt ttggaacctc   25680
ttgcagtact actggggaat gagttgcaat tattgctaca ccattgcgtg catcgagtaa   25740
gtcgcttaat gttcgtaaaa aagcagagag caaaggtgga tgcagatgaa cctctggttc   25800
atcgaataaa actaatgact tttcgccaac gacatctact aatcttgtga tagtaaataa   25860
aacaattgca tgtccagagc tcattcgaag cagatatttc tggatattgt cataaaacaa   25920
tttagtgaat ttatcatcgt ccacttgaat ctgtggttca ttacgtctta actcttcata   25980
tttagaaatg aggctgatga gttccatatt tgaaaagttt tcatcactac ttagttttt    26040 gatagcttca agccagagtt gtcttttct atctactctc atacaaccaa taaatgctga    26100
aatgaattct aagcggagat cgcctagtga ttttaaacta ttgctggcag cattcttgag   26160
tccaatataa aagtattgtg tacctttgc tgggtcaggt tgttcttag gaggagtaaa     26220 aggatcaaat gcactaaacg aaactgaaac aagcgatcga aaatatccct ttgggattct   26280
tgactcgata agtctattat tttcagagaa aaaatattca ttgttttctg ggttggtgat   26340
tgcaccaatc attccattca aaattgttgt tttaccacac ccattccgcc cgataaaagc   26400
atgaatgttc gtgctgggca tagaattaac cgtcacctca aaaggtatag ttaaatcact   26460
gaatccggga gcacttttc tattaaatga aaagtggaaa tctgacaatt ctggcaaacc    26520
atttaacaca cgtgcgaact gtccatgaat ttctgaaaga gttaccccctc taagtaatga  26580 ggtgttaagg acgctttcat tttcaatgtc ggctaatcga tttggccata ctactaaatc   26640
ctgaatagct ttaagaaggt tatgtttaaa accatcgctt aatttgctga gattaacata   26700
gtagtcaatg ctttcaccta aggaaaaaaa catttcaggg agttgactga attttttatc   26760
tattaatgaa taagtgctta cttcttcttt ttgacctaca aaaccaattt taacatttcc   26820
gatatcgcat ttttcaccat gctcatcaaa gacagtaaga taaaacattg taacaaagga   26880
atagtcattc caaccatctg ctcgtaggaa tgccttattt ttttctactg caggaatata   26940
cccgcctctt tcaataacac taaactccaa catatagtaa cccttaattt tattaaaata   27000
accgcaattt atttggcggc aacacaggat ctctctttta agttactctc tattacatac   27060
gttttccatc taaaaattag tagtattgaa cttaacgggg catcgtattg tagttttcca   27120
tatttagctt tctgcttcct tttggataac ccactgttat tcatgttgca tggtgcactg   27180
tttataccaa cgatatagtc tattaatgca tatatagtat cgccgaacga ttagctcttc   27240
aggcttctga agaagcgttt caagtactaa taagccgata gatagccacg gacttcgtag   27300 ccattttca taagtgttaa cttccgctcc tcgctcataa cagacattca ctacagttat    27360
ggcggaaagg tatgcatgct gggtgtgggg aagtcgtgaa agaaaagaag tcagctgcgt   27420
cgtttgacat cactgctatc ttcttactgg ttatgcaggt cgtagtgggt ggcacacaaa   27480
gctttgcact ggattgcgag gctttgtgct tctctggagt gcgacaggtt tgatgacaaa   27540
aaattagcgc aagaagacaa aaatcaccctt gcgctaatgc tctgttacag gtcactaata  27600
ccatctaagt agttgattca tagtgactgc atatgttgtg ttttacagta ttatgtagtc   27660
tgttttttat gcaaaatcta atttaatata ttgatattta tatcattta cgtttctcgt    27720 tcagcttttt tatactaagt tggcattata aaaaagcatt gcttatcaat tgttgcaac    27780 gaacaggtca ctatcagtca aaataaaatc attatttgat ttcaattttg tcccactccc   27840
```

```
tgcctctgtc atcacgatac tgtgatgcca tggtgtccga cttatgcccg agaagatgtt    27900
gagcaaactt atcgcttatc tgcttctcat agagtcttgc agacaaactg cgcaactcgt    27960
gaaaggtagg cggatcccct tcgaaggaaa gacctgatgc ttttcgtgcg cgcataaaat    28020
accttgatac tgtgccggat gaaagcggtt cgcgacgagt agatgcaatt atggtttctc    28080
cgccaagaat ctctttgcat ttatcaagtg tttccttcat tgatattccg agagcatcaa    28140
tatgcaatgc tgttgggatg gcaattttta cgcctgtttt gctttgctcg acataaagat    28200
atccatctac gatatcagac cacttcattt cgcataaatc accaactcgt tgcccggtaa    28260
caacagccag ttccattgca agtctgagcc aacatggtga tgattctgct gcttgataaa    28320
ttttcaggta ttcgtcagcc gtaagtcttg atctccttac ctctgatttt gctgcgcgag    28380
tggcagcgac atggtttgtt gttatatggc cttcagctat tgcctctcgg aatgcatcgc    28440
tcagtgttga tctgattaac ttggctgacg ccgccttgcc ctcgtctatg tatccattga    28500
gcattgccgc aatttctttt gtggtgatgt cttcaagtgg agcatcaggc agacccctcc    28560
ttattgcttt aattttgctc atgtaattta tgagtgtctt ctgcttgatt cctctgctgg    28620
ccaggatttt ttcgtagcga tcaagccatg aatgtaacgt aacggaatta tcactgttga    28680
ttctcgctgt cagaggcttg tgtttgtgtc ctgaaaataa ctcaatgttg gcctgtatag    28740
cttcagtgat tgcgattcgc ctgtctctgc ctaatccaaa ctcttttaccc gtccttgggt    28800
ccctgtagca gtaatatcca ttgtttctta tataaaggtt aggggggtaaa tcccggcgct    28860
catgacttcg ccttcttccc atttctgatc ctcttcaaaa ggccacctgt tactggtcga    28920
tttaagtcaa cctttaccgc tgattcgtgg aacagatact ctcttccatc cttaaccgga    28980
ggtgggaata tcctgcattc ccgaacccat cgacgaactg tttcaaggct tcttggacgt    29040
cgctggcgtg cgttccactc ctgaagtgtc aagtacatcg caaagtctcc gcaattacac    29100
gcaagaaaaa accgccatca ggcggcttgg tgttctttca gttcttcaat tcgaatattg    29160
gttacgtctg catgtgctat ctgcgcccat atcatccagt ggtcgtagca gtcgttgatg    29220
ttctccgctt cgataactct gttgaatggc tctccattcc attctcctgt gactcggaag    29280
tgcatttatc atctccataa aacaaaaccc gccgtagcga gttcagataa aataaatccc    29340
cgcgagtgcg aggattgtta tgtaatattg ggtttaatca tctatatgtt ttgtacagag    29400
agggcaagta tcgtttccac cgtactcgtg ataataattt tgcacggtat cagtcatttc    29460
tcgcacattg cagaatgggg atttgtcttc attagactta taaaccttca tggaatattt    29520
gtatgccgac tctatatcta taccttcatc tacataaaca ccttcgtgat gtctgcatgg    29580
agacaagaca ccggatctgc acaacattga taacgcccaa tcttttttgct cagactctaa    29640
ctcattgata ctcatttata aactccttgc aatgtatgtc gtttcagcta acggtatca    29700
gcaatgttta tgtaaagaaa cagtaagata atactcaacc cgatgtttga gtacggtcat    29760
catctgacac tacagactct ggcatcgctg tgaagacgac gcgaaattca gcattttcac    29820
aagcgttatc ttttacaaaa ccgatctcac tctcctttga tgcgaatgcc agcgtcagac    29880
atcatatgca gatactcacc tgcatcctga acccattgac ctccaacccc gtaatagcga    29940
tgcgtaatga tgtcgatagt tactaacggg tcttgttcga ttaactgccg cagaaactct    30000
tccaggtcac cagtgcagtg cttgataaca ggagtcttcc caggatggcg aacaacaaga    30060
aactggtttc cgtcttcacg gacttcgttg cttttccagtt tagcaatacg cttactccca    30120
tccgagataa caccttcgta atactcacgc tgctcgttga gttttgattt tgctgtttca    30180
agctcaacac gcagtttccc tactgttagc gcaatatcct cgttctcctg gtcgcggcgt    30240
```

```
ttgatgtatt gctggtttct ttcccgttca tccagcagtt ccagcacaat cgatggtgtt   30300
accaattcat ggaaaaggtc tgcgtcaaat ccccagtcgt catgcattgc ctgctctgcc   30360
gcttcacgca gtgcctgaga gttaatttcg ctcacttcga acctctctgt ttactgataa   30420
gttccagatc ctcctggcaa cttgcacaag tccgacaacc ctgaacgacc aggcgtcttc   30480
gttcatctat cggatcgcca cactcacaac aatgagtggc agatatagcc tggtggttca   30540
ggcggcgcat ttttattgct gtgttgcgct gtaattcttc tatttctgat gctgaatcaa   30600
tgatgtctgc catctttcat taatccctga actgttggtt aatacgcttg agggtgaatg   30660
cgaataataa aaaaggagcc tgtagctccc tgatgatttt gcttttcatg ttcatcgttc   30720
cttaaagacg ccgtttaaca tgccgattgc caggcttaaa tgagtcggtg tgaatcccat   30780
cagcgttacc gttcgcggt gcttcttcag tacgctacgg caaatgtcat cgacgttttt   30840
atccggaaac tgctgtctgg cttttttga tttcagaatt agcctgacgg caatgctgc   30900 gaagggcgtt ttcctgctga ggtgtcattg aacaagtccc atgtcggcaa gcataagcac   30960
acagaatatg aagcccgctg ccagaaaaat gcattccgtg gttgtcatac ctggtttctc   31020
tcatctgctt ctgctttcgc caccatcatt tccagctttt gtgaaaggga tgcggctaac   31080
gtatgaaatt cttcgtctgt ttctactggt attggcacaa acctgattcc aatttgagca   31140
aggctatgtg ccatctcgat actcgttctt aactcaacag aagatgcttt gtgcatacag   31200
cccctcgttt attatttatc tcctcagcca gccgctgtgc tttcagtgga tttcggataa   31260
cagaaaggcc gggaaatacc cagcctcgct ttgtaacgga gtagacgaaa gtgattgcgc   31320
ctacccggat attatcgtga ggatgcgtca tcgccattgc tccccaaata caaaaccaat   31380
ttcagccagt gcctcgtcca ttttttcgat gaactccggc acgatctcgt caaaactcgc   31440
catgtacttt tcatcccgct caatcacgac ataatgcagg ccttcacgct tcatacgcgg   31500
gtcatagttg gcaaagtacc aggcattttt tcgcgtcacc cacatgctgt actgcacctg   31560
ggccatgtaa gctgacttta tggcctcgaa accaccgagc cggaacttca tgaaatcccg   31620
ggaggtaaac gggcatttca gttcaaggcc gttgccgtca ctgcataaac catcgggaga   31680
gcaggcggta cgcatacttt cgtcgcgata gatgatcggg gattcagtaa cattcacgcc   31740
ggaagtgaat tcaaacaggg ttctggcgtc gttctcgtac tgttttcccc aggccagtgc   31800
tttagcgtta acttccggag ccacaccggt gcaaacctca gcaagcaggg tgtggaagta   31860
ggacattttc atgtcaggcc acttctttcc ggagcggggt tttgctatca cgttgtgaac   31920
ttctgaagcg gtgatgacgc cgagccgtaa tttgtgccac gcatcatccc cctgttcgac   31980
agctctcaca tcgatcccgg tacgctgcag gataatgtcc ggtgtcatgc tgccaccttc   32040
tgctctgcgg ctttctgttt caggaatcca agagcttta ctgcttcggc ctgtgtcagt   32100
tctgacgatg cacgaatgtc gcggcgaaat atctgggaac agagcggcaa taagtcgtca   32160
tcccatgttt tatccagggc gatcagcaga gtgttaatct cctgcatggt ttcatcgtta   32220
accggagtga tgtcgcgttc cggctgacgt tctgcagtgt atgcagtatt ttcgacaatg   32280
cgctcggctt catccttgtc atagataccc agcaaatccga aggccagacg ggcacactga   32340
atcatggctt tatgacgtaa catccgtttg ggatgcgact gccacggccc cgtgatttct   32400
ctgccttcgc gagttttgaa tggttcgcgg cggcattcat ccatccattc ggtaacgcag   32460
atcggatgat tacggtcctt gcggtaaatc cggcatgtac aggattcatt gtcctgctca   32520
aagtccatgc catcaaactg ctggttttca ttgatgatgc gggaccagcc atcaacgccc   32580
```

-continued

```
accaccggaa cgatgccatt ctgcttatca ggaaaggcgt aaatttcttt cgtccacgga    32640
ttaaggccgt actggttggc aacgatcagt aatgcgatga actgcgcatc gctggcatca    32700
cctttaaatg ccgtctggcg aagagtggtg atcagttcct gtgggtcgac agaatccatg    32760
ccgacacgtt cagccagctt cccagccagc gttgcgagtg cagtactcat tcgttttata    32820
cctctgaatc aatatcaacc tggtggtgag caatggtttc aaccatgtac cggatgtgtt    32880
ctgccatgcg ctcctgaaac tcaacatcgt catcaaacgc acgggtaatg gattttttgc    32940
tggccccgtg gcgttgcaaa tgatcgatgc atagcgattc aaacaggtgc tggggcaggc    33000 cttttttccat gtcgtctgcc agttctgcct ctttctcttc acgggcgagc tgctggtagt    33060
gacgcgccca gctctgagcc tcaagacgat cctgaatgta ataagcgttc atggctgaac    33120
tcctgaaata gctgtgaaaa tatcgcccgc gaaatgccgg gctgattagg aaaacaggaa    33180
agggggttag tgaatgcttt tgcttgatct cagtttcagt attaatatcc attttttata    33240
agcgtcgacg gcttcacgaa acatcttttc atcgccaata aaagtggcga tagtgaattt    33300
agtctggata gccataagtg tttgatccat tctttgggac tcctggctga ttaagtatgt    33360
cgataaggcg tttccatccg tcacgtaatt tacgggtgat tcgttcaagt aaagattcgg    33420
aagggcagcc agcaacaggc caccctgcaa tggcatattg catggtgtgc tccttattta    33480
tacataacga aaaacgcctc gagtgaagcg ttattggtat gcggtaaaac cgcactcagg    33540
cggccttgat agtcatatca tctgaatcaa atattcctga tgtatcgata tcggtaattc    33600
ttattccttc gctaccatcc attggaggcc atccttcctg accatttcca tcattccagt    33660
cgaactcaca cacaacacca tatgcattta agtcgcttga aattgctata agcagagcat    33720
gttgcgccag catgattaat acagcattta atacagagcc gtgttattg agtcggtatt    33780 cagagtctga ccagaaatta ttaatctggt gaagttttc ctctgtcatt acgtcatggt    33840
cgatttcaat ttctattgat gctttccagt cgtaatcaat gatgtatttt ttgatgtttg    33900
acatctgttc atatcctcac agataaaaaa tcgccctcac actggagggc aaagaagatt    33960
tccaataatc agaacaagtc ggctcctgtt tagttacgag cgacattgct ccgtgtattc    34020
actcgttgga atgaatacac agtgcagtgt ttattctgtt atttatgcca aaaataaagg    34080
ccactatcag gcagctttgt tgttctgttt accaagttct ctggcaatca ttgccgtcgt    34140
tcgtattgcc catttatcga catatttccc atcttccatt acaggaaaca tttcttcagg    34200
cttaaccatg cattccgatt gcagcttgca tccattgcat cgcttgaatt gtccacacca    34260 ttgatttta tcaatagtcg tagtcatacg gatagtcctg gtattgttcc atcacatcct    34320
gaggatgctc ttcgaactct tcaaattctt cttccatata tcaccttaaa tagtggattg    34380
cggtagtaaa gattgtgcct gtctttaac cacatcaggc tcggtggttc tcgtgtaccc    34440
ctacagcgag aaatcggata aactattaca accctacag tttgatgagt atagaaatgg    34500
atccactcgt tattctcgga cgagtgttca gtaatgaacc tctggagaga accatgtata    34560
tgatcgttat ctgggttgga cttctgcttt taagcccaga taactggcct gaatatgtta    34620
atgagagaat cggtattcct catgtgtggc atgttttcgt cttgctctt gcattttcgc    34680 tagcaattaa tgtgcatcga ttatcagcta ttgccagcgc cagatataag cgatttaagc    34740
taagaaaacg cattaagatg caaaacgata aagtgcgatc agtaattcaa aaccttacag    34800
aagagcaatc tatggttttg tgcgcagccc ttaatgaagg caggaagtat gtggttacat    34860
caaaacaatt cccatacatt agtgagttga ttgagcttgg tgtgttgaac aaaacttttt    34920
cccgatggaa tggaaagcat atattattcc ctattgagga tatttactgg actgaattag    34980
```

```
ttgccagcta tgatccatat aatattgaga taaagccaag gccaatatct aagtaactag    35040
ataagaggaa tcgattttcc cttaattttc tggcgtccac tgcatgttat gccgcgttcg    35100
ccaggcttgc tgtaccatgt gcgctgattc ttgcgctcaa tacgttgcag gttgctttca    35160
atctgtttgt ggtattcagc cagcactgta aggtctatcg gatttagtgc gctttctact    35220
cgtgatttcg gtttgcgatt cagcgagaga atagggcggt taactggttt tgcgcttacc    35280
ccaaccaaca ggggatttgc tgctttccat tgagcctgtt tctctgcgcg acgttcgcgg    35340
cggcgtgttt gtgcatccat ctggattctc ctgtcagtta gctttggtgg tgtgtggcag    35400
ttgtagtcct gaacgaaaac cccccgcgat tggcacattg gcagctaatc cggaatcgca    35460
cttacggcca atgcttcgtt tcgtatcaca caccccaaag ccttctgctt tgaatgctgc    35520
ccttcttcag ggcttaattt ttaagagcgt caccttcatg gtggtcagtg cgtcctgctg    35580
atgtgctcag tatcaccgcc agtggtattt atgtcaacac cgccagagat aatttatcac    35640
cgcagatggt tatctgtatg ttttttatat gaatttattt tttgcagggg ggcattgttt    35700
ggtaggtgag agatctgaat tgctatgttt agtgagttgt atctatttat ttttcaataa    35760
atacaattgg ttatgtgttt tgggggcgat cgtgaggcaa agaaaacccg gcgctgaggc    35820
cgggttattc ttgttctctg gtcaaattat atagttggaa aacaaggatg catatatgaa    35880
tgaacgatgc agaggcaatg ccgatggcga tagtgggtat catgtagccg cttatgctgg    35940
aaagaagcaa taacccgcag aaaaacaaag ctccaagctc aacaaaacta agggcataga    36000
caataactac cgatgtcata tacccatact ctctaatctt ggccagtcgg cgcgttctgc    36060
ttccgattag aaacgtcaag gcagcaatca ggattgcaat catggttcct gcatatgatg    36120
acaatgtcgc cccaagacca tctctatgag ctgaaaaaga acaccagga atgtagtggc    36180 ggaaaaggag atagcaaatg cttacgataa cgtaaggaat tattactatg taaacaccag    36240
gcatgattct gttccgcata attactcctg ataattaatc cttaactttg cccacctgcc    36300
ttttaaaaca ttccagtata tcacttttca ttcttgcgta gcaatatgcc atctcttcag    36360
ctatctcagc attggtgacc ttgttcagag gcgctgagag atggcctttt tctgatagat    36420
aatgttctgt taaatatct ccggcctcat cttttgcccg caggctaatg tctgaaaatt    36480
gaggtgacgg gttaaaaata atatccttgg caacctttt tatatccctt ttaaattttg     36540
gcttaatgac tatatccaat gagtcaaaaa gctccccttc aatatctgtt gccctaagaa    36600
cctttaatat atcgccaaat acaggtagct tggcttctac cttcaccgtt gttcggccga    36660
tgaaatgcat atgcataaca tcgtctttgg tggttcccct catcagtggc tctatctgaa    36720
cgcgctctcc actgcttaat gacattcctt tcccgattaa aaaatctgtc agatcggatg    36780
tggtcggccc gaaaacagtt ctggcaaaac caatggtgtc gccttcaaca aacaaaaaag    36840
atgggaatcc caatgattcg tcatctgcga ggctgttctt aatatcttca actgaagctt    36900
tagagcgatt tatcttctga accagactct tgtcatttgt tttggtaaag agaaagtttt    36960
ttccatcgat tttatgaata tacaaataat tggagccaac ctgcaggtga tgattatcag    37020
ccagcagaga attaaggaaa acagacaggt ttattgagcg cttatctttc cctttatttt    37080
tgctgcggta agtcgcataa aaaccattct tcataattca atccatttac tatgttatgt    37140
tctgagggga gtgaaaattc ccctaattcg atgaagattc ttgctcaatt gttatcagct    37200
atgcgccgac cagaacacct tgccgatcag ccaaacgtct cttcaggcca ctgactagcg    37260
ataactttcc ccacaacgga acaactctca ttgcatggga tcattgggta ctgtgggttt    37320
```

```
agtggttgta aaaacacctg accgctatcc ctgatcagtt tcttgaaggt aaactcatca    37380 ccccccaagtc tggctatgca gaaatcacct ggctcaacag cctgctcagg gtcaacgaga    37440
attaacattc cgtcaggaaa gcttggcttg gagcctgttg gtgcggtcat ggaattacct    37500
tcaacctcaa gccagaatgc agaatcactg gctttttttgg ttgtgcttac ccatctctcc    37560
gcatcacctt tggtaaaggt tctaagctca ggtgagaaca tccctgcctg aacatgagaa    37620
aaaacagggt actcatactc acttctaagt gacggctgca tactaaccgc ttcatacatc    37680
tcgtagattt ctctggcgat tgaagggcta aattcttcaa cgctaacttt gagaattttt    37740
gcaagcaatg cggcgttata agcatttaat gcattgatgc cattaaataa agcaccaacg    37800
cctgactgcc ccatccccat cttgtctgcg acagattcct gggataagcc aagttcattt    37860
ttcttttttt cataaattgc tttaaggcga cgtgcgtcct caagctgctc ttgtgttaat    37920
ggtttctttt ttgtgctcat acgttaaatc tatcaccgca agggataaat atctaacacc    37980
gtgcgtgttg actattttac ctctggcggt gataatggtt gcatgtacta aggaggttgt    38040
atggaacaac gcataaccct gaaagattat gcaatgcgct tgggcaaac caagacagct    38100 aaagatctcg gcgtatatca aagcgcgatc aacaaggcca ttcatgcagg ccgaaagatt    38160
tttttaacta taaacgctga tggaagcgtt tatgcggaag aggtaaagcc cttcccgagt    38220 aacaaaaaaaa caacagcata aataaccccg ctcttacaca ttccagcccct gaaaagggc    38280 atcaaattaa accacaccta tggtgtatgc atttatttgc atacattcaa tcaattgtta    38340
tctaaggaaa tacttacata tggttcgtgc aaacaaacgc aacgaggctc tacgaatcga    38400
gagtgcgttg cttaacaaaa tcgcaatgct tggaactgag aagacagcgg aagctgtggg    38460
cgttgataag tcgcagatca gcaggtggaa gagggactgg attccaaagt tctcaatgct    38520
gcttgctgtt cttgaatggg gggtcgttga cgacgcacatg gctcgattgg cgcgacaagt    38580
tgctgcgatt ctcaccaata aaaacgccc ggcggcaacc gagcgttctg aacaaatcca    38640
gatggagttc tgaggtcatt actggatcta tcaacaggag tcattatgac aaatacagca    38700
aaaatactca acttcggcag aggtaacttt gccggacagg agcgtaatgt ggcagatctc    38760
gatgatggtt acgccagact atcaaatatg ctgcttgagg cttattcggg cgcagatctg    38820
accaagcgac agtttaaagt gctgcttgcc attctgcgta aaacctatgg gtggaataaa    38880
ccaatggaca gaatcaccga ttctcaactt agcgagatta caaagttacc tgtcaaacgg    38940
tgcaatgaag ccaagttaga actcgtcaga atgaatatta tcaagcagca aggcggcatg    39000
tttggaccaa ataaaaacat ctcagaatgg tgcatccctc aaaacgaggg aaaatcccct    39060
aaaacgaggg ataaaacatc cctcaaattg ggggattgct atccctcaaa acaggggggac    39120 acaaagaca ctattacaaa agaaaaaga aaagattatt cgtcagagaa ttctggcgaa    39180
tcctctgacc agccagaaaa cgacctttct gtggtgaaac cggatgctgc aattcagagc    39240
ggcagcaagt gggggacagc agaagacctg accgccgcag agtggatgtt tgacatggtg    39300
aagactatcg caccatcagc cagaaaaccg aattttgctg ggtgggctaa cgatatccgc    39360
ctgatgcgtg aacgtgacgg acgtaaccac cgcgacatgt gtgtgctgtt ccgctgggca    39420
tgccaggaca acttctggtc cggtaacgtg ctgagcccgg ccaaactccg cgataagtgg    39480
acccaactcg aaatcaaccg taacaagcaa caggcaggcg tgacagccag caaaccaaaa    39540
ctcgacctga caaacacaga ctggatttac ggggtggatc tatgaaaaac atcgccgcac    39600
agatggttaa ctttgaccgt gagcagatgc gtcggatcgc caacaacatg ccggaacagt    39660
acgacgaaaa gccgcaggta cagcaggtag cgcagatcat caacggtgtg ttcagccagt    39720
```

```
tactggcaac tttcccggcg agcctggcta accgtgacca gaacgaagtg aacgaaatcc    39780
gtcgccagtg ggttctggct tttcgggaaa acgggatcac cacgatggaa caggttaacg    39840
caggaatgcg cgtagcccgt cggcagaatc gaccatttct gccatcaccc gggcagtttg    39900
ttgcatggtg ccgggaagaa gcatccgtta ccgccggact gccaaacgtc agcgagctgg    39960
ttgatatggt ttacgagtat tgccggaagc gaggcctgta tccggatgcg gagtcttatc    40020 cgtgaaatc aaacgcgcac tactggctgg ttaccaacct gtatcagaac atgcgggcca    40080
atgcgcttac tgatgcggaa ttacgccgta aggccgcaga tgagcttgtc catatgactg    40140
cgagaattaa ccgtggtgag gcgatccctg aaccagtaaa acaacttcct gtcatgggcg    40200
gtagacctct aaatcgtgca caggctctgg cgaagatcgc agaaatcaaa gctaagttcg    40260
gactgaaagg agcaagtgta tgacgggcaa agaggcaatt attcattacc tggggacgca    40320
taatagcttc tgtgcgccgg acgttgccgc gctaacaggc gcaacagtaa ccagcataaa    40380
tcaggccgcg gctaaaatgg cacgggcagg tcttctggtt atcgaaggta aggtctggcg    40440
aacggtgtat taccggtttg ctaccaggga agaacgggaa ggaaagatga gcacgaacct    40500
ggtttttaag gagtgtcgcc agagtgccgc gatgaaacgg gtattggcgg tatatggagt    40560
taaaagatga ccatctacat tactgagcta ataacaggcc tgctggtaat cgcaggcctt    40620
tttatttggg ggagagggaa gtcatgaaaa aactaacctt tgaaattcga tctccagcac    40680
atcagcaaaa cgctattcac gcagtacagc aaatccttcc agacccaacc aaaccaatcg    40740
tagtaaccat tcaggaacgc aaccgcagct tagaccaaaa caggaagcta tgggcctgct    40800
taggtgacgt ctctcgtcag gttgaatggc atggtcgctg gctggatgca gaaagctgga    40860
agtgtgtgtt taccgcagca ttaaagcagc aggatgttgt tcctaacctt gccgggaatg    40920
gctttgtggt aataggccag tcaaccagca ggatgcgtgt aggcgaattt gcggagctat    40980
tagagcttat acaggcattc ggtacagagc gtggcgttaa gtggtcagac gaagcgagac    41040
tggctctgga gtggaaagcg agatggggag acagggctgc atgataaatg tcgttagttt    41100
ctccggtggc aggacgtcag catatttgct ctggctaatg gagcaaaagc gacgggcagg    41160
taaagacgtg cattacgttt tcatggatac aggttgtgaa catccaatga catatcggtt    41220
tgtcagggaa gttgtgaagt ctgggatat accgctcacc gtattgcagg ttgatatcaa    41280
cccggagctt ggacagccaa atggttatac ggtatgggaa ccaaaggata ttcagacgcg    41340
aatgcctgtt ctgaagccat ttatcgatat ggtaaagaaa tatggcactc catacgtcgg    41400
cggcgcgttc tgcactgaca gattaaaact cgttcccttc accaaatact gtgatgacca    41460
tttcgggcga gggaattaca ccacgtggat tggcatcaga gctgatgaac cgaagcggct    41520
aaagccaaag cctggaatca gatatcttgc tgaactgtca gactttgaga aggaagatat    41580
cctcgcatgg tggaagcaac aaccattcga tttgcaaata ccggaacatc tcggtaactg    41640
catattctgc attaaaaaat caacgcaaaa aatcggactt gcctgcaaag atgaggaggg    41700
attgcagcgt gttttaatg aggtcatcac gggatcccat gtgcgtgacg gacatcggga    41760
aacgccaaag gagattatgt accgaggaag aatgtcgctg gacggtatcg cgaaaatgta    41820
ttcagaaaat gattatcaag ccctgtatca ggacatggta cgagctaaaa gattcgatac    41880
cggctcttgt tctgagtcat gcgaaatatt tggagggcag cttgatttcg acttcgggag    41940
ggaagctgca tgatgcgatg ttatcggtgc ggtgaatgca agaagataa ccgcttccga    42000 ccaaatcaac cttactggaa tcgatggtgt ctccggtgtg aaagaacacc aacaggggtg    42060
```

-continued

```
ttaccactac cgcaggaaaa ggaggacgtg tggcgagaca gcgacgaagt atcaccgaca    42120
taatctgcga aaactgcaaa taccttccaa cgaaacgcac cagaaataaa cccaagccaa    42180
tcccaaaaga atctgacgta aaaaccttca actacacggc tcacctgtgg gatatccggt    42240
ggctaagacg tcgtgcgagg aaaacaaggt gattgaccaa aatcgaagtt acgaacaaga    42300
aagcgtcgag cgagctttaa cgtgcgctaa ctgcggtcag aagctgcatg tgctggaagt    42360
tcacgtgtgt gagcactgct gcgcagaact gatgagcgat ccgaatagct cgatgcacga    42420
ggaagaagat gatggctaaa ccagcgcgaa gacgatgtaa aaacgatgaa tgccgggaat    42480
ggtttcaccc tgcattcgct aatcagtggt ggtgctctcc agagtgtgga accaagatag    42540
cactcgaacg acgaagtaaa gaacgcgaaa aagcggaaaa agcagcagag aagaaacgac    42600
gacgagagga gcagaaacag aaagataaac ttaagattcg aaaactcgcc ttaaagcccc    42660
gcagttactg gattaaacaa gcccaacaag ccgtaaacgc cttcatcaga gaaagagacc    42720
gcgacttacc atgtatctcg tgcggaacgc tcacgtctgc tcagtgggat gccggacatt    42780
accggacaac tgctgcggca cctcaactcc gatttaatga acgcaatatt cacaagcaat    42840
gcgtggtgtg caaccagcac aaaagcggaa atctcgttcc gtatcgcgtc gaactgatta    42900
gccgcatcgg gcaggaagca gtagacgaaa tcgaatcaaa ccataaccgc catcgctgga    42960
ctatcgaaga gtgcaaggcg atcaaggcag agtaccaaca gaaactcaaa gacctgcgaa    43020
atagcagaag tgaggccgca tgacgttctc agtaaaaacc attccagaca tgctcgttga    43080
agcatacgga aatcagacag aagtagcacg cagactgaaa tgtagtcgcg gtacggtcag    43140
aaaatacgtt gatgataaag acgggaaaat gcacgccatc gtcaacgacg ttctcatggt    43200
tcatcgcgga tggagtgaaa gagatgcgct attacgaaaa aattgatggc agcaaatacc    43260
gaaatatttg ggtagttggc gatctgcacg gatgctacac gaacctgatg aacaaactgg    43320
atacgattgg attcgacaac aaaaaagacc tgcttatctc ggtgggcgat ttggttgatc    43380
gtggtgcaga gaacgttgaa tgcctggaat taatcacatt cccctggttc agagctgtac    43440
gtggaaacca tgagcaaatg atgattgatg gcttatcaga gcgtggaaac gttaatcact    43500
ggctgcttaa tggcggtggc tggttctttta atctcgatta cgacaaagaa attctggcta    43560
aagctcttgc ccataaagca gatgaacttc cgttaatcat cgaactggtg agcaaagata    43620
aaaaatatgt tatctgccac gccgattatc cctttgacga atacgagttt ggaaagccag    43680
ttgatcatca gcaggtaatc tggaaccgcg aacgaatcag caactcacaa aacgggatcg    43740
tgaaagaaat caaaggcgcg gacacgttca tcttttggtca tacgccagca gtgaaaccac    43800
tcaagtttgc caaccaaatg tatatcgata ccggcgcagt gttctgcgga aacctaacat    43860
tgattcaggt acagggagaa ggcgcatgag actcgaaagc gtagctaaat ttcattcgcc    43920
aaaaagcccg atgatgagcg actccaccacg ggccacggct tctgactctc tttccggtac    43980
tgatgtgatg gctgctatgg ggatggcgca atcacaagcc ggattcggta tggctgcatt    44040
ctgcggtaag cacgaactca gccagaacga caaacaaaag gctatcaact atctgatgca    44100
atttgcacac aaggtatcgg ggaaataccg tggtgtggca aagcttgaag gaaatactaa    44160
ggcaaaggta ctgcaagtgc tcgcaacatt cgcttatgcg gattattgcc gtagtgccgc    44220
gacgccgggg gcaagatgca gagattgcca tggtacaggc cgtgcggttg atattgccaa    44280
aacagagctg tgggggagag ttgtcgagaa agagtgcgga agatgcaaag gcgtcggcta    44340
ttcaaggatg ccagcaagcg cagcatatcg cgctgtgacg atgctaatcc caaaccttac    44400
ccaacccacc tggtcacgca ctgttaagcc gctgtatgac gctctggtgg tgcaatgcca    44460
```

```
caaagaagag tcaatcgcag acaacatttt gaatgcggtc acacgttagc agcatgattg    44520
ccacggatgg caacatatta acggcatgat attgacttat tgaataaaat tgggtaaatt    44580
tgactcaacg atgggttaat tcgctcgttg tggtagtgag atgaaaagag gcggcgctta    44640
ctaccgattc cgcctagttg gtcacttcga cgtatcgtct ggaactccaa ccatcgcagg    44700
cagagaggtc tgcaaaatgc aatcccgaaa cagttcgcag gtaatagtta gagcctgcat    44760
aacggtttcg ggattttta tatctgcaca acaggtaaga gcattgagtc gataatcgtg     44820
aagagtcggc gagcctggtt agccagtgct ctttccgttg tgctgaatta agcgaatacc    44880
ggaagcagaa ccggatcacc aaatgcgtac aggcgtcatc gccgcccagc aacagcacaa    44940
cccaaactga gccgtagcca ctgtctgtcc tgaattcatt agtaatagtt acgctgcggc    45000
cttttacaca tgaccttcgt gaaagcgggt ggcaggaggt cgcgctaaca acctcctgcc    45060
gttttgcccg tgcatatcgg tcacgaacaa atctgattac taaacacagt agcctggatt    45120
tgttctatca gtaatcgacc ttattcctaa ttaaatagag caaatcccct tattgggggt    45180
aagacatgaa gatgccagaa aaacatgacc tgttggccgc cattctcgcg gcaaaggaac    45240
aaggcatcgg ggcaatcctt gcgtttgcaa tggcgtacct tcgcggcaga tataatggcg    45300
gtgcgtttac aaaaacagta atcgacgcaa cgatgtgcgc cattatcgcc tggttcattc    45360
gtgaccttct cgacttcgcc ggactaagta gcaatctcgc ttatataacg agcgtgttta    45420
tcggctacat cggtactgac tcgattggtt cgcttatcaa acgcttcgct gctaaaaaag    45480
ccggagtaga agatggtaga atcaataat caacgtaagg cgttcctcga tatgctggcg     45540
tggtcggagg gaactgataa cggacgtcag aaaaccagaa atcatggtta tgacgtcatt    45600
gtaggcggag agctatttac tgattactcc gatcaccctc gcaaacttgt cacgctaaac    45660
ccaaaactca aatcaacagg cgccggacgc taccagcttc tttcccgttg gtgggatgcc    45720
taccgcaagc agcttggcct gaaagacttc tctccgaaaa gtcaggacgc tgtggcattg    45780
cagcagatta aggagcgtgg cgcttttacct atgattgatc gtggtgatat ccgtcaggca    45840
atcgaccgtt gcagcaatat ctgggcttca ctgccgggcg ctggttatgg tcagttcgag    45900
cataaggctg acagcctgat tgcaaaattc aaagaagcgg gcggaacggt cagagagatt    45960
gatgtatgag cagagtcacc gcgattatct ccgctctggt tatctgcatc atcgtctgcc    46020
tgtcatgggc tgttaatcat taccgtgata acgccattac ctacaaagcc cagcgcgaca    46080
aaaatgccag agaactgaag ctggcgaacg cggcaattac tgacatgcag atgcgtcagc    46140
gtgatgttgc tgcgctcgat gcaaaataca cgaaggagtt agctgatgct aaagctgaaa    46200
atgatgctct gcgtgatgat gttgccgctg gtcgtcgtcg gttgcacatc aaagcagtct    46260
gtcagtcagt gcgtgaagcc accaccgcct ccggcgtgga taatgcagcc tcccccgac    46320 tggcagacac cgctgaacgg gattatttca ccctcagaga gaggctgatc actatgcaaa    46380
aacaactgga aggaacccag aagtatatta atgagcagtg cagatagagt tgcccatatc    46440
gatgggcaac tcatgcaatt attgtgagca atacacacgc gcttccagcg gagtataaat    46500
gcctaaagta ataaaaccga gcaatccatt tacgaatgtt tgctgggttt ctgttttaac    46560
aacattttct gcgccgccac aaattttggc tgcatcgaca gttttcttct gcccaattcc    46620
agaaacgaag aaatgatggg tgatggtttc ctttggtgct actgctgccg gtttgttttg    46680
aacagtaaac gtctgttgag cacatcctgt aataagcagg gccagcgcag tagcgagtag    46740 cattttttc atggtgttat tcccgatgct ttttgaagtt cgcagaatcg tatgtgtaga    46800
```

```
aaattaaaca aaccctaaac aatgagttga aatttcatat tgttaatatt tattaatgta   46860
tgtcaggtgc gatgaatcgt cattgtattc ccggattaac tatgtccaca gccctgacgg   46920
ggaacttctc tgcgggagtg tccgggaata attaaaacga tgcacacagg gtttagcgcg   46980
tacacgtatt gcattatgcc aacgccccgg tgctgacacg gaagaaaccg gacgttatga   47040
tttagcgtgg aaagatttgt gtagtgttct gaatgctctc agtaaatagt aatgaattat   47100
caaaggtata gtaatatctt ttatgttcat ggatatttgt aacccatcgg aaaactcctg   47160
ctttagcaag attttccctg tattgctgaa atgtgatttc tcttgatttc aacctatcat   47220
aggacgtttc tataagatgc gtgtttcttg agaatttaac atttacaacc ttttaagtc    47280 cttttattaa cacggtgtta tcgttttcta acacgatgtg aatattatct gtggctagat   47340
agtaaatata atgtgagacg ttgtgacgtt ttagttcaga ataaaacaat tcacagtcta   47400
aatcttttcg cacttgatcg aatatttctt taaaaatggc aacctgagcc attggtaaaa   47460
ccttccatgt gatacgaggg cgcgtagttt gcattatcgt ttttatcgtt tcaatctggt   47520
ctgacctcct tgtgttttgt tgatgattta tgtcaaatat taggaatgtt ttcacttaat   47580
agtattggtt gcgtaacaaa gtgcggtcct gctggcattc tggagggaaa tacaaccgac   47640
agatgtatgt aaggccaacg tgctcaaatc ttcatacaga aagatttgaa gtaatatttt   47700
aaccgctaga tgaagagcaa gcgcatggag cgacaaaatg aataaagaac aatctgctga   47760
tgatccctcc gtggatctga ttcgtgtaaa aaatatgctt aatagcacca tttctatgag   47820
ttaccctgat gttgtaattg catgtataga acataaggtg tctctggaag cattcagagc   47880
aattgaggca gcgttggtga agcacgataa taatatgaag gattattccc tggtggttga   47940
ctgatcacca taactgctaa tcattcaaac tatttagtct gtgacagagc caacacgcag   48000
tctgtcactg tcaggaaagt ggtaaaactg caactcaatt actgcaatgc cctcgtaatt   48060
aagtgaattt acaatatcgt cctgttcgga gggaagaacg cgggatgttc attcttcatc   48120
acttttaatt gatgtatatg ctctcttttc tgacgttagt ctccgacggc aggcttcaat   48180
gacccaggct gagaaattcc cggacccttt ttgctcaaga gcgatgttaa tttgttcaat   48240
catttggtta ggaaagcgga tgttgcgggt tgttgttctg cgggttctgt tcttcgttga   48300
catgaggttg ccccgtattc agtgtcgctg atttgtattg tctgaagttg ttttttacgtt   48360 aagttgatgc agatcaatta atacgatacc tgcgtcataa ttgattattt gacgtggttt   48420
gatggcctcc acgcacgttg tgatatgtag atgataatca ttatcacttt acgggtcctt   48480
tccggtgatc cgacaggtta cg                                             48502
```

<210> SEQ ID NO 3
<211> LENGTH: 12
<212> TYPE: DNA
<213> ORGANISM: Artificial Sequence
<220> FEATURE:
<223> OTHER INFORMATION: Sticky overhang

<400> SEQUENCE: 3
gggcggcgac ct                                                        12

<210> SEQ ID NO 4
<211> LENGTH: 12
<212> TYPE: DNA
<213> ORGANISM: Artificial Sequence
<220> FEATURE:
<223> OTHER INFORMATION: Sticky overhang

<400> SEQUENCE: 4
aggtcgccgc cc                                                         12

<210> SEQ ID NO 5
<211> LENGTH: 7249
<212> TYPE: DNA
<213> ORGANISM: Bacteriophage M13mp18

<400> SEQUENCE: 5

| | | | | |
|---|---|---|---|---|
| aatgctacta | ctattagtag | aattgatgcc | acctttcag | ctcgcgcccc | aaatgaaaat | 60 |
| atagctaaac | aggttattga | ccatttgcga | aatgtatcta | atggtcaaac | taaatctact | 120 |
| cgttcgcaga | attgggaatc | aactgttaca | tggaatgaaa | cttccagaca | ccgtacttta | 180 |
| gttgcatatt | taaaacatgt | tgagctacag | caccagattc | agcaattaag | ctctaagcca | 240 |
| tccgcaaaaa | tgacctctta | tcaaaaggag | caattaaagg | tactctctaa | tcctgacctg | 300 |
| ttggagtttg | cttccggtct | ggttcgcttt | gaagctcgaa | ttaaaacgcg | atatttgaag | 360 |
| tctttcgggc | ttcctcttaa | tctttttgat | gcaatccgct | ttgcttctga | ctataatagt | 420 |
| cagggtaaag | acctgatttt | tgatttatgg | tcattctcgt | tttctgaact | gtttaaagca | 480 |
| tttgagggg | attcaatgaa | tatttatgac | gattccgcag | tattggacgc | tatccagtct | 540 |
| aaacatttta | ctattacccc | ctctggcaaa | acttcttttg | caaaagcctc | tcgctatttt | 600 |
| ggtttttatc | gtcgtctggt | aaacgagggt | tatgatagtg | ttgctcttac | tatgcctcgt | 660 |
| aattcctttt | ggcgttatgt | atctgcatta | gttgaatgtg | gtattcctaa | atctcaactg | 720 |
| atgaatcttt | ctacctgtaa | taatgttgtt | ccgttagttc | gttttattaa | cgtagatttt | 780 |
| tcttcccaac | gtcctgactg | gtataatgag | ccagttctta | aaatcgcata | aggtaattca | 840 |
| caatgattaa | agttgaaatt | aaaccatctc | aagcccaatt | tactactcgt | tctggtgttt | 900 |
| ctcgtcaggc | aagccttatt | cactgaatga | gcagctttgt | tacgttgatt | tgggtaatga | 960 |
| atatccggtt | cttgtcaaga | ttactcttga | tgaaggtcag | ccagcctatg | cgcctggtct | 1020 |
| gtacaccgtt | catctgtcct | ctttcaaagt | tggtcagttc | ggttccctta | tgattgaccg | 1080 |
| tctgcgcctc | gttccggcta | agtaacatgg | agcaggtcgc | ggatttcgac | acaatttatc | 1140 |
| aggcgatgat | acaaatctcc | gttgtacttt | gtttcgcgct | tggtataatc | gctggggtc | 1200 |
| aaagatgagt | gttttagtgt | attctttcgc | ctctttcgtt | ttaggttggt | gccttcgtag | 1260 |
| tggcattacg | tattttaccc | gtttaatgga | aacttcctca | tgaaaaagtc | tttagtcctc | 1320 |
| aaagcctctg | tagccgttgc | taccctcgtt | ccgatgctgt | ctttcgctgc | tgagggtgac | 1380 |
| gatcccgcaa | aagcggcctt | taactccctg | caagcctcag | cgaccgaata | tatcggttat | 1440 |
| gcgtgggcga | tggttgttgt | cattgtcggc | gcaactatcg | gtatcaagct | gtttaagaaa | 1500 |
| ttcacctcga | aagcaagctg | ataaaccgat | acaattaaag | gctccttttg | gagccttttt | 1560 |
| ttttggagat | tttcaacgtg | aaaaaattat | tattcgcaat | ccttttagtt | gttcctttct | 1620 |
| attctcactc | cgctgaaact | gttgaaagtt | gtttagcaaa | accccataca | gaaaattcat | 1680 |
| ttactaacgt | ctggaaagac | gacaaaactt | tagatcgtta | cgctaactat | gagggttgtc | 1740 |
| tgtggaatgc | tacaggcgtt | gtagtttgta | ctggtgacga | aactcagtgt | tacggtacat | 1800 |
| gggttcctat | tgggcttgct | atccctgaaa | atgagggtgg | tggctctgag | ggtggcggtt | 1860 |
| ctgagggtgg | cggttctgag | ggtggcggta | ctaaacctcc | tgagtacggt | gatacaccta | 1920 |
| ttccgggcta | tacttatatc | aaccctctcg | acggcactta | tccgcctggt | actgagcaaa | 1980 |
| accccgctaa | tcctaatcct | tctcttgagg | agtctcagcc | tcttaatact | ttcatgtttc | 2040 |

```
agaataatag gttccgaaat aggcaggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgaag    2220
atccattcgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgaggagg cggttccgg tggtggctct ggttccggtg     2400
attttgatta tgaaaagatg gcaaacgcta ataagggggc tatgaccgaa aatgccgatg    2460
aaaacgcgct acagtctgac gctaaaggca aacttgattc tgtcgctact gattacggtg    2520
ctgctatcga tggttttcatt ggtgacgttt ccggccttgc taatggtaat ggtgctactg   2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttag cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttactttct    2940 taaaagggc ttcggtaaga tagctattgc tatttcattg tttcttgctc ttattattgg     3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttctagt aattatgatt     3840 ccggtgttta ttcttatttta acgccttatt tatcacacgg tcggtatttc aaaccattaa   3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
```

```
gttttacgtg ctaataattt tgatatggtt ggttcaattc cttccataat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgcaccta aagatatttt agataacctt cctcaattcc tttctactgt tgatttgcca    4800
actgaccaga tattgattga gggtttgata tttgaggttc agcaaggtga tgctttagat    4860 tttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca aagggttct atctctgttg gccagaatgt cccttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caagattctg gcgtaccgtt cctgtctaaa    5400
atccctttaa tcggcctcct gtttagctcc cgctctgatt ccaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggttttc gccctttgac    5760 gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcgctgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360 atccccctt cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac ggtcgtcgtc ccctcaaact    6540
ggcagatgca cggttacgat gcgcccatct acaccaacgt aacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa cgcgaatttt aacaaaatat taacgtttac    6780
```

-continued

```
aatttaaata tttgcttata caatcttcct gtttttgggg cttttctgat tatcaaccgg    6840
ggtacatatg attgacatgc tagttttacg attaccgttc atcgattctc ttgtttgctc    6900
cagactctca ggcaatgacc tgatagcctt tgtagatctc tcaaaaatag ctaccctctc    6960
cggcattaat ttatcagcta gaacggttga atatcatatt gatggtgatt tgactgtctc    7020
cggcctttct cacccttttg aatctttacc tacacattac tcaggcattg catttaaaat    7080
atatgagggt tctaaaaatt tttatccttg cgttgaaata aaggcttctc ccgcaaaagt    7140
attacagggt cataatgttt ttggtacaac cgatttagct ttatgctctg aggctttatt    7200
gcttaatttt gctaattctt tgccttgcct gtatgattta ttggatgtt               7249

<210> SEQ ID NO 6
<211> LENGTH: 12
<212> TYPE: DNA
<213> ORGANISM: Bacteriophage M13mp18

<400> SEQUENCE: 6
ctcgcgcccc aa                                                         12

<210> SEQ ID NO 7
<211> LENGTH: 17
<212> TYPE: DNA
<213> ORGANISM: Bacteriophage M13mp18

<400> SEQUENCE: 7
atgctctgag gctttta                                                    17

<210> SEQ ID NO 8
<211> LENGTH: 12
<212> TYPE: DNA
<213> ORGANISM: Artificial Sequence
<220> FEATURE:
<223> OTHER INFORMATION: M13 complementary sequence

<400> SEQUENCE: 8
gagcgcgggg tt                                                         12

<210> SEQ ID NO 9
<211> LENGTH: 17
<212> TYPE: DNA
<213> ORGANISM: Artificial Sequence
<220> FEATURE:
<223> OTHER INFORMATION: Oligomer

<400> SEQUENCE: 9
tacgagactc cgaaaat                                                    17
```

CELLULAR PHONE BASED OPTICAL DETECTION OF SPECIFIC NUCLEIC ACID SEQUENCES

DOMESTIC PRIORITY

This application is a continuation of U.S. patent application Ser. No. 14/725,668, filed May 29, 2015, the disclosure of which is incorporated by reference herein in its entirety.

BACKGROUND

The present invention relates to nucleic acid sequences, and more specifically, to optical detection of specific nucleic acid sequences.

A nucleic acid sequence is a succession of letters that indicate the order of nucleotides within a deoxyribonucleic acid (DNA) (using G, A, C, and T) or ribonucleic (RNA) (G, A, C and U) molecule. By convention, sequences are usually presented from the 5' end to the 3' end.

Deoxyribonucleic acid (DNA) is a molecule that encodes the genetic instructions used in the development and functioning of all known living organisms and viruses. Ribonucleic acid (RNA) is a polymeric molecule. It is implicated in various biological roles in coding, decoding, regulation, and expression of genes.

SUMMARY

According to one embodiment, a method is provided to determine a presence of a known nucleic acid sequence of a known molecule in a sample in which the sample contains a targeted nucleic acid sequence. The method includes coating a sample surface with a select segment of the known molecule, where the sample surface is configured to hold a liquid medium, and coating a plurality of beads with a first molecule. The method includes attaching the targeted nucleic acid sequence to a second molecule that is configured to bind to the first molecule, such that the targeted nucleic acid sequence is attached to the plurality of beads via the first and second molecules, and placing the sample on the sample surface. The sample includes the liquid medium, the plurality of beads, and the targeted nucleic acid sequence being tested for having the known nucleic acid sequence of the known molecule. The targeted nucleic acid sequence is unknown. Also, the method includes video monitoring a Brownian motion of the plurality of beads with an optical device, and determining whether the Brownian motion of the plurality of beads in the liquid medium is restricted or not restricted over time. In response to determining that the Brownian motion of the plurality of beads is restricted, the presence of the known nucleic acid sequence is recognized to be in the sample, thus indicating that the targeted nucleic acid sequence is the known nucleic acid sequence. In response to determining that the Brownian motion is not restricted, it is recognized that the known nucleic acid sequence is not present in the sample, thus indicating that the targeted nucleic acid sequence is not the known nucleic acid sequence.

According to one embodiment, a system is provided to determine a presence of a known nucleic acid sequence of a known molecule in a sample in which the sample contains a targeted nucleic acid sequence. The system includes a sample surface configured to receive the sample, and the sample surface is coated with a select segment of the known molecule. The sample includes a plurality of beads coated with a first molecule, and the targeted nucleic acid sequence attached to a second molecule that is configured to bind to the first molecule, such that the targeted nucleic acid sequence is attached to the plurality of beads via the first and second molecules. The targeted nucleic acid sequence is being tested for having the known nucleic acid sequence of the known molecule, and the targeted nucleic acid sequence is unknown. The sample also includes a liquid medium. Also, the system includes an electronic communication device configured to video monitor a Brownian motion of the plurality of beads, and determine whether the Brownian motion of the plurality of beads in the liquid medium is restricted or not restricted over time. The electronic communication device is configured to in response to determining that the Brownian motion of the plurality of beads is restricted, recognize the presence of the known nucleic acid sequence in the sample, thus indicating that the targeted nucleic acid sequence is the known nucleic acid sequence. Also, the electronic communication device is configured to in response to determining that the Brownian motion is not restricted, recognize that the known nucleic acid sequence is not present in the sample, thus indicating that the targeted nucleic acid sequence is not the known nucleic acid sequence.

According to one embodiment, an electronic communication device is provided to determine a presence of a known nucleic acid sequence of a known molecule in a sample in which the sample contains a targeted nucleic acid sequence. The electronic communication device includes a processing circuit and a non-transitory storage medium readable by the processing circuit and storing instructions that, when executed by the processing circuit, cause the processing circuit to perform operations. The processing circuit performs operations of video monitoring of a Brownian motion of a plurality of beads attached to the targeted nucleic acid sequence, and determining whether the Brownian motion of the plurality of beads in a liquid medium is restricted or not restricted over time. The processing circuit performs operations of in response to determining that the Brownian motion of the plurality of beads is restricted, recognizing the presence of the known nucleic acid sequence in the sample, thus indicating that the targeted nucleic acid sequence is the known nucleic acid sequence. The processing circuit performs operations of in response to determining that the Brownian motion is not restricted, recognizing that the known nucleic acid sequence is not present in the sample, thus indicating that the targeted nucleic acid sequence is not the known nucleic acid sequence.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 7E-1 and 7E-2 are histogram graphs illustrating bead displacement in bead positions between two consecutive video frames for x-positions and y-positions, respectively, according to an embodiment;

FIGS. 7F-1 and 7F-2 are histogram graphs illustrating bead displacement in bead positions between two consecutive video frames for x-positions and y-positions, respectively, according to an embodiment;

FIGS. 7G-1 and 7G-2 are histogram graphs illustrating bead displacement in bead positions between two consecutive video frames for x-positions and y-positions, respectively, according to an embodiment;

FIG. 8A-1 is an original fluorescent image illustrating micron size beads according to an embodiment;

FIG. 8A-2 is a processed fluorescent image of the micron size beads identifying bead positions between two consecutive video frames;

FIG. 8C-1 is an image illustrating bright spots identified as bead positions according to an embodiment;

FIG. 8C-2 is a histogram graph illustrating the distribution of found circle radii in pixels for the image in FIG. 8C-1 according to an embodiment;

FIG. 8D-1 is a histogram graph of the distribution of total displacement in bead positions between two consecutive video frames for x-positions according to an embodiment;

FIG. 8D-2 is a histogram graph of the distribution of total displacement in bead positions between the two consecutive video frames for y-positions according to an embodiment;

FIG. 8E-1 is a histogram graph of the distribution of total x-displacement in bead positions between two consecutive video frames according to an embodiment;

FIG. 8E-2 is a histogram graph of the distribution of total y-displacement in bead positions between two consecutive video frames according to an embodiment;

FIG. 9B-1 is the band-pass filtered image and identified bead positions according to an embodiment;

FIG. 9B-2 is a zoomed in view of the band-pass filtered image according to an embodiment;

FIG. 9C-1 is a histogram graph illustrating the distribution bead positions for x-positions as shifted between two frames which fits a Gaussian distribution as expected for the random displacement of the beads according to an embodiment;

FIG. 9C-2 is a histogram graph illustrating the distribution bead positions for x-positions as shifted between two frames which fits a Gaussian distribution as expected for the random displacement of the beads according to an embodiment;

FIG. 9C-3 is a histogram graph illustrating the distribution bead positions for y-positions as shifted between two frames which fits a Gaussian distribution as expected for the random displacement of the beads according to an embodiment;

DETAILED DESCRIPTION

Figure 1:
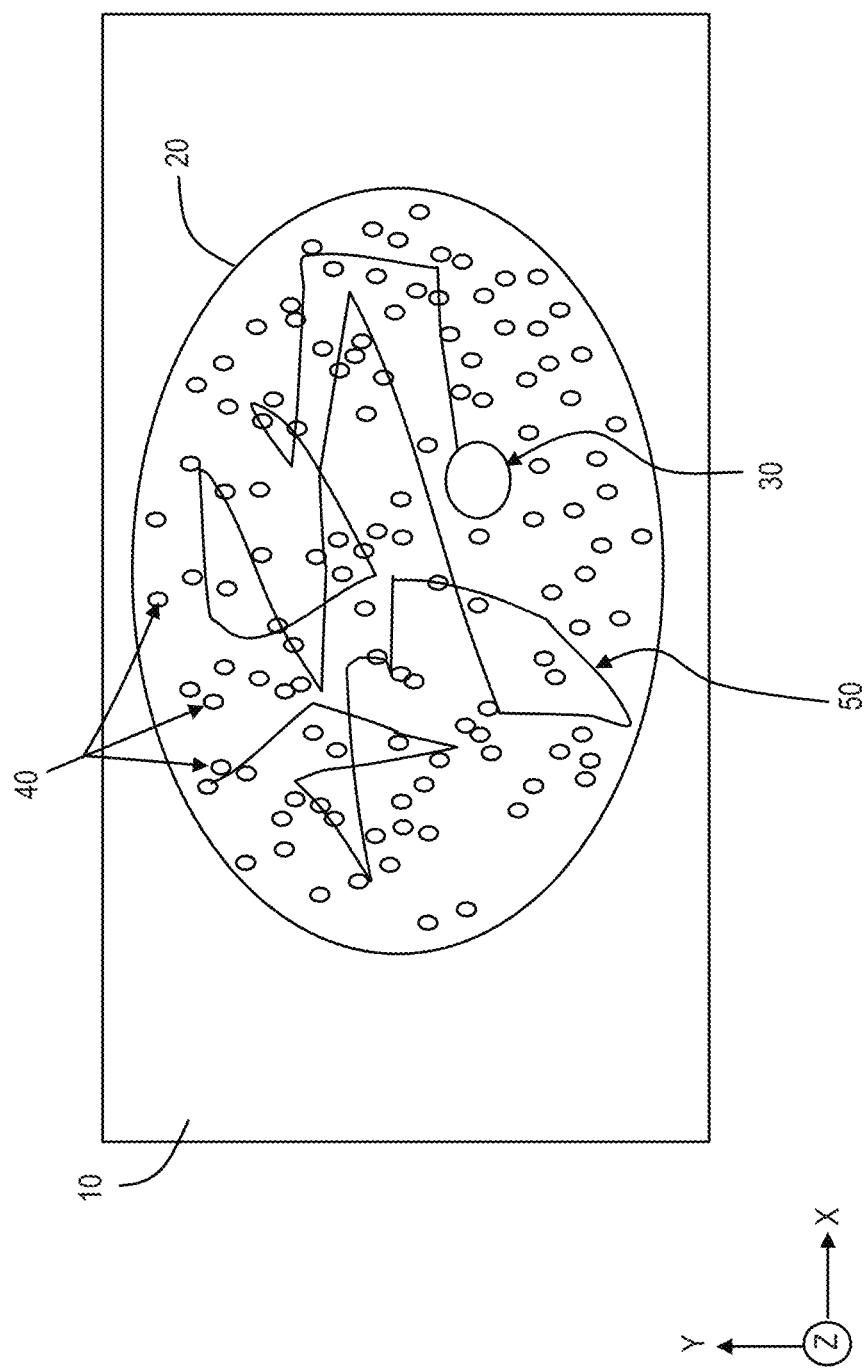
FIG. 1 illustrates a sample surface with a liquid on the sample surface according to an embodiment.

Embodiments provide techniques to detect the presence or absence of a specific nucleic acid sequence, such as DNA and RNA, in a targeted/unknown molecule being tested.

There are times when one needs to know whether a sample, which may be any item or substance being tested, contains a known nucleic acid sequence. For example, Europe and now the U.S. have begun requiring labelling of genetically modified (GM) food. One may not know whether a shipment of corn was actually from non-GM plants or GM plants. In another scenario, individuals with Celiac disease become sick if they eat gluten. How would a person know if this 'gluten-free' product really contains gluten? It is possible that products can be fraudulent or health hazards but individuals may not know.

Embodiments provide techniques to detect the presence or absence of a specific nucleic acid sequence, such as DNA and RNA, in a sample being tested. Accordingly, embodiments can identify the presence of pathogens, viruses, organisms, particular DNA and RNA molecules, etc., using optical detection on a device, such as, e.g., a cellular phone (also referred to as mobile phones, smart phones, mobile devices, etc.).

Embodiments are based on detecting the restricted Brownian motion of microparticles which can be applied to detect the genetic material (DNA/RNA) of flu and other viruses, bacteria, and other organisms. Because embodiments are based on the complementary metal-oxide-semiconductor (CMOS) sensor in a mobile phone (or other device), some embodiments can be fabricated on a silicon chip with integrated optical components to make low-cost, compact, and portable biosensing chips. Due to their portability and compactness, these biosensing chips can have wide applicability in the developing countries where quick and fast diagnosis can be made with these devices while using limited resources.

The current mobile phone user market is huge and the number of mobile phone users has reached 5 billion in 2010. The majority of these users are in the developing countries. Moreover, it is estimated that there will be 8 billion smart phone users with connected health and wellness service by 2018. This scenario offers a tremendous opportunity for developing smart-phone based biosensors delivering health care related information, for example, identifying if a person has the flu or not, performing a cholesterol test, and so on. Smart phones are built with a good complementary metal-oxide-semiconductor (CMOS) sensors having high image capturing and processing capabilities, for example iPhone® 5, 5C, and 6, and this offers a great opportunity for use in embodiments discussed herein. There is a growing need for quick and easy diagnosis of flu-like symptoms with point-of-care diagnostic kits at one's home, away from the doctor's office, or at an epidemic center. This is also highlighted by the recent epidemic associated with the Ebola virus. There have been recent advances made by researchers in developing mobile-phone based sensing devices, for example, for flow cytometry analysis and polymerase chain reaction (PCR) based DNA detection. However, embodiments apply techniques using the Brownian motion of microparticles to detect the presence of DNA or RNA molecules specific to a known DNA sequence such as, for example, the flu type virus.

For ease of understanding, sub-headings are utilized. It is understood that the sub-headings are meant for explanation purposes and not limitation.

Brownian Motion

Colloidal or polymer particles of micron size undergo random motion in a liquid (also referred to as a medium or solution), and this random motion is characteristic of the Brownian motion. Brownian motion can also be observed in air, for example, by watching small pollen grains or dust particles suspended in air shined by a beam of sun light. In both cases, the origin of their random motion can be explained by the random motion of the underlying much smaller molecules that make up either the air or liquid. As these small molecules constantly collide with the bigger particles embedded in them, at any moment there is imbalance in the net force impacted by these small molecules on the bigger particles. This imbalance in the net force results in the movement of the bigger particles and results in the net force being random in direction and magnitude. Therefore, the imbalance in the net force causes random movement of the bigger particles. It follows that in order for this random motion to be detectable macroscopically, for example, either with naked eye or with a simple optical microscope, the size of the bigger particles cannot be too big compared to the size of the small molecules. The Brownian motion of particles in three dimensions is well described by a simple equation for mean-square displacement (MSD):

$$\delta x^2 = 6Dt$$

where t is time. The MSD used in Statistical mechanical description of particle motion is defined as:

$$\{x(t)-x(0)\}^2$$

where x(t) represents the position of the particle at time t, x(0) initial position and the angled brackets represent time average. Supposing one knows the positions of a particle over a time duration at an interval $\delta t$, then MSD can be calculated from the equation:

$$\delta x^2 = [(x(t_1)-x(0))^2 + (x(t_2)-x(0))^2 + (x(t_3)-x(0))^2 + \ldots + (x(t_n)-x(0))^2]/n$$

Where n is the number of consecutive positions of the particle.

The only constant in this equation that characterizes the particle is the diffusion constant, D. The diffusion constant D can be calculated from Einstein's relation $$D = \mu k_B T$$

where $k_B$ is the Boltzmann constant, $\mu$ is the mobility of the diffusing particle, and T is the temperature of the medium (liquid) the particle is diffusing in.

For a spherical particle, the mobility can be calculated from Stokes law for the drag force on the particle and Einstein's relation simplifies to $$D = \frac{k_B T}{6\pi \eta r}$$

where 'r' is the radius of the particle, $\eta$ is the dynamic viscosity of the medium (liquid). In addition to the simple equation that can be used to calculate the diffusion coefficient D of the particle, experimentally measured values are also widely available for polymer micro-beads and DNA molecules. So given the temperature T and the nature of the medium (e.g., the dynamic viscosity $\eta$) in which the particle is present, the mean-square displacement ($\delta x^2$) of the particle can be calculated and will be linear in time duration of the observation of the particle.

In the case of experiments tracking particle motion either by cellular-phone based microscopes or research microscopes with high numerical aperture, since the particle position is detected only in a two-dimensional plane, the equation for MSD corresponds to two-dimensional diffusion which is $\delta x^2 = 4Dt$. Because of this difference in the coefficients, the diffusion constant for two-dimensional diffusion will be larger than for three-dimensional diffusion.

FIG. 1 illustrates a sample surface 10 with a liquid 20 on the sample surface 10 according to an embodiment. An example micron size bead 30 is in the liquid 20. The liquid 20 is made up of small molecules 40. The micron size bead 30 is representative of the bigger particle in the liquid of the small molecules 40. As discussed above, the small molecules 40 bombard the bead 30 and exert a net force on the bigger bead 30. The bigger bead 30 travels in a random direction according to Brownian motion and the random direction previously traveled by the bigger bead 30 is shown by a displacement trace/line 50. FIG. 1 shows an example with a single micron bead 30 for ease of understanding, but it should be appreciated that the same analogy applies for numerous beads 30 in the liquid 20.

Detection of Specific DNA/RNA Sequences

Figure 2:
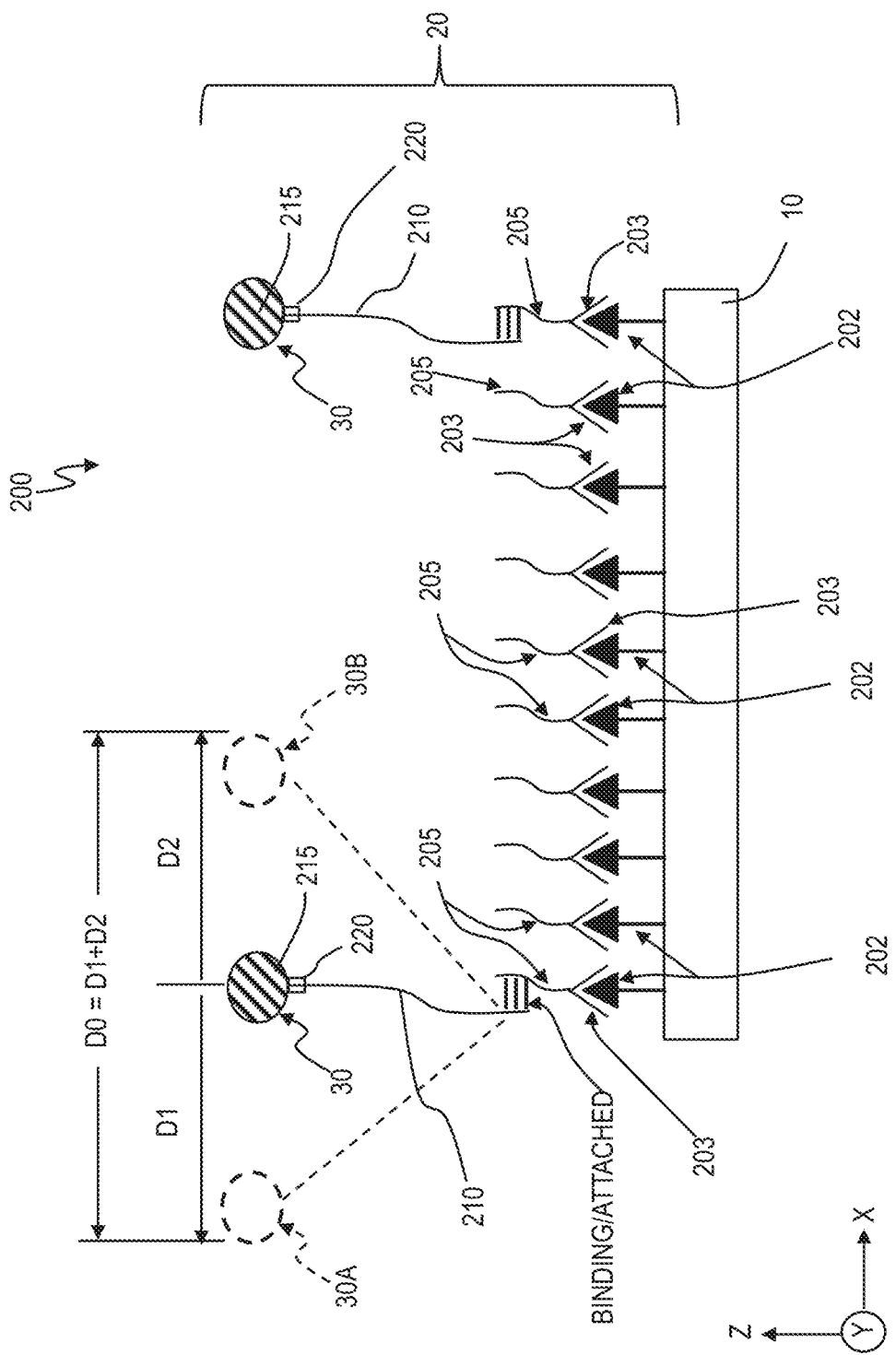
FIG. 2 is a cross-sectional view of a system utilized for detection of a specific DNA sequence within an unknown DNA molecule being tested according to an embodiment.

The mean-square displacement ($\delta x^2$) of a free Brownian particle (such as the bead 30) keeps increasing linearly with time as was just discussed. However, if the particle is tethered at one end to the surface of the sample container, then the particle's motion will be restricted by the tether length according to embodiments, as shown in FIG. 2. This effect can be exploited to detect the presence of a DNA sequence in the following way.

FIG. 2 is a cross-sectional view of a system 200 utilized for detection of a specific DNA sequence in an unknown DNA molecule 210 being tested according to an embodiment. For the sake of clarity and simplicity, the small molecules 40 of the liquid 20 are not shown in subsequent figures. Also, for explanation purposes, only two beads 30 are illustrated but it should be appreciated that numerous micron size beads (e.g., 100-1000) may be utilized in embodiments.

In FIG. 2, the unknown DNA molecule 210 has a nucleic acid sequence that needs to be detected, and the unknown DNA molecule 210 is the molecule being tested. The unknown DNA molecule 210 may be the DNA/RNA of a virus, pathogen, a food product, etc., which needs to be tested. The unknown DNA molecule 210 is to be tested against a short segment of its complementary sequence. This segment can be of 8 to 40 bases long and chosen such that the double-stranded DNA that it forms with the unknown DNA molecule 210 will have sufficiently higher melting temperature than the temperature at which the experiments are carried out. The melting points of such segments can be calculated by methods based on nearest-neighbor interactions of the nucleic acid bases described by other researchers and their later improvements. (John SantaLucia Jr. (1998). "A unified view of polymer, dumbbell, and oligonucleotide DNA nearest-neighbor thermodynamics". *Proc. Natl. Acad. Sci. USA* 95 (4): 1460-5. doi:10.1073/pnas.95.4.1460; Breslauer, K.J.; Frank, R; Blöcker, H; Marky, LA et al. (1986). "Predicting DNA Duplex Stability from the Base Sequence". *Proc. Natl. Acad. Sci. USA*. 83 (11): 3746-3750. doi:10.1073/pnas.83.11.3746). They are also available as open-access software tools such as Oligo Solver 3.0 (Integrated DNA Technologies. While designing these short segments their tendency to form partial double-strand DNA segments due to self-hybridization can be calculated using DINA Melt web server. It makes computational folding studies of the possible self-hybridization pairs and calculates the melting temperatures of such configurations. Keeping in mind both the high melting temperature of the double-strand segment formed with the unknown DNA molecule and minimal tendency for self-hybridization the sequence of the short segment DNA can be designed. As such, the unknown DNA molecules 210 are the sample being tested in the liquid 20.

The DNA molecule 210, having a sequence that needs to be detected, can be attached to the beads 30 at one end by using beads 30 coated with a first molecule 215 represented as diagonal lines. The molecule 215 is chosen to attach to the material of the beads 30. In one implementation to attach the first molecule 215 to the beads 30, the beads 30 may be polystyrene beads and the coated molecule 215 may be the protein (molecule) streptavidin. The protein streptavidin is coated on and binds to the beads 30.

In another implementation, the material of the beads 30 may be poly-methyl-methacrylate (PMMA) beads in the size range of 0.2 to 2.0 microns such as those available from any of these commercial vendors: Bangs Labs, Life Technologies and PolySciences and the first molecule 215 may be streptavidin protein molecules, such that the first molecule 215 binds to the beads 30.

In yet another implementation, the material of the beads 30 may be silica (SiO$_2$) beads in the size range of 0.2 to 2.0 microns such as those available from any of these commercial vendors: Bangs Labs, Life Technologies and PolySciences and the first molecule 215 may be streptavidin protein molecules, such that the first molecule 215 binds to the beads 30.

In order to facilitate the DNA molecule 210 attaching to the bead 30 coated with molecule 215, the end of the DNA molecule 210 is attached with a second molecule 220 that is designed/chosen to attach to the first molecule 215 (e.g., streptavidin). The second molecule 220 has a dual purpose, which is 1) to bind to the unknown DNA molecule 210 and 2) to bind to the first molecule 215. Similarly, the first molecule 215 has a dual purpose, which is 1) to bind to the bead 30 and 2) to bind to the second molecule 220.

In one implementation, the second molecule 220 may be a biotin molecule that will bind to the streptavidin molecules 215 (i.e., first molecules 215) coated on the bead surface of bead 30. Accordingly, this (combination of the first molecule 215 and second molecule 220) forms DNA molecules 210 attached at one end to the bead surface 30.

In FIG. 2, the sample surface 10 (such as, e.g., a microscope glass slide after some pre-cleaning if necessary) is coated with antibodies 202 that will bind to Digoxigenin molecules 203. The short probe DNA molecules 205 are attached with Digoxigenin molecules 203 on one end (could be short probe RNA molecules when testing an unknown RNA molecule or RNA molecule attached with short probe DNA molecule). The short probe DNA molecules 205 contain a segment of the complementary sequence for a known DNA/RNA molecule, which means that the short probe DNA molecules 205 (complementary sequence) is expected/known in advance to attach to the known DNA molecule (e.g., a known virus being tested). Therefore, if the free end (the end not attached to the bead surface 30) of the unknown DNA molecule 210 binds to the short probe DNA molecules 205 (i.e., complementary sequence of a segment of the known molecule), the unknown DNA molecule 210 is the same as the known DNA molecule. Because by choice, the sequence of the short probe DNA molecule 205 is chosen such that to a very high degree it (the sequence of the short probe DNA molecule 205) belongs only to the known DNA molecule. The converse is also true. If the free end (the end not attached to the bead surface 30) of the unknown DNA molecule 210 does not bind to the short probe DNA molecules 205 (i.e., complementary sequence of a segment of the known molecule), the unknown DNA molecule 210 is not the same as the known DNA molecule.

As the DNA-attached bead 30 comes in contact with this short probe DNA molecule 205, the unknown DNA molecules 210 form the tether thereby restricting the Brownian motion of the DNA-attached bead 30. Therefore, the presence of a specific DNA sequence (in the unknown DNA molecule 210 ) of the DNA-attached bead 30 can be detected (indirectly).

The short probe DNA molecules 205 are known and may be the DNA molecules of the virus, pathogen, food product, etc., that is being tested for. Since the short probe DNA molecules 205 are the complementary sequence of what the unknown DNA molecule 210 should be, the short probe DNA molecules 205 are designed to bind to the expected (but unknown) sequence of the DNA molecule 210 . When the DNA molecules 210 are the complementary sequence to the short probe DNA molecules 205, the two DNA molecules 205 and 210 bind to form a double strand DNA molecule. In a DNA double helix, each type of nucleobase on one strand binds with just one type of nucleobase on the other strand. This is called Watson-Crick or complementary base pairing. The short probe DNA molecules 205 are single strand DNA molecules, while the tested DNA molecules 210 are single strand DNA molecules. One skilled in the art understands how to prepare complementary DNA sequences, single strand DNA, and short DNA probes.

In one embodiment, single-stranded DNA molecules 210 made of the same type of bases (A, T, G or C) can be used for detecting their binding to the beads 30 and the resulting restricted Brownian motion. These homopolymer DNA molecules can be custom-made with a pre-attached Digoxigenin molecule at one end and the biotin molecule at the other end. Here is one example of such a DNA molecule: Digoxigenin-C6-amino-(TTTTTTTTTT)$_{15}$-3'-biotin (SEQ ID NO. 1). These molecules consisting of 150 Thymine bases can be obtained from commercial vendors (Midland Certified Reagent Company Inc™, Midland, Tex. and Integrated DNA Technologies, Inc™, Coralville, Iowa). These DNA molecules 210 can be attached to the beads 30 coated with streptavidin molecules through biotin molecules 220 in one end of them. The DNA-attached beads will be filled in the sample chamber to test their binding to the antibody molecules coated on the glass surface of the sample cell through the Digoxigenin molecules at the other end of the DNA molecules.

In another embodiment, long double-stranded DNA molecule from bacteriophage viruses can be used as DNA molecules 210. The linear lambda-DNA (SEQ ID NO. 2) extracted which has 48,502 bases can be used (available from New England Biolabs, Inc™, Ipswich, Mass). It has two cohesive or sticky overhangs each 12 bases long at each end. Their sequences are: 5'-GGGC GGCG ACCT-3' (SEQ ID NO. 3) and 5'-AGGT CGCC GCCC-3'. (SEQ ID NO. 4) The short DNA oligomers SEQ ID NO. 3 biotin and SEQ ID NO. Digoxigenin (SEQ ID NO. 3) can be mixed with Lamda DNA one at a time so that one of these DNA oligomers will bind to their sticky ends (can be purchased from Integrated DNA Technologies, Inc™). After attaching one of them they will be ligated to chemically link to the long strands of Lamda DNA to which they attach by complementary pairing. After ligation, for example, the oligomer with the biotin on one end can be mixed with streptavidin coated beads in solution. The DNA attached beads can be isolated by sedimenting the beads by centrifugation and extracting the supernatant solution. These isolated DNA attached beads can be mixed with the Digoxigenin attached oligomers to bind to the other overhang in the Lamda DNA and ligated. At the end, one will have Lamda DNA with Digoxigenin ends that are free to bind to the antibody coated surface.

In yet another embodiment, a single-stranded DNA molecule M13mp18 (SEQ ID NO. 5) from a virus can be utilized as DNA molecules 210. This DNA has 7249 bases and its contour length is about 5 microns which is a sufficiently long tether for the bead. The DNA sequence CTC GCG CCC CAA (SEQ ID NO. 6) occurs near the 5' end of this DNA molecule and has a melting temperature of 51.9C which is much higher than normal operating temperature. The DNA sequence ATG CTC TGA GGC TTT TA (SEQ ID NO. 7) occurs near the 3' end and has a melting temperature of 47.3C much higher than normal operating temperature. Therefore these two sequences can be utilized to design short DNA oligomers attached with biotin and Digoxigenin molecules. The DNA oligomer, Biotin-3'-GAG CGC GGG GTT-5' SEQ ID NO. 8 will form complementary base pairing with the sequence near the 5' end, namely, CTC GCG CCC CAA (SEQ ID NO. 6). The biotin attached to the 3' end will bind to the Streptavidin molecules coated on the beads 30 when mixed with them in solution. In order to break any unwanted hair pin formation in these DNA oligomers the mixture with the beads can be heated above their complementary base pair melting temperature and slowly cooled across their melting zone and then cooled rapidly to either room temperature or quenched in an ice-bath. The other short oligomer 3'-TAC GAG ACT CCG AAA AT-5'-Digoxigenin (SEQ ID NO. 9) can be mixed with the DNA attached beads and will bind to the antibody coated on the sample cell surface thereby forming DNA tethers for the beads 30. The dynamics of binding of either biotin to streptavidin beads or the Digoxigenin to antibody molecules coated on the sample cell surface can be made faster by using a homopolymer spacer between biotin or Digoxigenin and the short oligomer DNA sequence. The length of such homopolymers can be in the range of 20 to 200 bases long. By having the single-strand DNA being much more flexible than double-stranded DNA (persistence length for dsDNA is 50 nm and for ssDNA is ~2 nm which is twenty five times shorter), these homopolymers will let the binding molecules Biotin or Digoxigenin to explore different configurations before they bind to their counterparts (Streptavidin or Antibody molecules as discussed before) accelerating their time for binding.

Figure 3A:
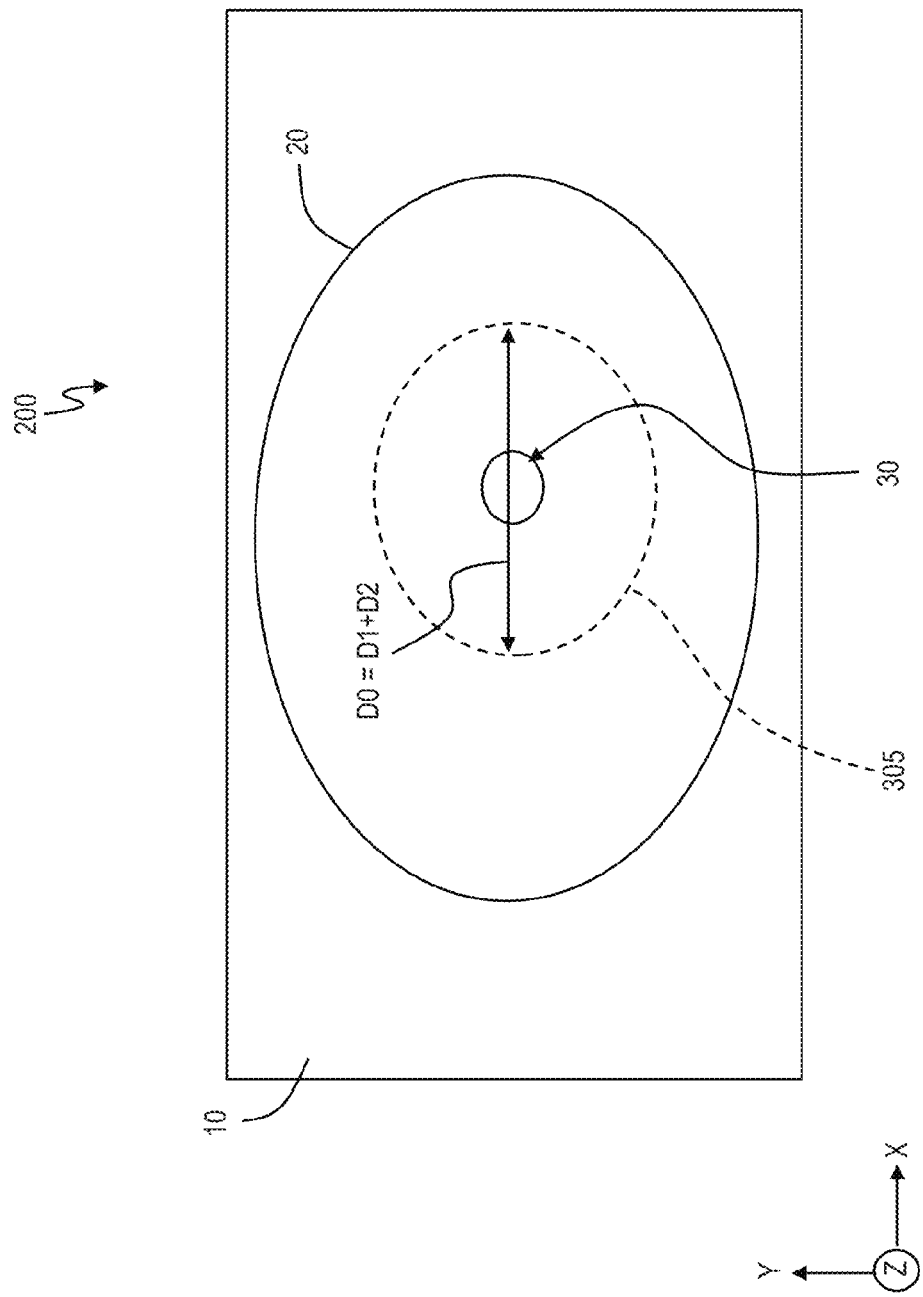
FIG. 3A is a top-down view illustrating that a tethered bead attached via the unknown DNA molecule is confined to motion in a circular shape according to an embodiment.

FIG. 2 shows the DNA molecule 210 attached/bound to the short probe DNA molecule 205, which indicates that the DNA molecule 210 and the short probe DNA molecule 205 are the same molecule. In other words, this means that targeted DNA molecule 210 and the short probe DNA molecule 205 are both from the known molecule (although they may have complimentary nucleic acid sequences). To recognize that the DNA molecule 210 is attached to the short probe DNA molecule 205, the random motion of the beads 30 is monitored. The displacement of untethered beads 30 would be similar to the free Brownian motion of the displacement trace 50 shown in FIG. 1 which does not restrict the space the bead can explore over time. However, when the DNA molecule 210 is attached to both the bead 30 and the short probe DNA molecule 205 (i.e., beads 30 are tethered to the sample surface 10 via the DNA molecule 210 being tested), the bead 30 is restricted to (only) moving to the dashed bead locations 30A and 30B. As one depiction in a two-dimensional space, the tethered beads 30 can move a maximum distance of D1 along the x-axis in one direction, and the tethered beads 30 can move a maximum distance of D2 along the x-axis in the opposite direction. The extent of the movement for the tethered beads 30 in the x-axis is limited to D0=D1+D2, which is based on the length of the DNA molecule 210 (i.e., the tether). By having the bead 30 tethered by the DNA molecule 210, the potential motion, which is limited/restricted Brownian motion of the tethered bead 30, is roughly limited to the volume of a sphere along the x, y, and z axes. FIG. 3A is a top-down view of the system 200 utilized for detection of a specific DNA sequence in the unknown DNA molecule 210 being tested according to an embodiment. FIG. 3A shows that each tethered bead 30 (i.e., when the DNA molecule 210 is attached to both the bead 30 and the short probe DNA molecule 205) may have the limited range of Brownian motion that forms and/or is confined to a circular shape 305 (within the two-dimensional space). The diameter of the circular shape 305 is D0 where D0=D1+D2 as shown in FIG. 2. This limited and restricted Brownian motion, confined to the area of the circular shape 305 (which is a sphere in a three-dimensional space), of the bead 30 tethered to the sample surface 10 (i.e., the short probe DNA molecules 205) by the DNA molecule 210 is determined to be positive identification of the known molecule. In the case when more than one DNA molecule 210 is attached to the bead 30, the motion of the bead can be further restricted to a circular shape with the diameter significantly smaller than D0=D1+D2. This is also a positive identification of the known molecule.

This limited/restricted Brownian motion of the tethered beads 30 can be optically recognized and traced via a cellular phone 401, a charge coupled device (CCD), and/or a microscope. When the limited/restricted Brownian motion of the tethered beads 30 is recognized, it is determined that the tested DNA molecule 210 is the same molecule as the short probe DNA molecule 205. The identification of the short probe DNA molecules 205 are known in advance.

For the sake of clarity and simplicity, the small molecules 40 of the liquid 20, the short probe DNA molecules 205, and the DNA molecules 210 are omitted in FIG. 3A. Also, for explanation purposes, only a single bead 30 is illustrated but it should be appreciated that numerous micron size beads (e.g., 100-1000) may be utilized.

In the case when the unknown DNA molecules 210 do not bind with the short probe DNA molecules 205, this means that the sequence of the unknown DNA molecule 210 is not the complementary sequence to the short probe DNA molecules 205. Therefore, the unknown DNA molecules 210 are not the same molecule as the known short probe DNA molecules 205, and the unknown DNA molecules 210 can be ruled out as being the same molecule as the known molecule (e.g., a particular virus).

Figure 3C:
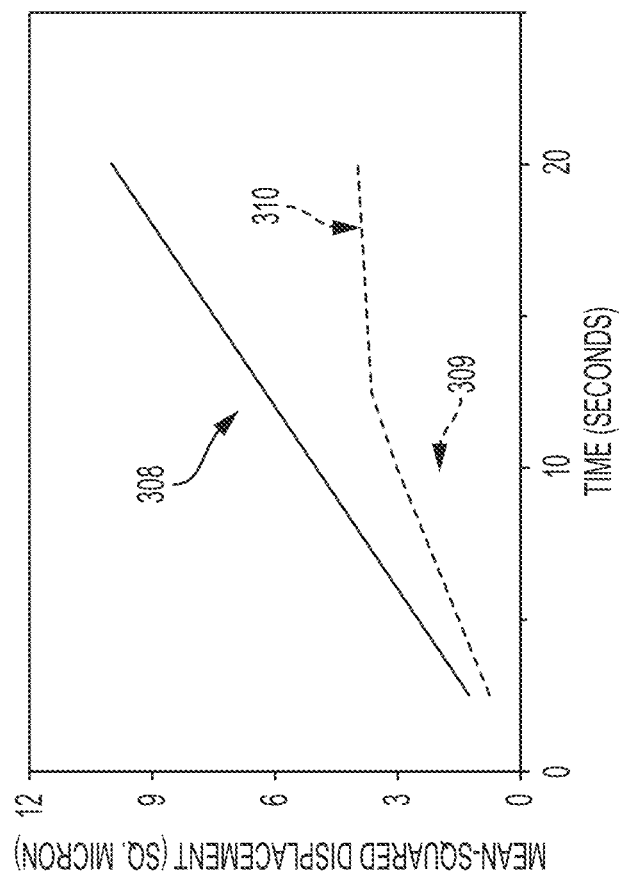
FIG. 3C is graph illustrating the effects of DNA tethering mean-squared displacement according to an embodiment.
Figure 3B:
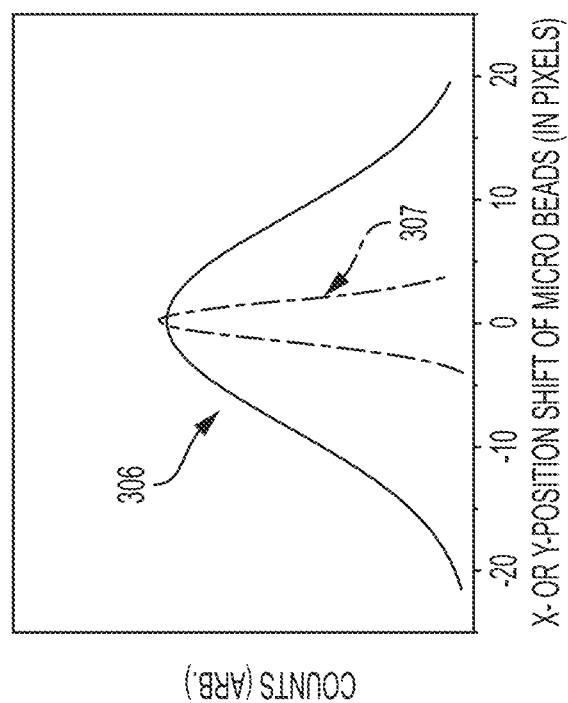
FIG. 3B is graph illustrating the effects of DNA tethering on x and y bead displacement according to an embodiment.

FIG. 3B is graph illustrating the effects of DNA tethering on x and y bead displacement according to an embodiment. In FIG. 3B, waveform 306 illustrates the distribution of the bead x- or y-position displacements due to the free Brownian motion in the absence of tethering by the targeted nucleic acid sequence in the sample. In contrast, waveform 307 shows a much narrower distribution of the bead displacement when tethering is formed by the targeted nucleic acid sequence in the sample.

FIG. 3C is a graph illustrating the effects of DNA tethering mean-squared displacement according to an embodiment. Waveform 308 illustrates the mean-squared displacement of the free beads in two dimensions of their Brownian motion showing that the free beads exhibit linear behavior obeys $\delta x^2 = 4Dt$ where D is the diffusion constant.

In contrast, plot 309 illustrate that, when tethering is formed by the targeted nucleic acid sequence, the tethered beads' motion will be slowed down for smaller displacements resulting in smaller diffusion constant over a shorter time duration. The tethered beads may also exhibit non-linear behavior arising from the polymer elasticity of the tether. Plot 310 illustrates that, on a longer time duration as the beads try to move beyond the length of the tether, they become confined to a circle. This results in the flattening of their mean-squared displacement.

Figure 13:
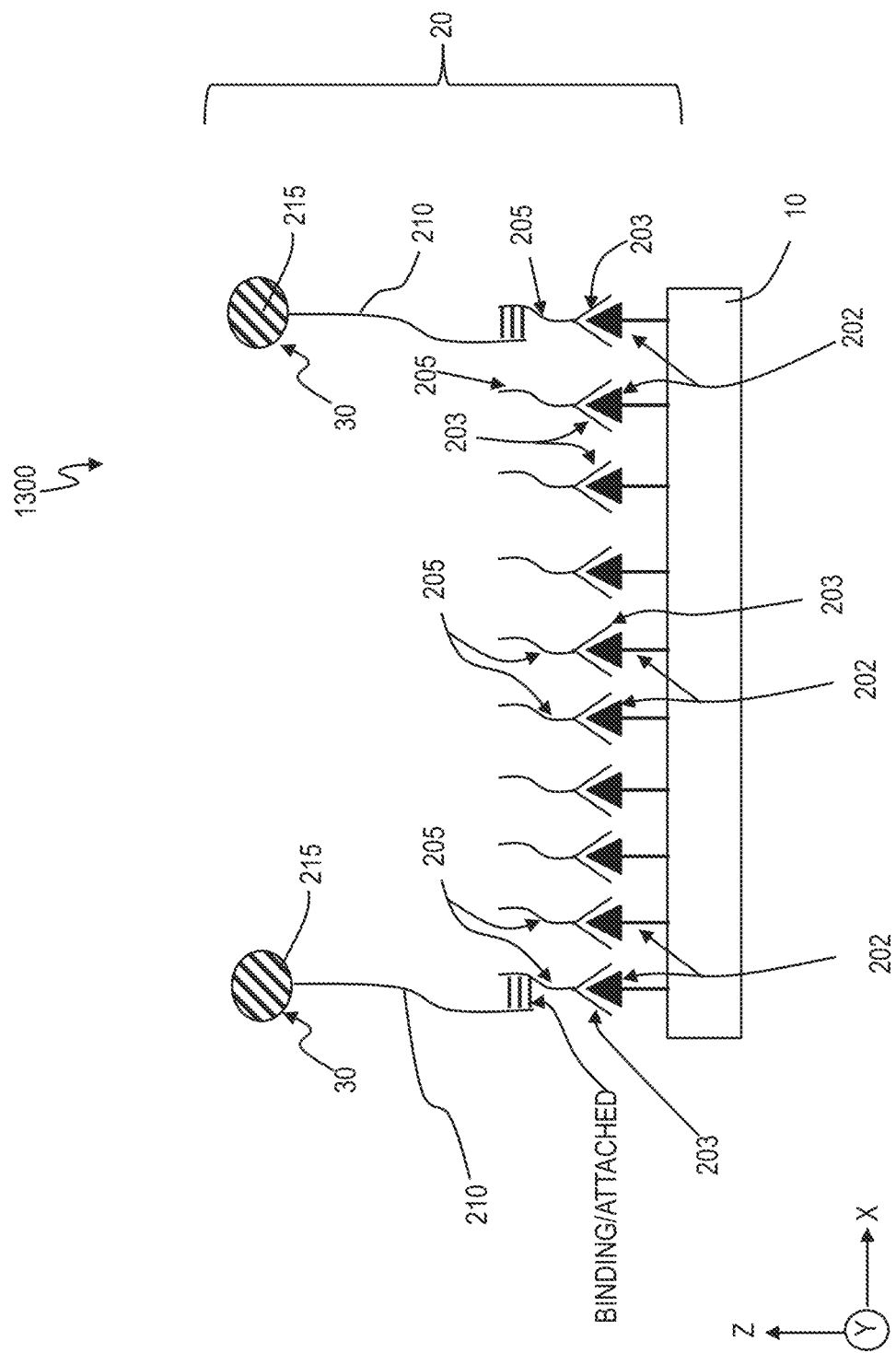
FIG. 13 is a cross-sectional view of a system utilized for detection of a specific DNA sequence within an unknown DNA molecule being tested according to an embodiment.

According to another embodiment, FIG. 13 is a cross-sectional view of a system utilized for detection of a specific DNA sequence within an unknown DNA molecule being tested. FIG. 13 is similar to FIG. 2 except that the second molecule 220 is removed. In this embodiment, one end of the unknown DNA molecule 210 is attached directly to the first molecule 215 (i.e., attached to the beads 30) without the second molecule 220.

Figure 14:
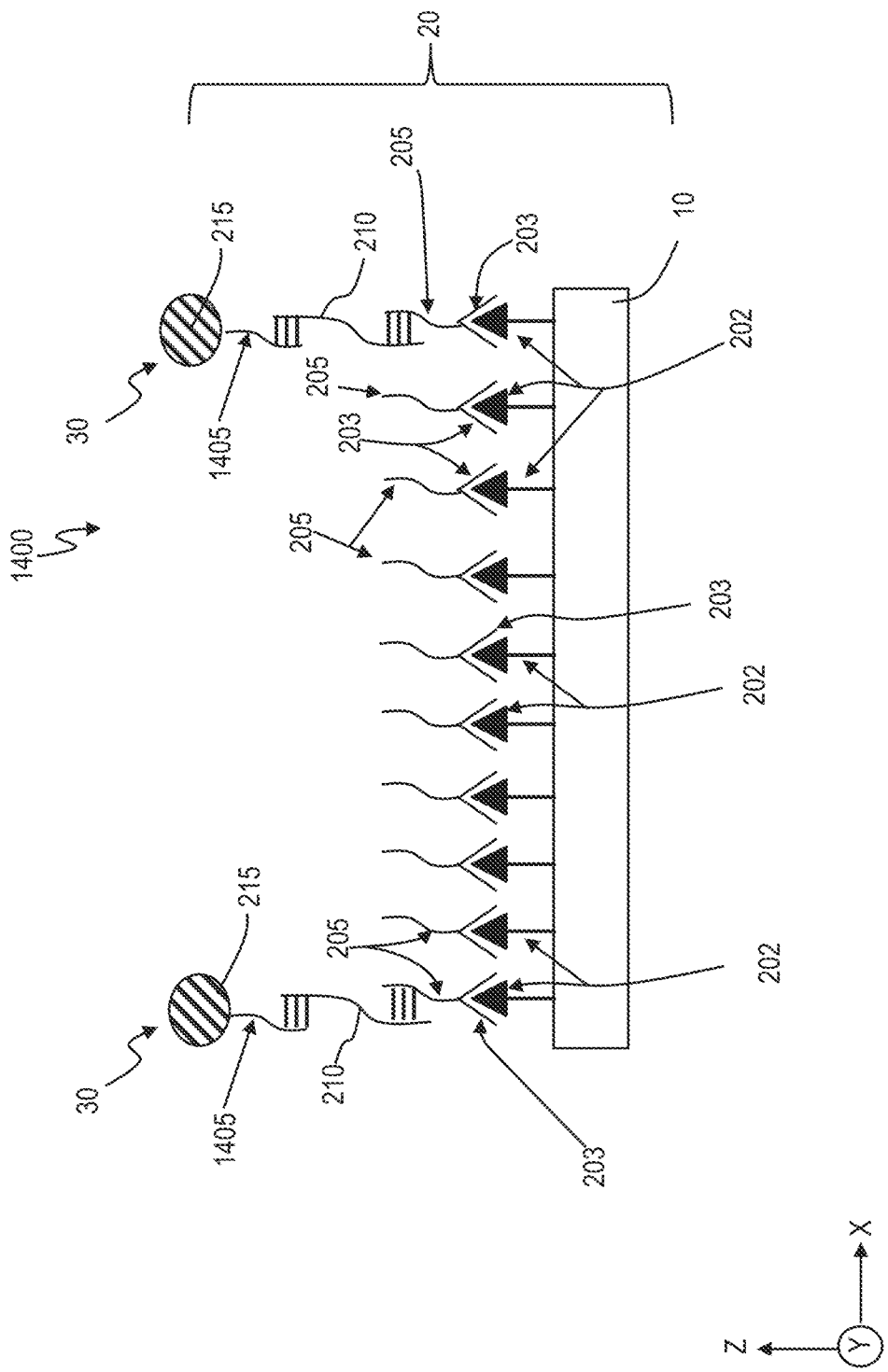
FIG. 14 is a cross-sectional view of a system utilized for detection of a specific DNA sequence within an unknown DNA molecule being tested according to an embodiment.

According to another embodiment, FIG. 14 is a cross-sectional view of a system utilized for detection of a specific DNA sequence within an unknown DNA molecule being tested. FIG. 14 is similar to FIG. 2 except that the second molecule 220 is removed and an additional short probe DNA molecule 1405 is added. In this embodiment, the additional short probe DNA molecule 1405 is attached to the first molecule 215 (i.e., the additional short probe DNA molecules 1405 are attached to the beads 30). Accordingly, one end of the unknown DNA molecule 210 is attached to the additional short probe DNA molecule 1405. In one implementation, the additional short probe DNA molecule 1405 may be the same nucleic acid sequence as the short probe DNA molecule 205.

Optical Detection of Bead Motion with a Cellular Phone

Many smart phones (and tablets) available today in the market like iPhones® (4S, 5, 5C and 6), Samsung® Galaxy, HTC™ and other Android™ phones have a good camera with video recording capabilities. However, their current minimum-focusable distance and the magnification achievable at that distance are not adequate to detect the presence of micron to submicron ($10^{-6}$ to $10^{-5}$ meter) beads 30 in the solution. For iPhone® 5, the minimum-focusable distance is about 5 centimeters (cm) from the front of the camera, and the magnification achieved is about few times which directly impacts the resolution. Therefore, a special lens adapter is needed for current camera phones not having adequate magnification and resolution, and the special lens adapter (e.g., ball lens holder assembly 400 shown in FIGS. 4 and 5) can be attached to these cellphone cameras. It is noted that newer phones or electronic communication devices may be designed with camera technology that has higher magnification and resolution, and some embodiments may not require the special lens adapter.

The special lens adapter has special characteristics like a short focal length and high numerical aperture that can result in magnification in the range of 100-200 times (100-200×) and a spatial resolution of 1 to 2 micrometers. Such characteristics can be achieved by a ball-lens based adapter (e.g., ball lens holder assembly 400 shown in FIGS. 4 and 5), and it can be attached to and/or placed in front of the camera of these cellular phones in a special holder (e.g., micropositioner 418 in FIGS. 4 and 5). In one embodiment, a ball-lens of diameter 3.0 mm made of glass (refractive index 1.52) with very low surface roughness (within microns) placed in a holder and kept over the sample to be imaged was found to have a magnification of approximately 180×, and a resolution of about 1 micron which was adequate to image the beads 30 under suitable low-light illumination conditions (FIGS. 4 and 5).

Figure 4:
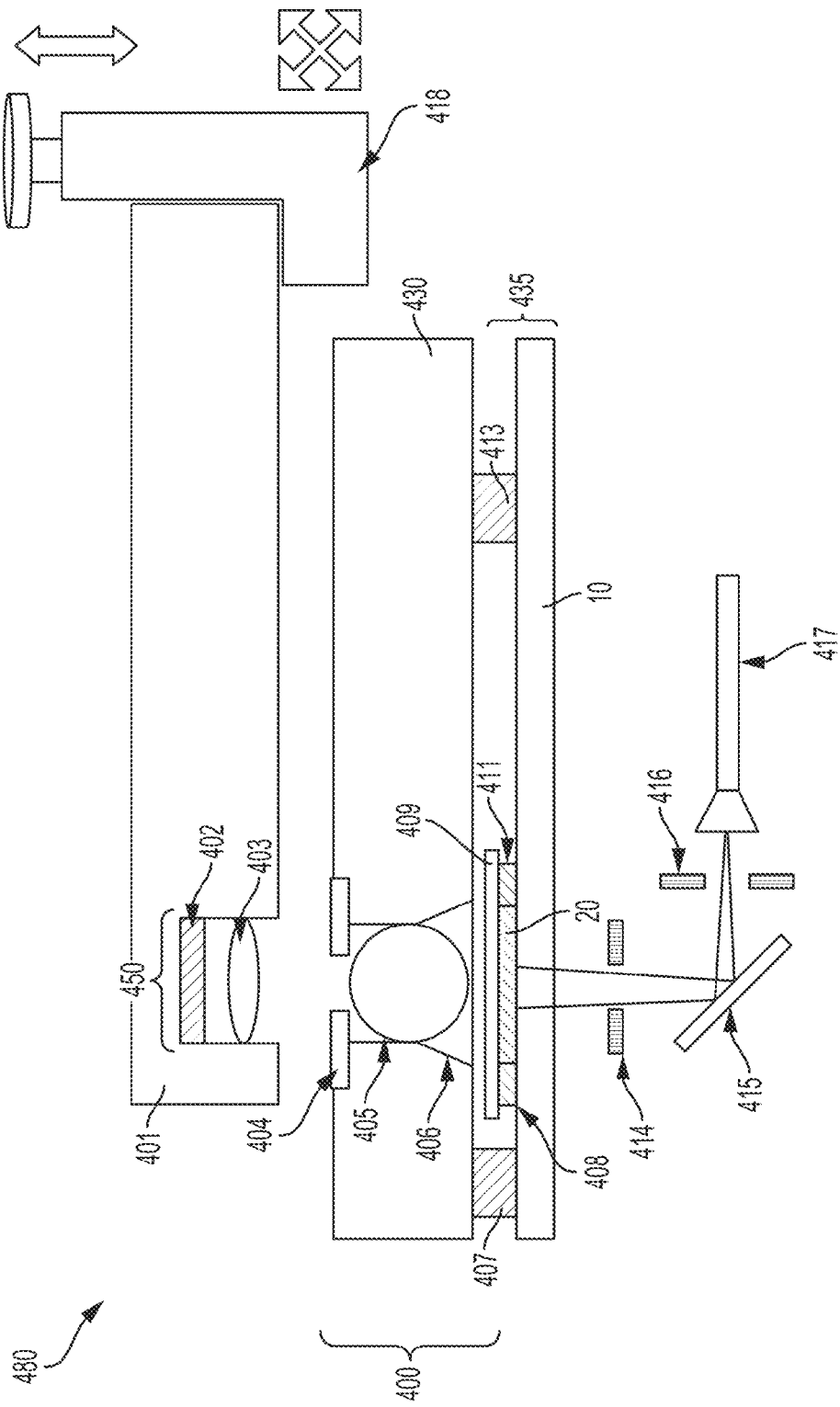
FIG. 4 is a system illustrating a cellular phone based bead motion imaging microscope according to an embodiment.
Figure 5:
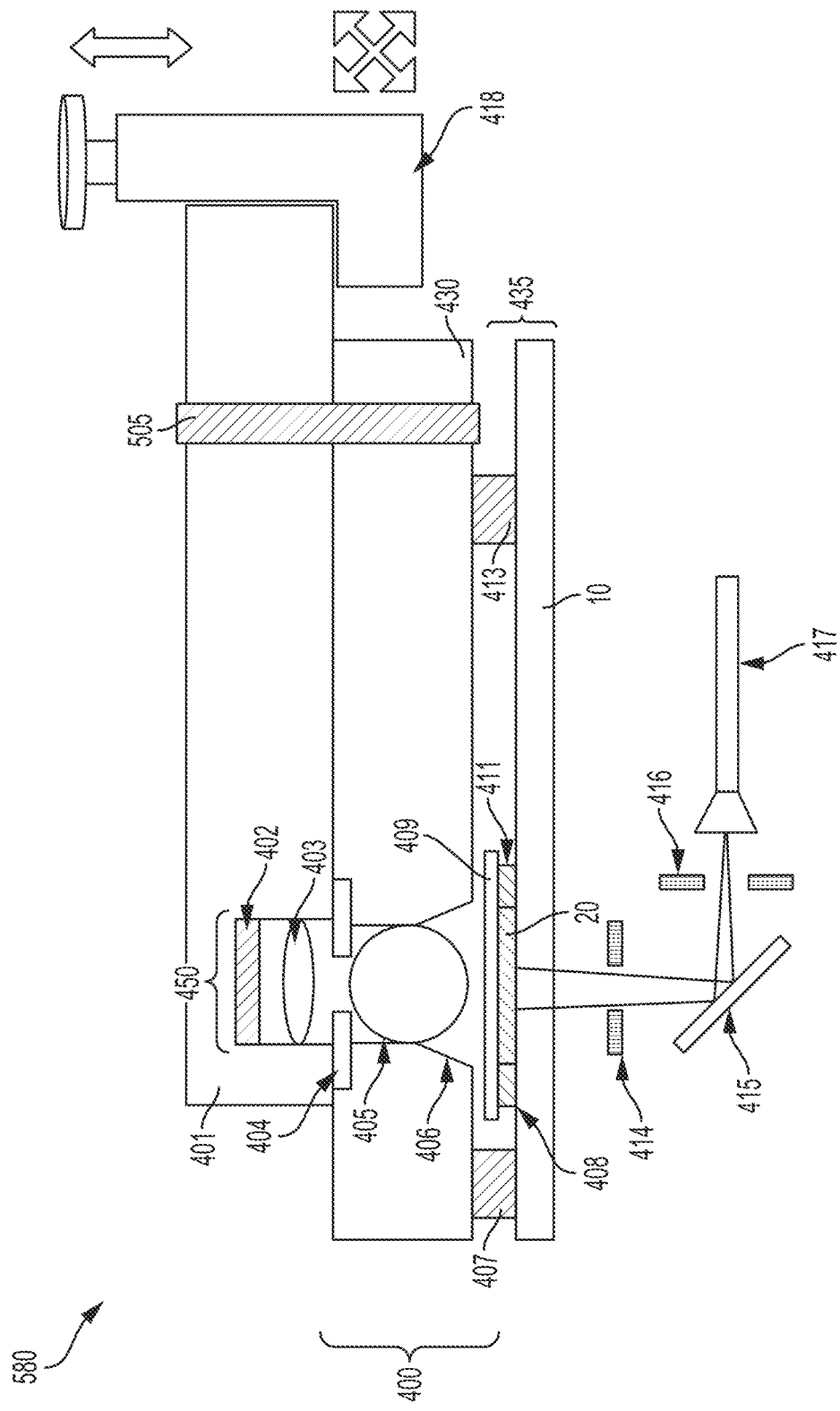
FIG. 5 is a system illustrating a cellular phone based bead motion imaging microscope according to another embodiment.

FIG. 4 is a system 480 depicting a cellular phone based bead motion imaging microscope according to one embodiment. In this experimental configuration, the ball lens holder assembly 400 is placed over the sample chamber in the glass slide 10 covered by a glass cover slip 409 either with the help of spacers 407 and 413 (in one implementation) or without spacers 407 and 413 (in another implementation). The ball lens holder assembly 400 is designed such that the bead sample solution 20 below the cover slip 409 is in the focal plane of a ball lens 405. The cellular phone camera's horizontal position is adjusted to be in the center of the field of view of the spherical ball lens 405 with a micropositioner 418 and the vertical position adjusted to form the image of the beads 30 in the solution 20.

A cellular phone 401 includes a camera 450 with an electronic image sensor 402 (can also be other imaging sensors (including CCDs) with focusing optics). The electronic image sensing surface 402 is positioned behind a camera focusing lens assembly 403. The cellular phone 401 includes a processor, memory (including removable memory), camera computer-executable instructions stored in memory, video recording computer-executable instructions stored in memory, antenna, transceiver, power source (e.g., battery), user interface (touch screen, key pad, voice activation) etc., as understood by one skilled in the art.

The ball lens holder assembly 400 includes a resolution limiting aperture 404. An emission filter (not shown), that blocks the excitation light in the case of imaging fluorescent beads or fluorescent biomolecules like DNA and proteins, can be placed over resolution limiting aperture 404 in one implementation.

The ball lens holder assembly 400 includes the spherical ball lens 405 made from glass, e.g., with a diameter 3.0 millimeters (mm) positioned in a lens holder 430. In another implementation, other smaller or larger diameters such as, e.g., 2.5, 4.0, and 5.0 mm may also be used as the spherical ball lens 405 with the appropriate lens holder assembly. The lens holder 430 may have a tapered opening 406 to accept a light cone of large angle from the sample plane formed by the solution 20 of beads 30. Spacers 407 and 413 keep the required separation between the ball lens holder assembly 400 and the glass slide 10 that contains the bead solution 20. Double-sided tape or adhesive may act as spacers 408 and 411 for the sealed sample chamber 435. In another implementation, a sample cell may also consist of a glass or transparent polymer-based microfluidic cells. A glass cover slip 409 acts as the lid for the sample chamber 435. The sealed sample chamber 435 comprises the glass slide 10 and glass cover slip 409. The bead solution 20 (containing the beads 30) that is being imaged (via camera 450 of the cellular phone 401) is placed on the glass slide 10. The glass slide 10 forms the bottom surface of sample chamber 435 enabling different kinds of functionalization such as with antibody and protein coatings to bind to either the DNA molecule 210 or other small molecules 220 like biotin.

The ball lens holder assembly 400 works with light limiting apertures 414 and 416. An excitation filter (not shown) can be placed over the aperture 414 for imaging fluorescent beads and fluorescent DNA and RNA biomolecules. A mirror 415 is utilized for reflecting light towards the sample chamber 435 and the ball lens holder assembly 400.

A battery-operated LED flash lamp, with white light or colored light, may be utilized as a light source 417. As another option, the light source 417 may be a single LED suitably wired for electrical power. The light source 417 may be a small laser diode suitably powered. In the case of a single LED or laser diode, the light source 417 can be placed directly under the aperture 414 without the need for the mirror 415 and the light limiting aperture 416. The light source 417 may also be formed with a flat LED chip mounted on a suitable holder, wired for electrical power, and placed under the aperture 414. A micropositioner 418 holds the cellular phone 401 and can move in three orthogonal x, y, and z directions. The micropositioner 418 is used for positioning the cellular phone camera 450 directly over the lens holder assembly 400 centered at the resolution limiting aperture 414 and for adjusting the vertical distance from this aperture 414 to get a good focus of the beads in the solution.

FIG. 5 is a system 580 depicting a cellular phone based bead motion imaging microscope according to another embodiment. The system 580 in FIG. 5 includes the features of the system 480 in FIG. 4. However, in this experimental configuration, the ball lens holder assembly 400 is attached to the cellular phone 401 with the field of view of the spherical ball lens 405 approximately centered with the field of view of the cellular phone camera 450. The alignment can be done by adjusting the lens holder assembly 400 to image a bright uniformly lit object or a light source such as an LED flash lamp in order to ensure that the image has uniform intensity. The horizontal and vertical positions of the cellular phone 401 with the lens assembly 400 are adjusted with the micropositioner 418 to bring the beads 30 in the solution 20 into focus. Once aligned, the cellular phone 401 may be attached to the ball holder assembly 400 with an attaching piece 505, and the attaching piece 505 may be clamps, adhesive material, etc. In addition, the use of the image resolution limiting aperture 404 is optional in FIG. 5, and thus may not be utilized in one implementation.

In the experimental setups described in FIGS. 4 and 5, a single ball lens 405 has been used to image the Brownian motion of the beads 30 in solution 20. Depending on the planarity of the glass slide sample chamber 435 and the slight unintended off-centering of the ball lens field-of-view with respect to the cellular phone camera field-of-view, some distortion of the bead images near the edge of the field of view might occur. This distortion can be reduced substantially or removed if two half-ball lenses are used. This configuration also allows for a slightly wider field-of-view than achievable with a single ball lens, as illustrated in FIG. 6.

Figure 6:
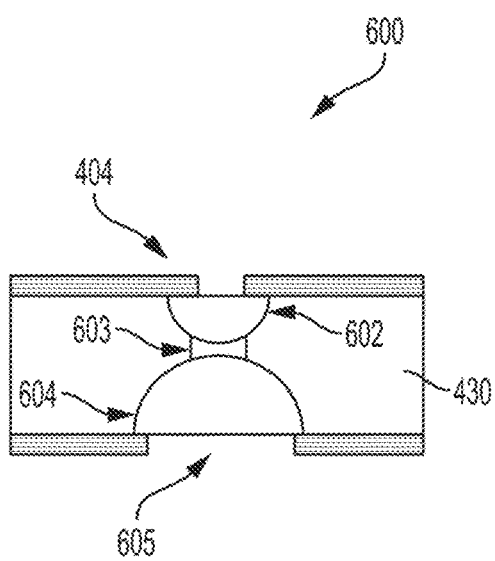
FIG. 6 illustrates a Wollaston-like doublet arrangement with two half-ball lenses according to an embodiment.

FIG. 6 illustrates a Wollaston-like doublet arrangement 600 that may be utilized according to an embodiment. The two half-ball lenses 601 and 603 are arranged in such a way that their curved surfaces face each other. Aperture 404 is the resolution limiting aperture. Half-ball lens 602 is the smaller half-ball lens that can be of diameter 1.5 to 2.5 mm. The connecting light path hole 603 acts as another resolution limiting aperture. Half-ball lens 604 is the bigger half-ball lens which can have diameter larger than the smaller half-ball lens by 1.0 to 2.5 mm. Wollaston-like doublet arrangement 600 has a field aperture 605. While the aperture 605 should be larger to accept a large cone of light scattered from the sample material, the apertures 603 and 404 can be optimized to achieve a spatial resolution of 1 to 2 microns. The vertical separation between the two lenses can be optimized to achieve a total magnification of 150 to 200 times for observing the motion of 1 micron sized beads. Wollaston-like doublet arrangement 600 can be utilized in place of the elements 405 and 406 in the ball lens holder assembly 400.

EXAMPLE EXPERIMENTAL DATA 1

Before detecting Brownian motion of the beads 30, experiments were carried out imaging beads that are stuck to a glass surface or frozen in a gel matrix coated on a glass slide in order to compare with the recordings of moving beads 30. Images recorded with 1.2 micron sized beads 30 are shown in a raw image 750 and processed image 755 in FIGS. 7A and 7B, respectively.

Figure 7A:
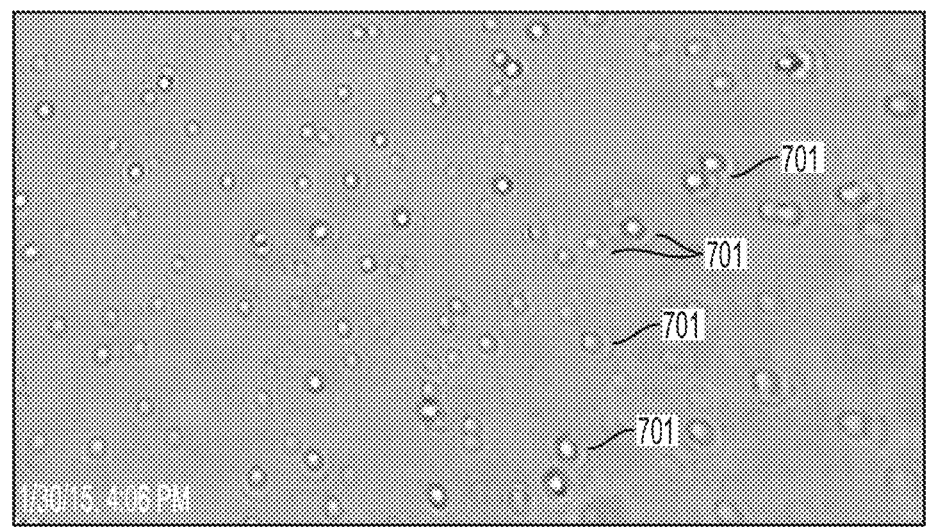
FIG. 7A is an image illustrating polystyrene beads of micron size stuck on a glass slide according to an embodiment.

FIG. 7A illustrates image 750 showing polystyrene beads of average size 1.2 microns stuck on a glass slide. The beads were obtained from Bangs Laboratories, Inc™, Fishers, Ind. Using the setup described in FIG. 5, the original image 750 of the beads stuck on the glass slide is recorded with transmitted light from an LED flash white light illumination. The individual beads can be seen as bright spots surrounded by darker circles 701.

Figure 7B:
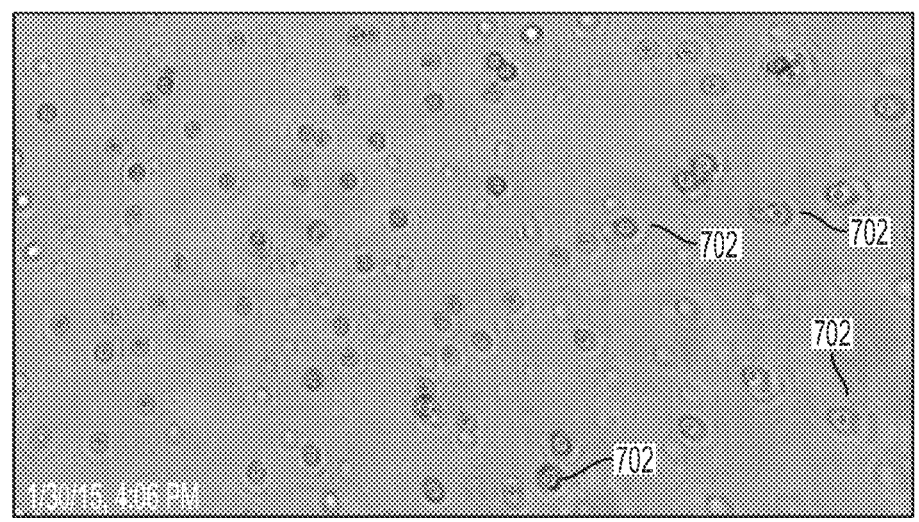
FIG. 7B is an image pre-processed after converting to a gray-scale image and band pass filtering for optimal feature enhancement according to an embodiment.

FIG. 7B illustrates image 755 pre-processed after converting to a gray-scale image and band pass filtering for optimal feature enhancement. The circles 702 are centered around bead positions in frame-1 while the crosses are from bead positions in frame-2, where frame-1 and frame-2 are consecutive in a video clip. The bead positions detected after pre-processing the original image 750 by band-pass filtering with intensity threshold setting are shown as the circles 702. In FIG. 7B, a large number of detected bead positions can be seen.

Figure 7C:
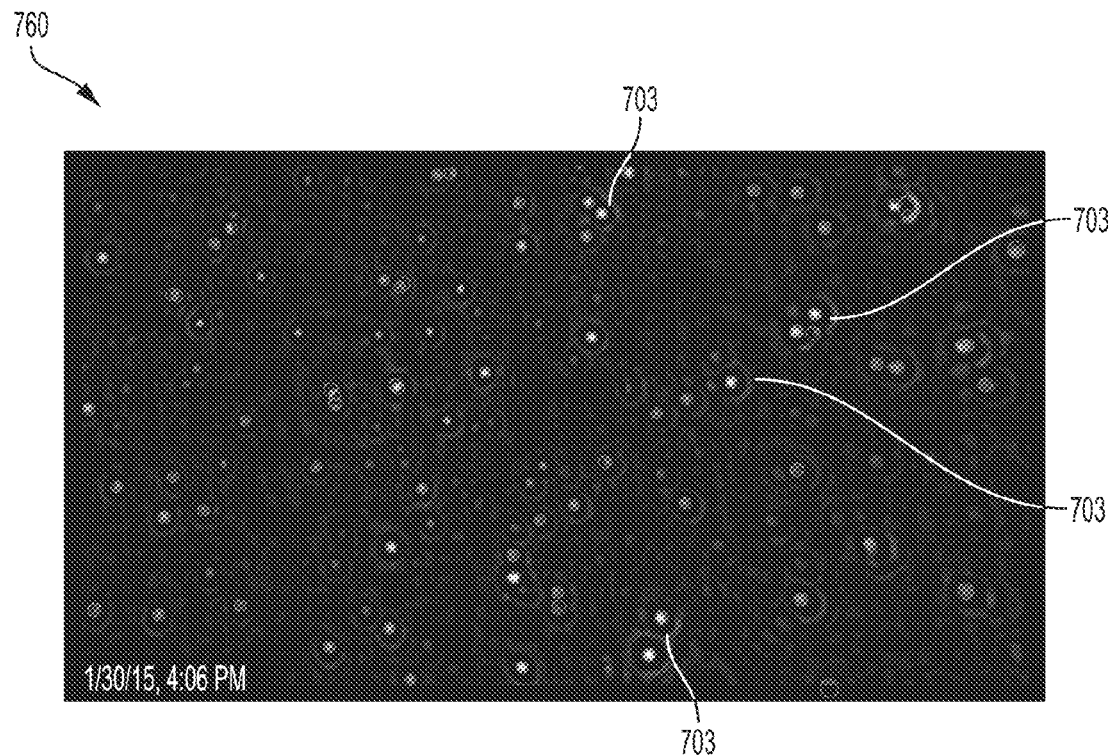
FIG. 7C is an image of bead positions detected with a MATLAB® function according to an embodiment.

For comparison, the bead positions detected with a MATLAB® function called imfindcircles function is shown in FIG. 7C, and the MATLAB® function has a large number of beads detected (circles 703). FIG. 7C illustrates image 760 showing bright spots identified by imfindcircles function in MATLAB® after some pre-processing. The particular circle 703 is drawn to the size of the radius found by the imfindcircles function for each corresponding bead 30 location in the image.

Figure 7D:
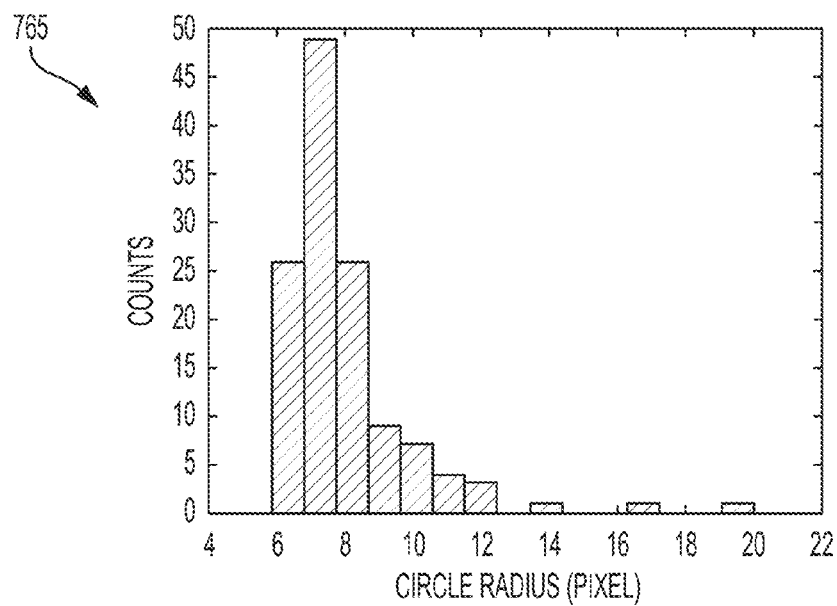
FIG. 7D is a histogram graph illustrating the distribution of the detected circle radius in pixels from the image in FIG. 7C according to an embodiment.

FIG. 7D illustrates a histogram graph 765 showing the distribution of the radius of the detected circles 703 in pixels from the image 760 in FIG. 7C. For the image 760, bead positions corresponding to circles 703 were identified (using MATLAB®) in the first frame of a video clip and their corresponding positions were identified in the second frame giving allowance for a maximum displacement of 10 pixels between these two frames. However, the analysis shows that the dominant amount of displacement of beads between these two frames is less than 0.05 pixels, and it further shows that the larger displacements that are still below 1 pixel are negligible as shown in FIGS. 7E-1 and 7E-2 and FIGS. 7F-1 and 7F-2.

It is noted that the displacement of a bead is the length/distance that a bead moves in a particular direction, along the x-axis or y-axis. Since the microscope images the motion in a plane which is two dimensional, in general, the bead displacement will be in an arbitrary direction in the plane. For simplification of the analysis, only x- or y-component of the bead motion was analyzed which corresponds to diffusion in one dimension. However, from the x- and y-positions of the beads obtained in the analysis their total displacement, $$\delta \vec{r} = \vec{r}_2 - \vec{r}_1 = (x_2 - x_1) + (y_2 - y_1) = \delta x \cdot \hat{x} + \delta y \cdot \hat{y}$$

Where $\vec{r}_2$ and $\vec{r}_1$ denote the 2D position vector of the bead displacements, $\hat{x}$, $\hat{y}$ represent the unit vectors along x- and y-directions respectively. Therefore, square of radial displacement can be calculated as:

$$\delta \vec{r}^2 = \delta x^2 + \delta y^2$$

and the mean-squared displacement $\delta r^2$ can be calculated from the successive x- and y-positions of the beads and it obeys the following equation:

$$\delta r^2 = 4Dt$$

Figures 1, 7E:
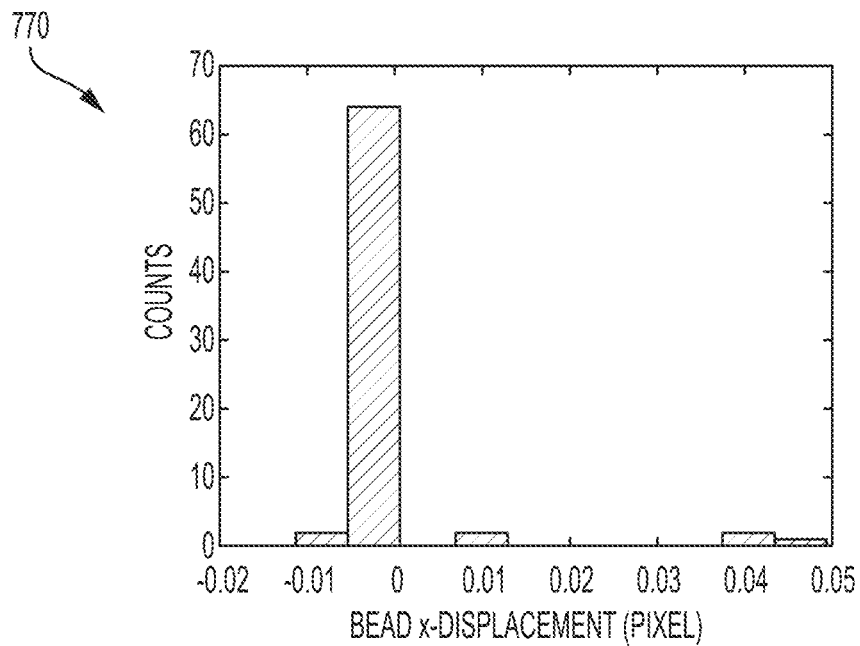
Figures 2, 7E:
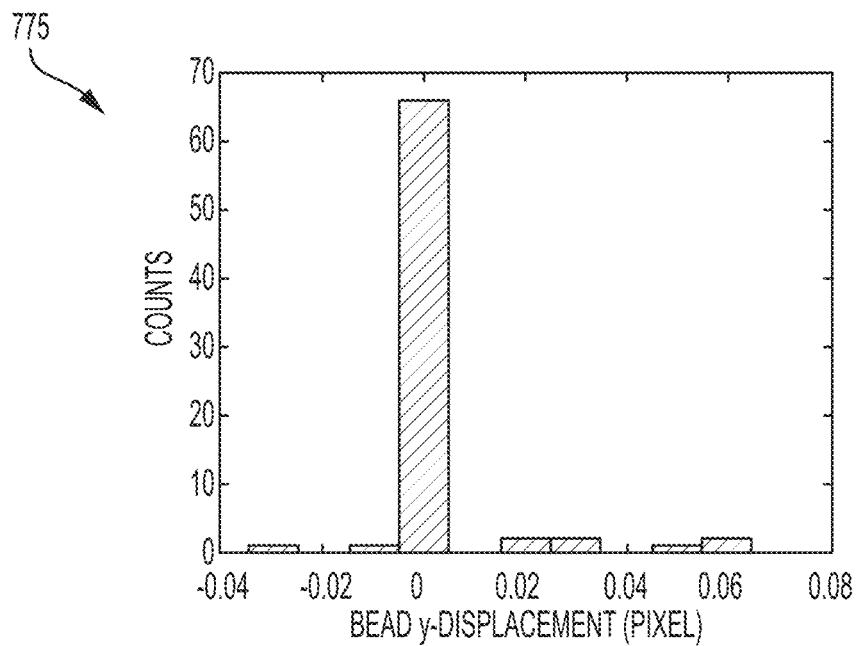

FIGS. 7E-1 and 7E-2 illustrate the displacement in bead positions between two consecutive images. FIGS. 7E-1 and 7E-2 are histogram graphs 770 and 775, respectively, of the distribution in bead positions between two consecutive video frames (which included the image 760). The histogram graph 770 shows that the smaller displacement is less than 0.05 pixels for the x-position, and most of the displacements are within −0.005 in FIG. 7E-1.

FIG. 7E-2 shows a similar behavior for y-positions in the histogram graph 775. This analysis shows both the robustness of the experimental setup in FIG. 5 (as well as FIG. 4) keeping the residual mechanical vibrations from the floor low enough for observing the static images of the beads and the effectiveness of the algorithm in finding the bead positions from the image frames of the video clip frames.

Figures 1, 7F:
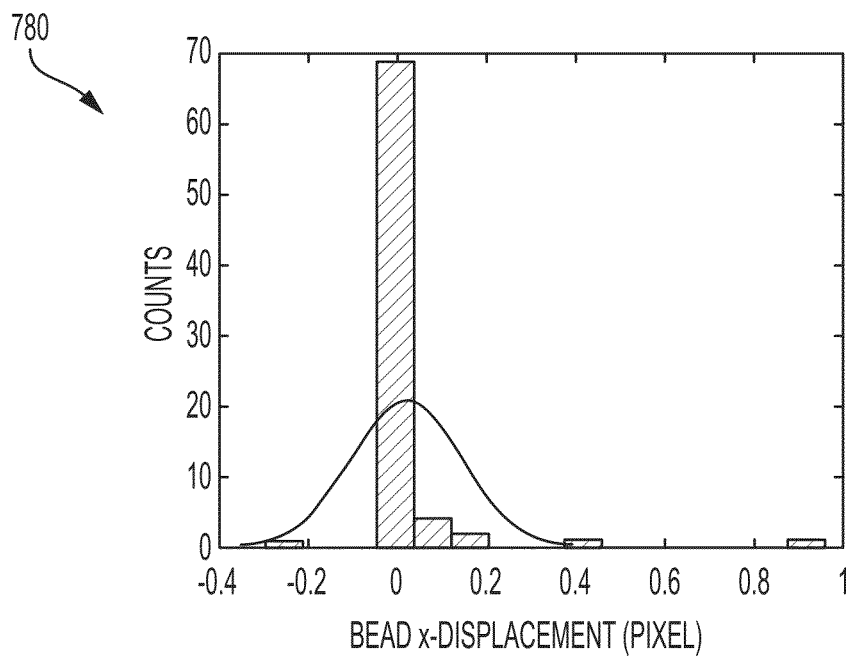
Figures 2, 7F:
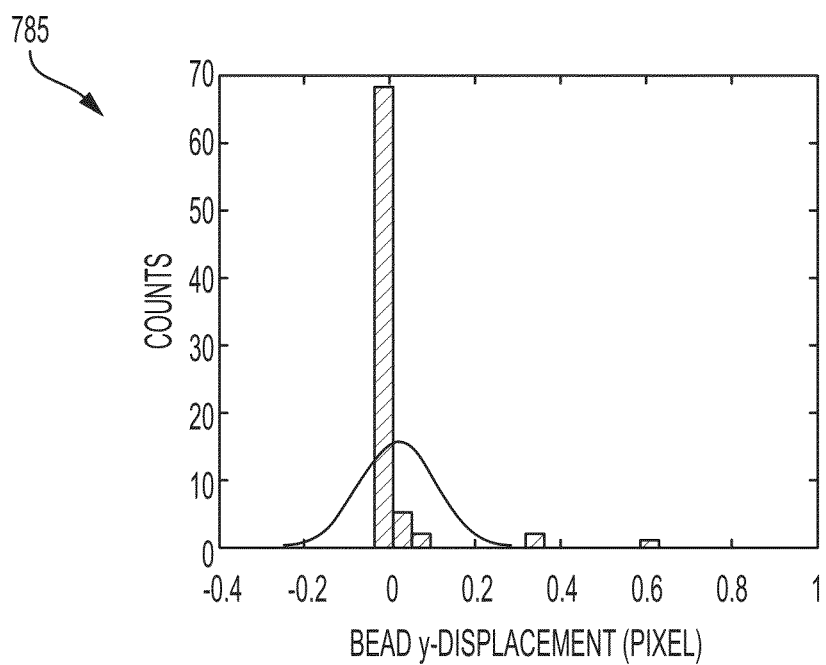

FIGS. 7F-1 and 7F-2 respectively illustrate the x and y displacements (both small and large). FIG. 7F-1 shows a histogram graph 780 of the distribution of total displacement in bead positions between two consecutive video frames. The histogram graph 780 shows that the displacement less than 0.05 pixels for x-positions dominates the total displacement. Similarly, histogram graph 785 shows that the displacement less than 0.05 pixels for y-positions dominates the total displacement.

Figures 1, 7G:
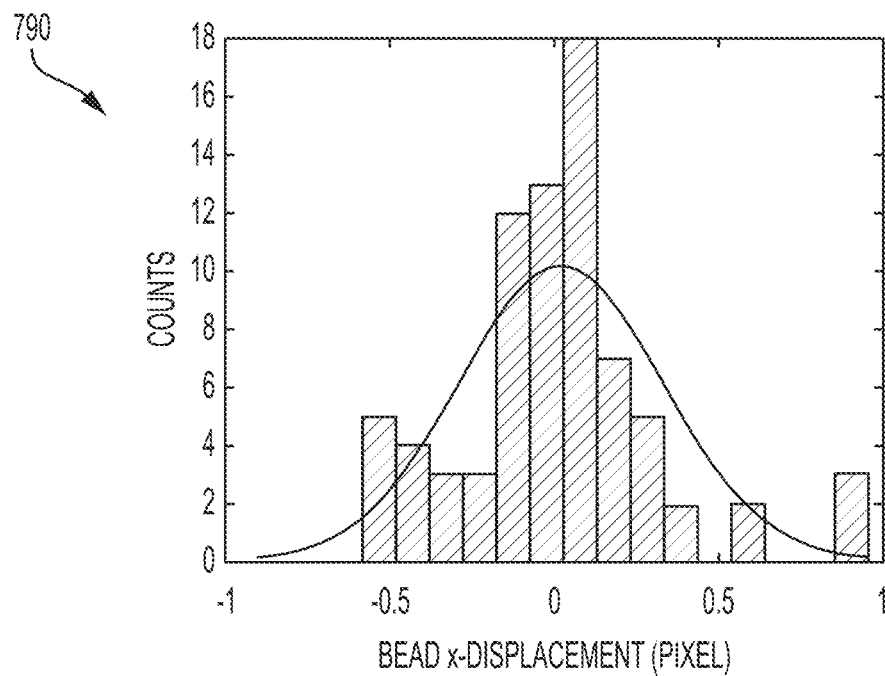
Figures 2, 7G:
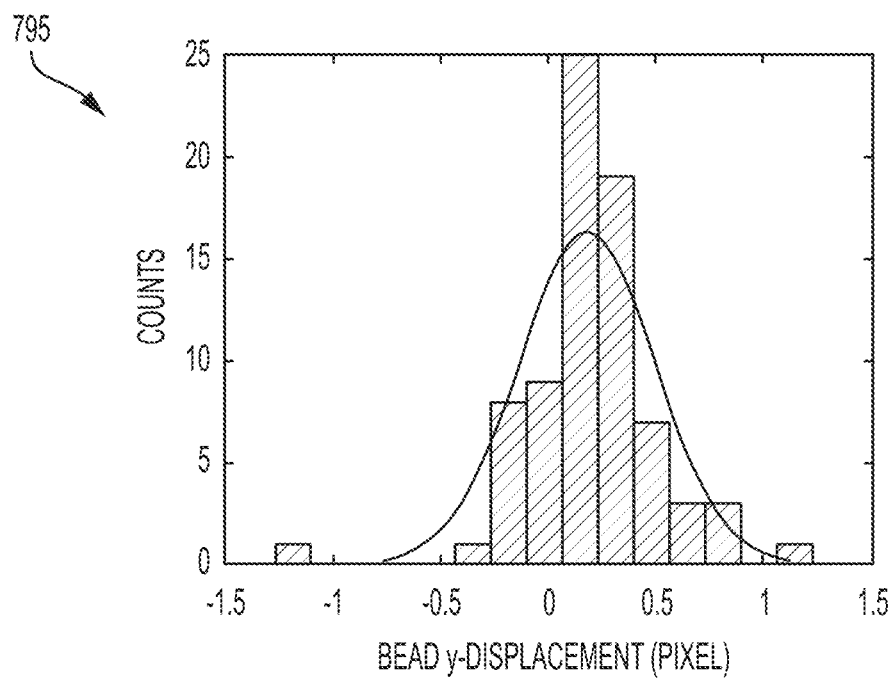

On the other hand, the bead displacements between first and third frames spanning 0.5 pixels are still smaller than a single pixel as shown in FIGS. 7G-1 and 7G-2. FIG. 7G-1 shows histogram graph 790 of x-displacement while FIG. 7G-2 shows histogram graph 795 of y-displacement. Note that most of the x and y displacements of the beads in frame-1 and frame-3 are within 0.5 pixel which is good and testifies of the high accuracy of these algorithms in finding the bead center positions with sub-pixel accuracy. This shows the adequacy of both the experimental setup in FIG. 5 (along with FIG. 4) and the algorithms for recording and locating the bead positions with sub-pixel accuracy.

An example algorithm for detecting and tracking the movement (i.e., bead positions) of the individual beads 30 is provided below according to an embodiment. For a video clip/recording of the motion of the beads 30 (e.g., captured with the cellular phone 401), the example algorithm may be utilized to detect and track beads from one video frame to the next (consecutive video frame). The algorithm may be executed by and stored in memory of the cellular phone 401 and/or the cellular phone 401 may send the recorded video clip/recording to a computer system (such as the computer system 1200) for analysis; the computer system has memory to store the algorithm. The example algorithm is configured to identify each circular bead and store each bead's pixel location in a video frame, such that the algorithm identifies and stores each bead's pixel location throughout consecutive video frames. For example, the algorithm is configured to track and identify each bead's pixel location over video frames (e.g., over consecutive video frames). The algorithm is configured to measure the x-displacement and y-displacement of each bead 30 from one video frame to the next video frame, such that the algorithm stores the change in pixel location for each bead. The algorithm determines an x-displacement and y-displacement for each bead 30 in the x-axis and y-axis, over a predefined number of video frames (i.e., a particular time, such as, e.g., 1, 3, 5, 10, 15, 20, 25 . . . 60 seconds). For the particular sample having the unknown DNA molecule 210 being tested, the algorithm determines the total x-displacement for all of the individual beads 30 and the total y-displacement for all of the individual beads 30. The algorithm is configured to compare the total x-displacement and y-displacement for the beads 30 being tested with the unknown DNA molecule 210 attached (i.e., corresponding to the Brownian motion of the tested DNA molecule 210 ) to the previously stored total x-displacement and y-displacement for the same size beads without the unknown DNA molecules 210 attached (i.e., corresponding to free Brownian motion). When the total x-displacement and y-displacement for the beads 30 being tested with the unknown DNA molecule 210 attached (i.e., corresponding to the Brownian motion of the tested DNA molecule 210 ) is less than (by a predetermined amount) the previously stored total x-displacement and y-displacement for the same size beads without the unknown DNA molecules 210 attached (i.e., corresponding to free Brownian motion), the algorithm determines that the Brownian motion is restricted (i.e., the beads 30 are tethered to the sample surface 10 via the DNA molecule 210 ) and the unknown DNA molecule 210 contains the known specific nucleic acid sequence being tested for.

However, when the total x-displacement and y-displacement for the beads 30 being tested with the unknown DNA molecule 210 attached (i.e., corresponding to the Brownian motion of the tested DNA molecule 210 ) is about equal to (within a predetermined margin) the previously stored total x-displacement and y-displacement for the same size beads without the unknown DNA molecules 210 attached (i.e., corresponding to free Brownian motion), the algorithm determines that the Brownian motion is not restricted (i.e., the beads 30 are not tethered to the sample surface 10 via the DNA molecule 210 ) and the unknown DNA molecule 210 does not contain the known specific nucleic acid sequence being tested for.

EXAMPLE EXPERIMENTAL DATA 2

Referring to FIGS. 8A-1 and 8A-2, a similar analysis was carried out with micron sized beads affixed in a gel matrix coated on a glass slide (from PolySciences Inc., of Warrington, Pa.). FIGS. 8A-1 and 8A-2 respectively show the fluorescent image 805 recorded from these polymer beads and the processed image 810 with the bead positions identified in two consecutive frames. The images are extracted from the video clip recorded from 6 micron size calibration standard beads (from PolySciences, Inc., Warrington, Pa.).

Figure 8B:
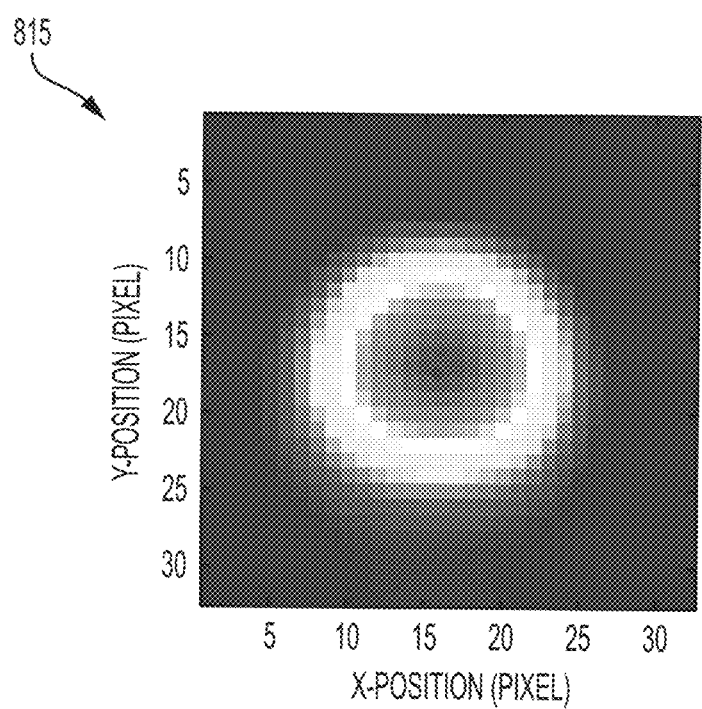
FIG. 8B is a graph illustrating pixel-level intensity distribution of a detected bead image according to an embodiment.

In FIG. 8A-1, the original fluorescent image 805 was recorded with transmitted light from LED flash light illumination using the setup described in FIG. 5 (although the setup in FIG. 4 could be used) but with an excitation filter placed over the aperture after the mirror. The circle 801 shows individual beads in the original fluorescent image 805. In FIG. 8A-2, circles 802 are centered around bead positions in frame-1 and the crosses are centered at bead positions in frame-2 extracted from a video clip. The algorithm first identifies the bead position at a coarse level which is used to find the bead position to sub-pixel accuracy by analyzing intensity distribution around this position over a 10×10 to 20×20 window. The window is user controllable. Intensity distribution around one such peak is seen in FIG. 8B.

FIG. 8B is an graph 815 of pixel-level intensity distribution of a detected bead image showing the extent of the bright region spanning about 10×10 pixels. The displacement of pixels in graph 815 is much larger than the largest displacement 0.05 pixels obtained from the analysis of the images in FIGS. 8D-1, 8D-2, 8E-1, and 8E-2.

Figures 1, 8C:
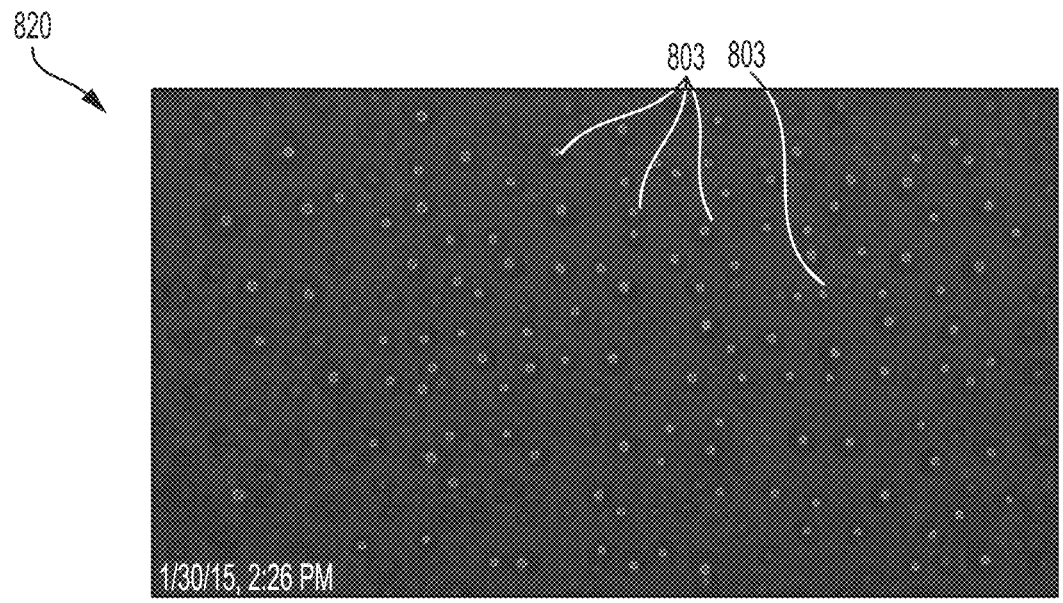
Figures 2, 8C:
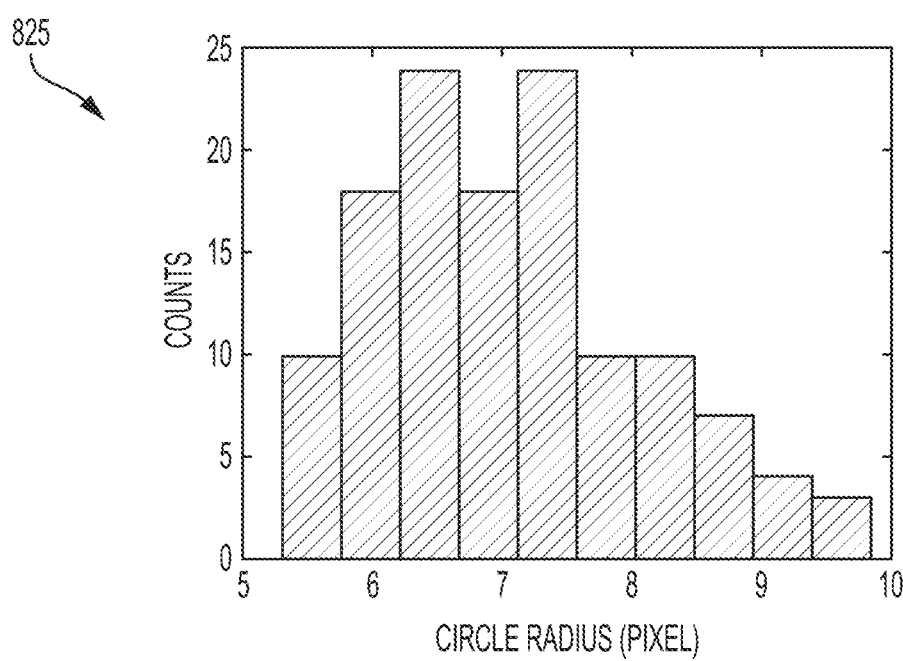

FIG. 8C-1 illustrates an image 820 showing bright spots identified by the imfindcircles function in MATLAB®, and a large number of bead positions are identified. Each circle 803 is drawn to the size of the radius found by imfindcircles function for each bead position. FIG. 8C-2 is a graph 825 illustrating the distribution of found circle radii in pixels.

Analysis of the displacement of beads in two consecutive frames shows that the displacement less than 0.01 pixels dominates the distribution in FIGS. 8D-1, 8D-2, 8E-1, and 8E-2. This is further consolidation of the adequacy of the experimental setup and the algorithms for locating the bead positions with sub-pixel accuracy.

Figures 1, 8D:
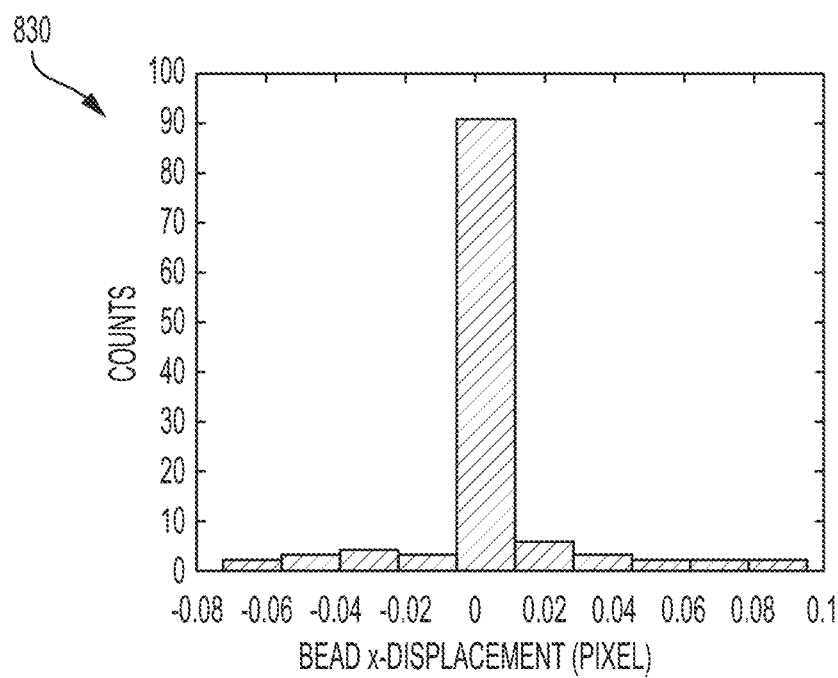
Figures 2, 8D:
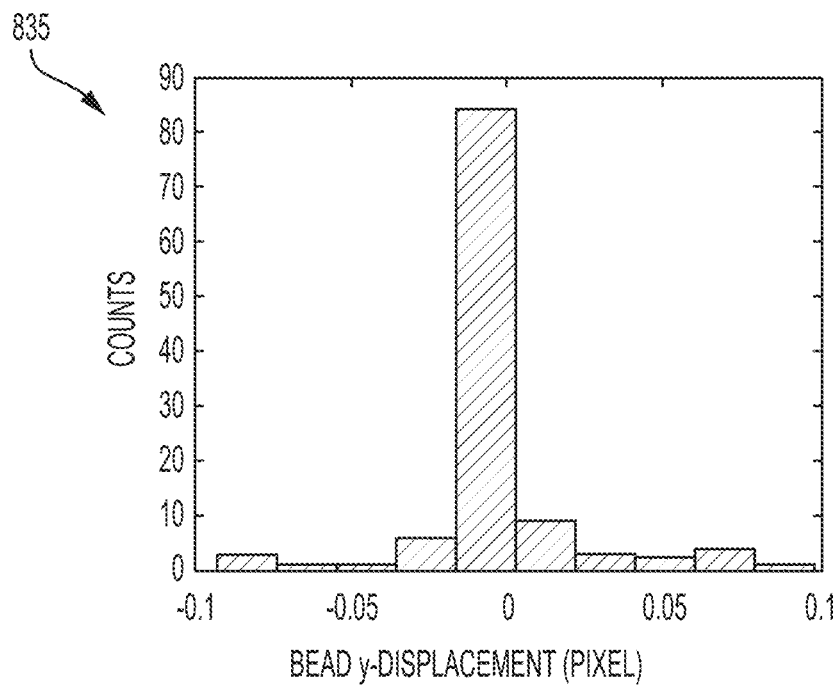

FIGS. 8D-1 and 8D-2 illustrate displacement in bead positions between two consecutive images of a video clip. FIG. 8D-1 is a histogram graph 830 of the distribution of total displacement in bead positions between two consecutive video frames, and shows that a displacement less than 0.01 pixels for x-positions dominates the total displacement. FIG. 8D-2 is a histogram graph 835 of the distribution of total displacement in bead positions between the two consecutive video frames, and also shows that a displacement less than 0.01 pixels for y-positions dominates the total displacement. Note that the analysis of 1.2 micron beads stuck on glass slide also showed similar behavior in FIGS. 7F-1 and 7F-2, which consolidates the effectiveness of the algorithm for finding the position of small as well as large beads.

Figures 1, 8E:
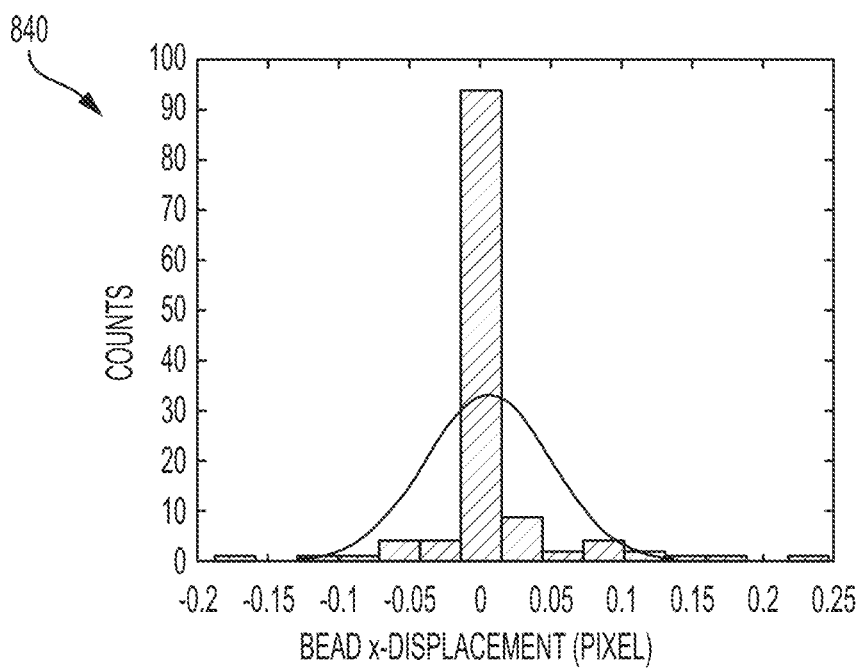
Figures 2, 8E:
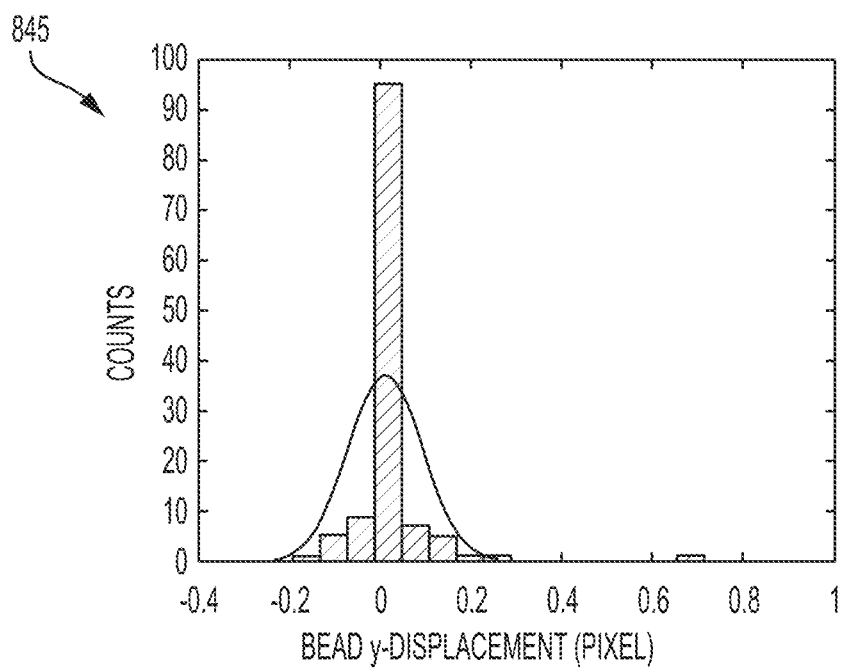

FIGS. 8E-1 and 8E-2 illustrate x and y displacements (both small and large). FIG. 8E-1 is a histogram graph 840 of the distribution of total x-displacement in bead positions between two consecutive video frames showing larger displacements as well. However, the smaller displacements are peaked at close to zero for x-displacement.

FIG. 8E-2 is a histogram graph 845 of the distribution of total y-displacement in bead positions between two consecutive video frames. The y-displacement in graph 845 has similar behavior the x-displacement in graph 840.

EXAMPLE EXPERIMENTAL DATA 3

Figure 9A:
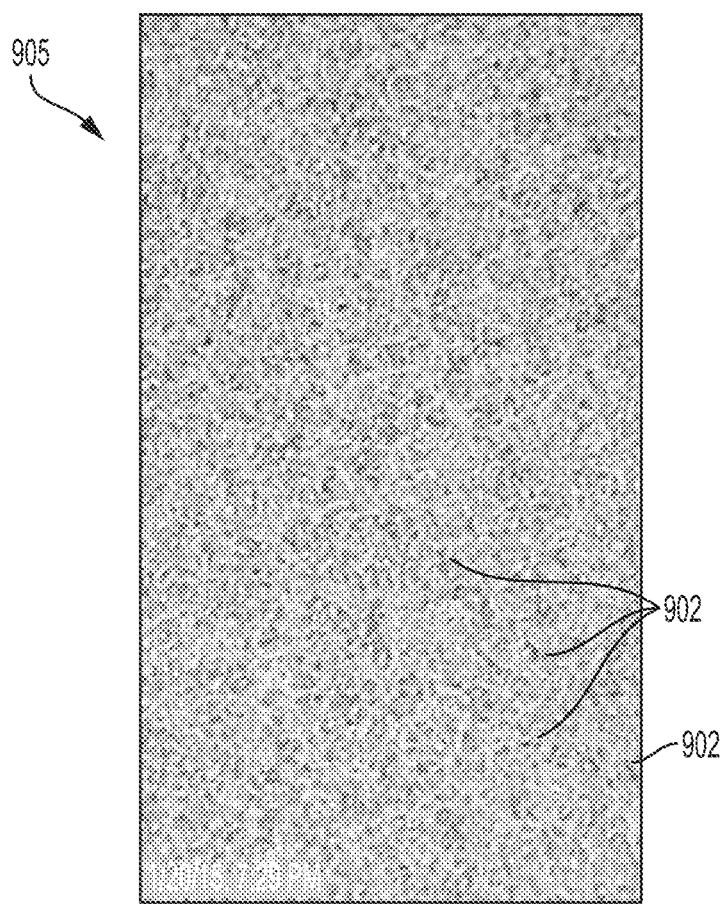
FIG. 9A is an image of a frame illustrating the bead motion according to an embodiment.

Now, turning to another experiment, dilute solutions of polystyrene beads of 1.2 micron size were used to record the motion of the beads. An image 905 of a frame from the video clip recording the bead motion is shown in FIG. 9A. The individual beads appear as dark spots 902. The image 905 extracted from the video clip is recorded of 1.2 micron size polystyrene beads from Bangs Laboratories, Inc™. Original image 905 was recorded with transmitted light from white LED flash light illumination using the setup described in FIG. 5.

The band-pass filtered image and the identified bead positions in a single frame are shown in FIGS. 9B-1 and 9B-2. The beads appear as bright spots 903 after preprocessing with band-pass filtering in the band-pass filtered gray-scale image 903 of FIG. 9B-1. FIG. 9B-2 illustrates a zoomed in image 915 of the detected bead positions shown as circles 904. The displacement of the positions of the beads between two consecutive frames was obtained by similar analysis utilized above in FIGS. 7 and 8. However, in this case where the beads are free to move in the solution, beads are displaced (i.e., travel) by as large as 15 pixels in FIGS. 9C-1, 9C-2, and 9C-3. Moreover, the distribution of their displacement can be fit nicely to Gaussian distributions in FIGS. 9C-1, 9C-2, and 9C-3 for both x and y positions. This (i.e., the distribution of the x and y displacements for beads free to move in the solution) is in sharp contrast with the results obtained for static beads described earlier in FIGS. 7 and 8. This behavior (the distribution of the x and y displacements for beads free to move in the solution) in FIGS. 9C-1, 9C-2, and 9C-3 is expected from the Brownian motion of the beads. These results in FIGS. 9C-1, 9C-2, and 9C-3 show that the experimental setup with the ball lens has sufficiently large numerical aperture and high resolution to resolve individual beads of size 1.2 microns.

FIG. 9C-1 is a graph 920 illustrating that the bead x-position shifted between two frames fits nicely to a Gaussian distribution expected for the random displacement of the beads with the maximum allowed displacement of 5 pixels. FIG. 9C-2 is a graph 925 of the distribution when the maximum allowed x-shift in pixel position is 15 pixels. FIG. 9C-2 also fits nicely to a Gaussian demonstrating that the beads undergo random displacements expected from their Brownian motion, which can be imaged with the cellular-phone microscope setup described in FIG. 4. FIG. 9C-1 is a graph 930 illustrating that similar behavior occurs for the y-position shifts in the bead positions.

Figure 10A:
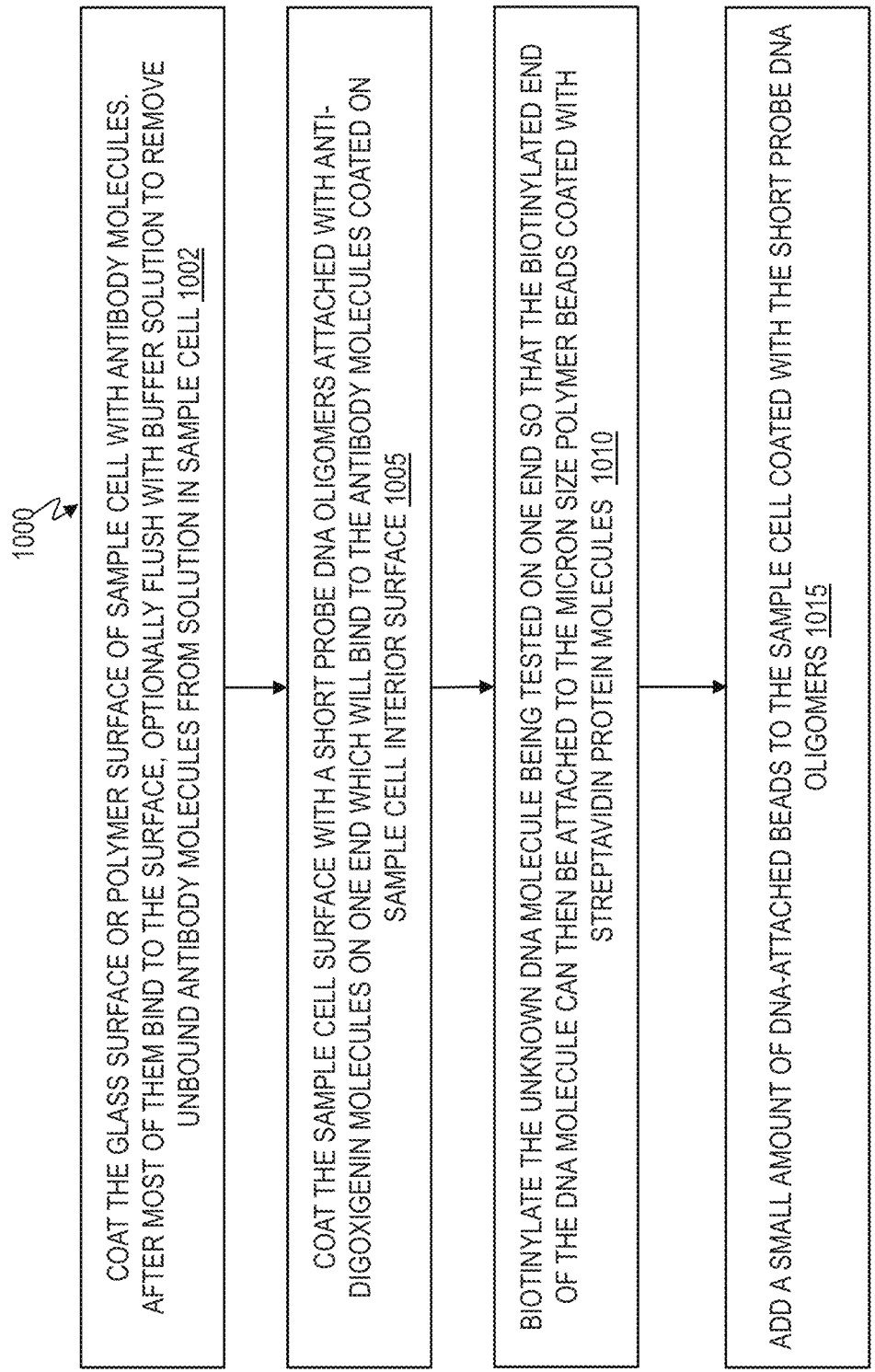
FIGS. 10A and 10B together illustrate a process of optical detection to determine the absence and/or presence of a nucleic acid sequence in a sample being tested according to an embodiment.
Figure 10B:
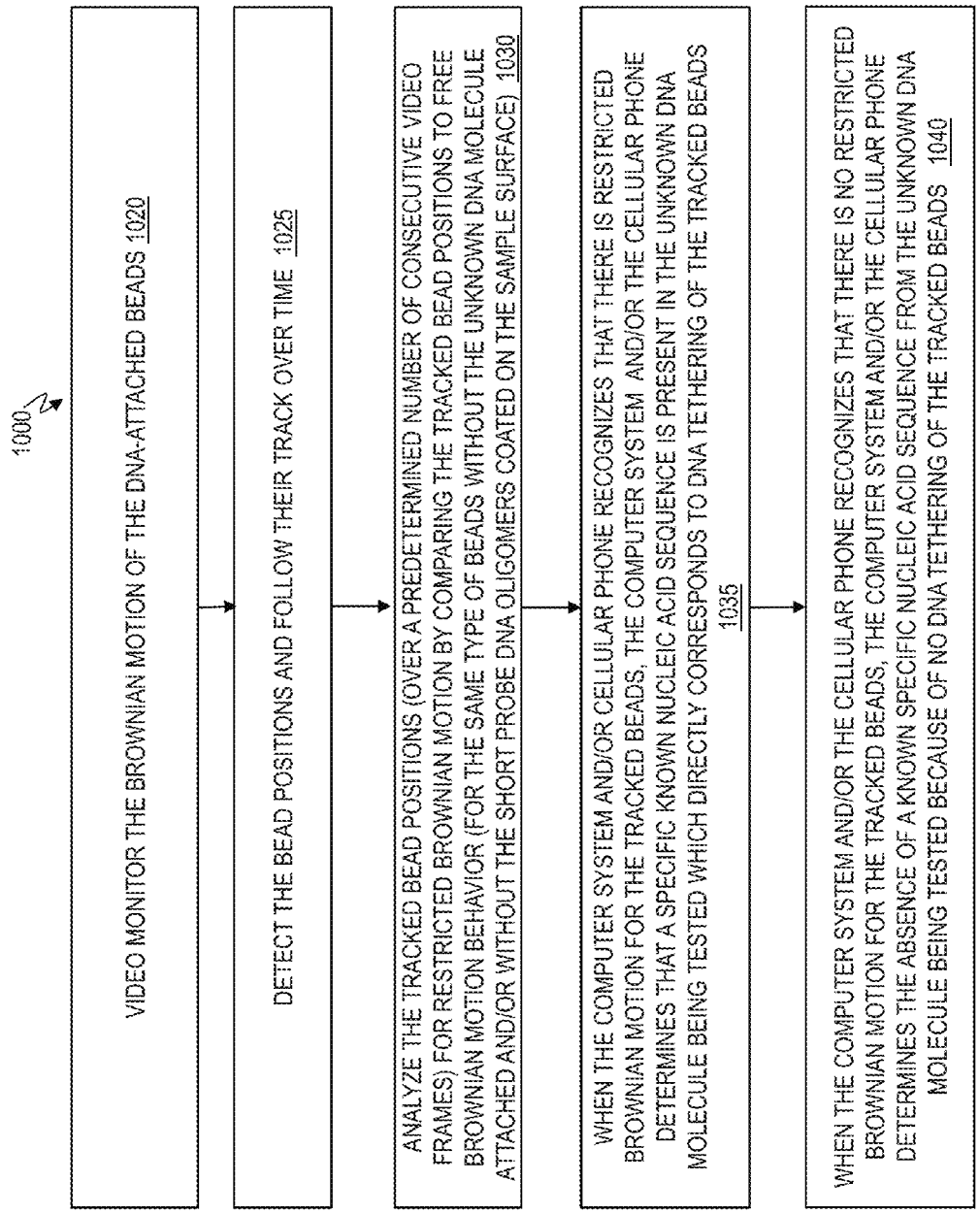

FIGS. 10A and 10B together illustrate a process 1000 of optical detection to determine the absence (i.e., when there is no tethering of the micron size polymer beads 30 to the sample surface) or presence (i.e., when there is tethering of micron size polymer beads 30 to the sample surface 10) of a nucleic acid sequence in a sample being tested according to an embodiment.

At block 1002, the glass surface or polymer surface of sample cell 10 is coated with antibody molecules 202. After most of the antibody molecules 202 bind to the surface, the sample cell surface 10 may optionally be flushed with buffer solution to remove unbound antibody molecules 202 from the solution in sample cell 10.

At block 1005, the sample cell surface 10 is coated with short probe DNA oligomers 205 in which the short probe DNA oligomers 205 are attached with anti-digoxigenin molecules 203 on one end which will bind to the antibody molecules 202 coated on the sample cell interior surface 10.

At block 1010, the unknown DNA molecule 210 being tested is biotinylated on one end (with the second molecule 220) so that the biotinylated end of the DNA molecule 210 can then be attached to the micron size polymer beads 30 coated with the first molecule 215 (e.g., streptavidin protein molecules).

At block 1015, a small amount (e.g., 10-20 microliters (μL) in one implementation) of DNA-attached beads 30 is added to the sample cell surface 10 coated with the short probe DNA oligomers 205.

At block 1020, the Brownian motion of the DNA-attached beads 30 is video monitored with, e.g., a CCD camera, other detector, and/or the cellular phone 401 in the camera setup in FIGS. 4 and 5.

At block 1025, the cellular phone 401 and/or a computer system 1200 is configured to detect the bead positions and follow their track over time.

At block 1030, the cellular phone 401 and/or a computer system 1200 is configured to analyze the tracked bead positions (over a predetermined number of consecutive video frames) for restricted Brownian motion by comparing the tracked bead positions to free Brownian motion behavior (for the same type of beads 30 in the liquid 20 without the unknown DNA molecule 210 attached and/or for the same type of beads 30 in the liquid 20 without the short probe DNA oligomers 205 coated on the sample surface.

At block 1035, when the cellular phone 401 and/or a computer system 1200 recognizes that there is restricted Brownian motion for the tracked beads 30, the cellular phone 401 and/or a computer system 1200 determines that a specific known nucleic acid sequence is present in the unknown DNA molecule 210 being tested which directly corresponds to DNA tethering of the tracked beads 30.

At block 1040, when the cellular phone 401 and/or a computer system 1200 recognizes that there is no restricted Brownian motion for the tracked beads 30, the cellular phone 401 and/or a computer system 1200 determines the absence of a specific known nucleic acid sequence from the unknown DNA molecule 210 being tested because of no DNA tethering of the tracked beads 30.

In one implementation, in performing block 1030, the cellular phone 401 and/or a computer system 1200 is configured to calculate the diffusion coefficient of the bead motion for the tracked beads 30, and then compare the calculated diffusion coefficient (of the tracked beads 30 having the DNA molecule 210 attached) to that of the known diffusion coefficient (i.e., baseline) for free particle motion (of particles/beads having the same or similar size as the tracked beads 30) to determine if there is a statistically significant restricted Brownian for the tracked beads 30.

When there is no statistically significant restricted Brownian motion for the tracked beads 30 (as compared to the known diffusion coefficient for free particle motion), then the cellular phone 401 and/or a computer system 1200 is configured to determine that there is the absence of a specific nucleic acid sequence from the unknown DNA molecule 210 being tested because of no DNA tethering of the tracked beads 30.

However, when there is statistically significant restricted Brownian motion for the tracked beads 30 (as compared to the known diffusion coefficient for free particle motion), then the cellular phone 401 and/or a computer system 1200 is configured to determine that there is the specific nucleic acid sequence present in the unknown DNA molecule 210 being tested which directly corresponds to DNA tethering of the tracked beads 30.

Figure 11A:
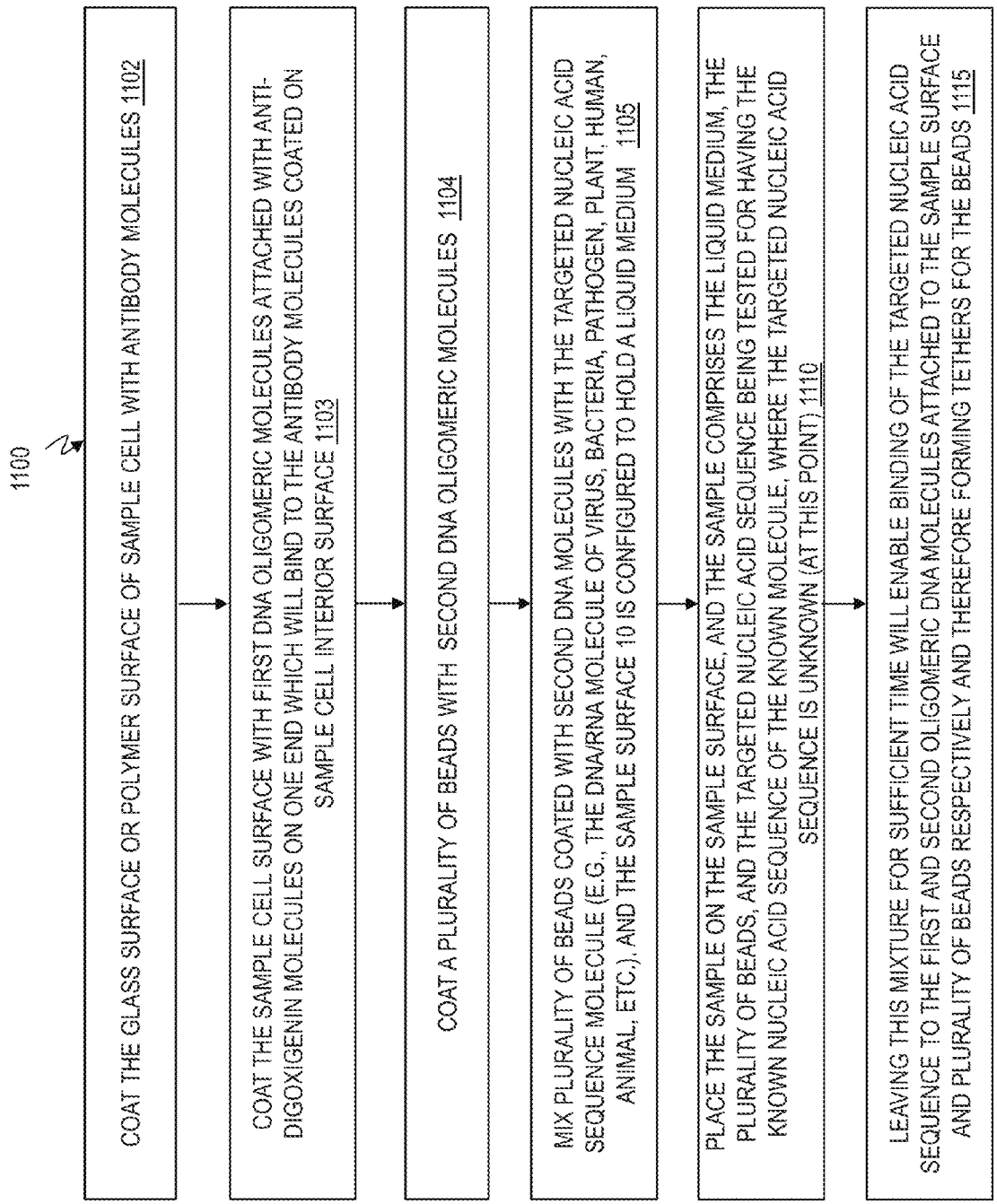
FIGS. 11A and 11B together illustrate a method to determine a presence/absence of a known nucleic acid sequence of a known molecule in a sample according to an embodiment.
Figure 11B:
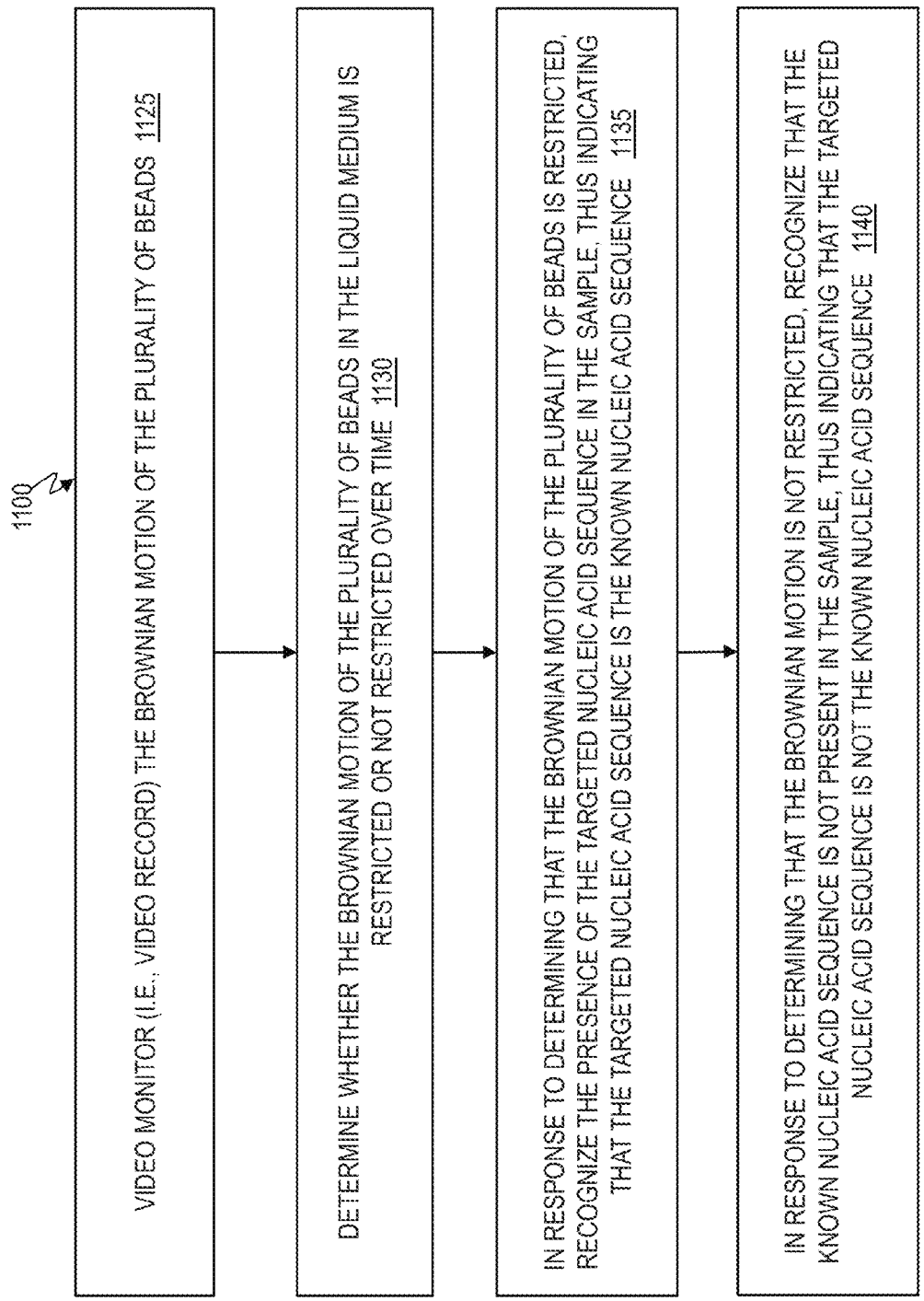

Now turning to FIGS. 11A and 11B, a method 1100 is provided to determine a presence of a known nucleic acid sequence of a known molecule in a sample in which the sample contains a targeted nucleic acid sequence 210 according to an embodiment. The known molecule is known in advance.

At block 1102, the glass surface or polymer surface of sample cell 10 is coated with antibody molecules 202.

At block 1103, the sample cell surface 10 is coated with first short probe DNA oligomeric molecules 205 attached with anti-digoxigenin molecules 203 on one end which will bind to the antibody molecules 202 coated on sample cell interior surface 10.

At block 1104, a plurality of beads are coated with second short probe DNA oligomeric molecules 1405.

At block 1105, a plurality of beads 30 coated with second short probe DNA molecules 1405 are mixed with the targeted nucleic acid sequence molecule 210 (e.g., the DNA/RNA molecule of virus, bacteria, pathogen, plant, human, animal, etc.), and the sample surface 10 is configured to hold a liquid medium 20.

At block 1110, the sample is placed on the sample surface 10, and the sample comprises the liquid medium 20, the plurality of beads 30, and the targeted nucleic acid sequence molecule 210 being tested for having the known nucleic acid sequence of the known molecule, where the targeted nucleic acid sequence is unknown (at this point).

At block 1115, this mixture is left for sufficient time (e.g., which may be 30, 30, 90 minutes in one case) enable binding of the targeted nucleic acid sequence 210 to the first and second oligomeric DNA molecules 205 and 1405 attached to the sample surface 10 and plurality of beads 30 respectively and therefore forming tethers for the beads 30.

At block 1125, the cellular phone 401 (operating as an optical device, e.g., via a video/camera recorder) is configured to video monitor (i.e., video record) the Brownian motion of the plurality of beads 30.

At block 1130, the cellular phone 401 is configured to determine whether the Brownian motion of the plurality of beads 30 in the liquid medium 20 is restricted or not restricted over time.

At block 1135, in response to determining (e.g., via the cellular phone 401) that the Brownian motion of the plurality of beads 30 is restricted, the cellular phone 401 is configured to recognize the presence of the known nucleic acid sequence in the sample, thus indicating that the targeted nucleic acid sequence 210 is the known nucleic acid sequence.

At block 1140, in response to determining that the Brownian motion is not restricted, the cellular phone 401 is configured to recognize that the known nucleic acid sequence is not present in the sample, thus indicating that the targeted nucleic acid sequence 210 is not the known nucleic acid sequence.

Determining whether the Brownian motion of the plurality of beads 30 is restricted or not restricted over time (such as over consecutive video frames of the recorded video) includes: 1) detecting bead positions of the plurality of beads 30 in the liquid medium 20; 2) tracking the bead positions of the plurality of beads 30 over time to obtain bead motion for the plurality of beads 30; and 3) comparing the bead motion tracked for the plurality of beads to free Brownian motion.

Comparing the bead motion tracked for the plurality of beads to free Brownian motion includes determining that the sample contains the known nucleic acid sequence based on the bead motion of the plurality of beads being less than the free Brownian motion.

The bead motion of the plurality of beads being less than the free Brownian motion denotes that the targeted nucleic acid sequence in the sample has tethered the plurality of beads 30 to the sample surface 10. Tethering the plurality of beads 30 to the sample surface restricts the bead motion of the plurality of beads 30. Tethering the plurality of beads 30 to the sample surface 10 restricts the bead motion of the plurality of beads to a circular motion.

The targeted nucleic acid sequence in the sample has a first end and a second end. Tethering the plurality of beads to the sample surface 10 comprises the select segment 205 coated on the sample surface 10 attaching to the first end of the targeted nucleic acid sequence 210 and comprises the first molecule 215 coated on the plurality of beads 30 attaching to the second end of the targeted nucleic acid sequence.

Comparing the bead motion tracked for the plurality of beads 30 to free Brownian motion includes determining that the sample does not contain the known nucleic acid sequence based on the bead motion of the plurality of beads 30 corresponding to the free Brownian motion.

Comparing (by the cellular phone 401) the bead motion tracked for the plurality of beads to free Brownian motion includes: 1) determining a sample diffusion coefficient of the bead motion tracked for the plurality of beads when the sample of the targeted nucleic acid sequence is added to liquid medium; 2) determining a baseline diffusion coefficient for the plurality of beads when no targeted nucleic acid sequence is added to the liquid medium 20; 3) determining that the Brownian motion of the plurality of beads is restricted when the sample diffusion coefficient is less than the baseline diffusion coefficient; 4) determining that the Brownian motion of the plurality of beads is not restricted when the sample diffusion coefficient corresponds to the baseline diffusion coefficient.

In one implementation, the plurality of beads are in the size range of 0.2 to 3.0 microns. The optical device is an electronic communication device having a lens assembly adapter.

Embodiments discussed herein can be utilized in various applications. As suggested herein, there is a growing need for early and fast diagnosis of flu-like symptoms with point-of-care diagnostic kits either at one's home or away in a doctor's office such as at an epidemic center. This is also highlighted by the recent epidemic associated with Ebola virus in Africa. At one time, it was estimated that the currently infected people that need treatment are between 10,000 and 15,000 in the countries Guinea, Sierra Leone, and Liberia. It was predicted that this number would double every month which will result in nearly 50,000 infected people in one month and 100,000 people in two months ("Containing Ebola: What it would take", Washington Post, Oct. 9, 2014. Embodiments based on the restricted Brownian motion of beads can be applied to develop a cell-phone based diagnostic kit for detecting flu virus, for example. The viral RNA/DNA can be extracted from the blood or saliva of the patient after doing the recommended preparation using commercially available RNA/DNA extraction kits. As discussed in embodiments, the extracted RNA/DNA is to detect the presence of specific RNA or DNA by the tethering the DNA/RNA forms with the specially prepared beads. It is estimated that the diagnosis can probably be done in one to two hours, and the system 480, 580 is completely portable and usable with the cellular phone.

Figure 12:
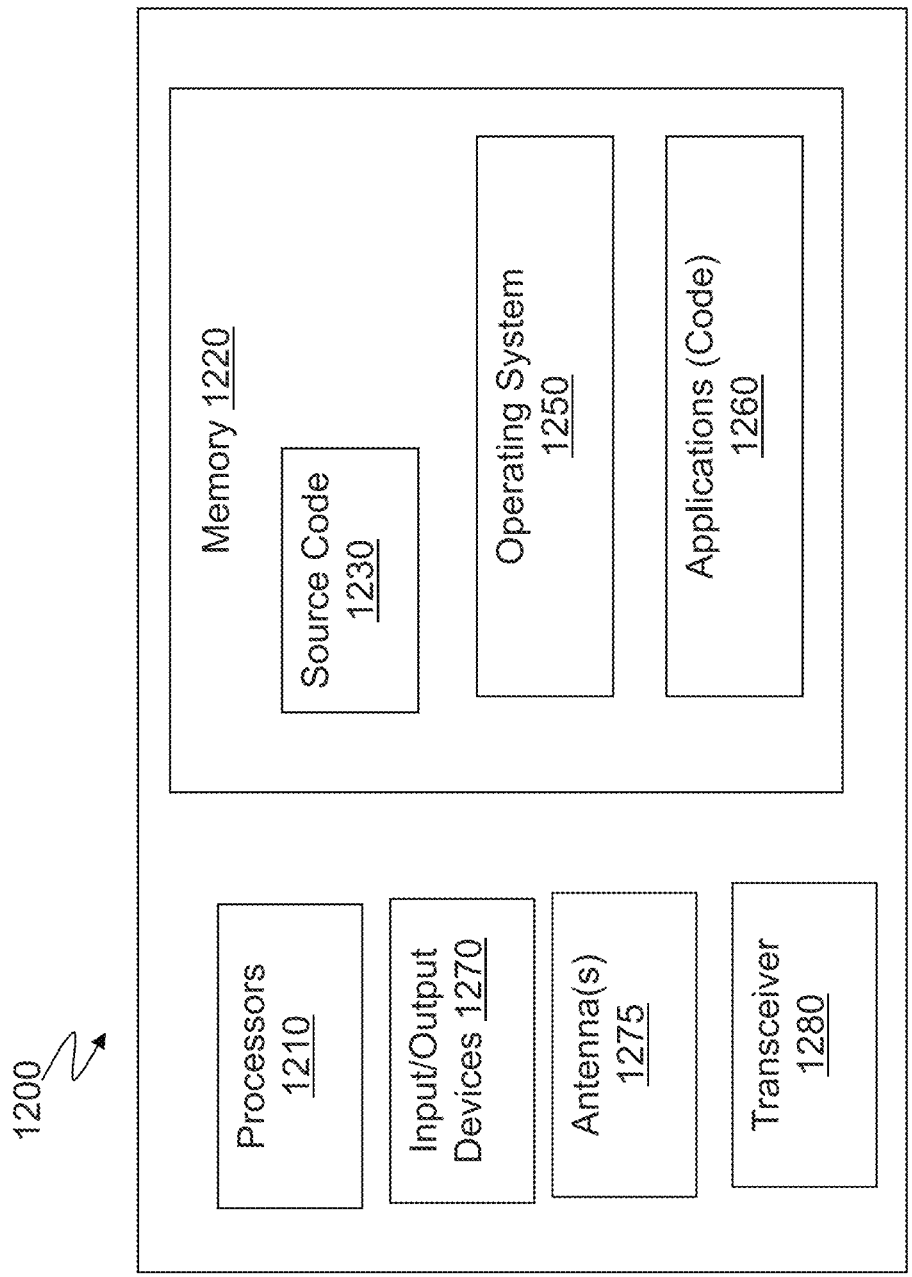
FIG. 12 illustrates an example of a computer system/phone programed to execute the features of embodiments.

FIG. 12 illustrates an example of a computer system 1200 programed to execute the features of embodiments discussed. In one case, the computer system 1200 may be implemented in the camera/video recorder cellular phone 401 discussed herein. Although a camera cellular phone 401 has been discussed, it is understood that embodiments are not limited to a use by a cellular phone. Since portability is a beneficial feature, the cellular phone 401 was discussed. It can be appreciated that other types of electronic communication devices having camera and/or video recording capabilities may be utilized such as a tablet, laptop, video camera, etc. The special lens adapter 400 can be utilized with these electronic devices if needed.

Various methods, procedures, modules, flow diagrams, tools, applications, circuits, elements, and techniques discussed herein may also incorporate and/or utilize the capabilities of the computer 1200. Moreover, capabilities of the computer 1200 may be utilized to implement features of exemplary embodiments discussed herein. One or more of the capabilities of the computer 1200 may be utilized to implement, incorporate, to connect to, and/or to support any element discussed herein (as understood by one skilled in the art).

Generally, in terms of hardware architecture, the computer 1200 may include one or more processors 1210, computer readable storage memory 1220, and one or more input and/or output (I/O) devices 1270 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 1210 is a hardware device for executing software that can be stored in the memory 1220. The processor 1210 can be virtually any custom made or commercially available processor, a central processing unit (CPU), a data signal processor (DSP), or an auxiliary processor among several processors associated with the computer 1200, and the processor 1210 may be a semiconductor based microprocessor (in the form of a microchip) or a microprocessor. Note that the memory 1220 can have a distributed architecture, where various components are situated remote from one another, but can be accessed by the processor 1210.

The software in the computer readable memory 1220 may include one or more separate programs, each of which comprises an ordered listing of executable instructions for implementing logical functions. The software in the memory 1220 includes a suitable operating system (O/S) 1250, source code 1230, and one or more applications 1260 of the exemplary embodiments. As illustrated, the application 1260 comprises numerous functional components for implementing the features, processes, methods, functions, and operations of the exemplary embodiments. The application

1260 of the computer 1200 may represent numerous applications, agents, software components, modules, interfaces, controllers, etc., as discussed herein but the application 1260 is not meant to be a limitation.

The operating system 1250 may control the execution of other computer programs, and provides scheduling, input-output control, file and data management, memory management, and communication control and related services.

The application 1260 may be a source program, executable program (object code), script, or any other entity comprising a set of instructions to be performed. When a source program, then the program is usually translated via a compiler, assembler, interpreter, or the like, which may or may not be included within the memory 1220, so as to operate properly in connection with the O/S 1250. Furthermore, the application 1260 can be written as (a) an object oriented programming language, which has classes of data and methods, or (b) a procedure programming language, which has routines, subroutines, and/or functions.

The I/O devices 1270 may include input devices (or peripherals) such as, for example but not limited to, a mouse, keyboard, scanner, microphone, camera, etc. Furthermore, the I/O devices 1270 may also include output devices (or peripherals), for example but not limited to, a printer, display, etc. Finally, the I/O devices 1270 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 1270 also include components for communicating over various networks, such as the Internet or an intranet. The I/O devices 1270 may be connected to and/or communicate with the processor 1210 utilizing Bluetooth connections and cables (via, e.g., Universal Serial Bus (USB) ports, serial ports, parallel ports, FireWire, HDMI (High-Definition Multimedia Interface), PCIe, InfiniBand®, or proprietary interfaces, etc.).

The computer 1200 includes one or more antennas 1275 for transmitting and receiving over-the-air-signals (e.g., radio signals such as microwave signals, GPS signals, etc.) via a transceiver 1280.

When the computer 1200 is in operation, the processor 1210 is configured to execute software stored within the memory 1220, to communicate data to and from the memory 1220, and to generally control operations of the computer 1200 pursuant to the software. The application 1260 and the O/S 1250 are read, in whole or in part, by the processor 1210, perhaps buffered within the processor 1210, and then executed.

When the application 1260 is implemented in software it should be noted that the application 1260 can be stored on virtually any computer readable storage medium for use by or in connection with any computer related system or method.

The application 1260 can be embodied in any computer-readable medium for use by or in connection with an instruction execution system, apparatus, server, or device, such as a computer-based system, processor-containing system, or other system that can fetch the instructions from the instruction execution system, apparatus, or device and execute the instructions.

In exemplary embodiments, where the application 1260 is implemented in hardware, the application 1260 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It is understood that the computer 1200 includes non-limiting examples of software and hardware components that may be included in various devices, servers, and systems discussed herein, and it is understood that additional software and hardware components may be included in the various devices and systems discussed in exemplary embodiments.

As will be appreciated by one skilled in the art, one or more aspects of the present invention may be embodied as a system, method or computer program product. Accordingly, one or more aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, one or more aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method to determine a presence of a known nucleic acid sequence of a known molecule in a sample in which the sample contains a targeted nucleic acid sequence, the method comprising:

coating a sample surface with a select segment of the known nucleic acid sequence of the known molecule, wherein the sample surface is configured to hold a liquid medium, wherein the select segment of the known nucleic acid sequence of the known molecule ranges from 8 to 40 bases;

coating a plurality of beads with a first molecule, wherein a number of the plurality of beads ranges from 100 to 1000 and a size of the plurality of beads ranges from 0.2 to 3.0 microns, wherein the plurality of beads are provided to be sufficient for recognition of a Brownian motion;

attaching the targeted nucleic acid sequence to a second molecule that is configured to bind to the first molecule, such that the targeted nucleic acid sequence is attached to the plurality of beads via the first and second molecules;

placing the sample on the sample surface, the sample including the liquid medium, the plurality of beads, and the targeted nucleic acid sequence being tested for having the known nucleic acid sequence of the known molecule, wherein the select segment of the known nucleic acid sequence of the known molecule is intended to be complementary to the targeted nucleic acid sequence;

video monitoring the Brownian motion of the plurality of beads with an optical device;

determining whether the Brownian motion of the plurality of beads in the liquid medium is restricted or not restricted over time;

in response to determining that the Brownian motion of the plurality of beads is restricted and in response to the plurality of beads being tethered to the sample surface when the select segment of the known nucleic acid sequence of the known molecule is complementary to the targeted nucleic acid sequence, recognizing the presence of the known nucleic acid sequence in the sample, thus indicating that the targeted nucleic acid sequence is the known nucleic acid sequence; and in response to determining that the Brownian motion is not restricted and in response to the plurality of beads not being tethered to the sample surface when the select segment of the known nucleic acid sequence of the known molecule is not complementary to the targeted nucleic acid sequence, recognizing that the known nucleic acid sequence is not present in the sample, thus indicating that the targeted nucleic acid sequence is not the known nucleic acid sequence:

wherein determining whether the Brownian motion of the plurality of beads is restricted or not restricted over time includes:

detecting bead positions of the plurality of beads in the liquid medium;

tracking the bead positions of the plurality of beads over time to obtain bead motion for the plurality of beads; and comparing the bead motion tracked for the plurality of beads to a free Brownian motion;

wherein comparing the bead motion tracked for e plurality of beads to the free Brownian motion includes:

determining a sample diffusion coefficient of the bead motion tracked for the plurality of beads when the sample of the targeted nucleic acid sequence is added to the liquid medium;

determining a baseline diffusion coefficient for the plurality of beads when no targeted nucleic acid sequence is added to the liquid medium;

determining that the Brownian motion of the plurality of beads is restricted when the sample diffusion coefficient is less than the baseline diffusion coefficient;

determining that the Brownian motion of the plurality of beads is not restricted when the sample diffusion coefficient corresponds to the baseline diffusion coefficient.

2. The method of claim 1, wherein comparing the bead motion tracked for the plurality of beads to the free Brownian motion includes determining that the sample contains the known nucleic acid sequence based on the bead motion of the plurality of beads being less than the free Brownian motion.

3. The method of claim 2, wherein the bead motion of the plurality of beads being less than the free Brownian motion denotes that the targeted nucleic acid sequence in the sample has tethered the plurality of beads to the sample surface.

4. The method of claim 3, wherein tethering the plurality of beads to the sample surface restricts the bead motion of the plurality of beads.

5. The method of claim 3, wherein tethering the plurality of beads to the sample surface restricts the bead motion of the plurality of beads to a circular motion.

6. The method of claim 3, wherein the targeted nucleic acid sequence in the sample has a first end and a second end;

wherein tethering the plurality of beads to the sample surface comprises the select segment coated on the sample surface attaching to the first end of the targeted nucleic acid sequence and comprises the first molecule coated on the plurality of beads attaching to the second end of the targeted nucleic acid sequence.

7. The method of claim 1, wherein comparing the bead motion tracked for the plurality of beads to the free Brownian motion includes determining that the sample does not contain the known nucleic acid sequence based on the bead motion of the plurality of beads corresponding to the free Brownian motion.

8. The method of claim 1, wherein the plurality of beads are micron size; and wherein the optical device is an electronic communication device having a lens assembly adapter.

* * * * *